(12) United States Patent
Kuramochi et al.

(10) Patent No.: US 7,855,198 B2
(45) Date of Patent: Dec. 21, 2010

(54) BENZAMIDE DERIVATIVE OR SALT THEREOF

(75) Inventors: Takahiro Kuramochi, Chuo-ku (JP); Norio Asai, Chuo-ku (JP); Kazuhiro Ikegai, Chuo-ku (JP); Seijiro Akamatsu, Chuo-ku (JP); Hironori Harada, Chuo-ku (JP); Noriko Ishikawa, Chuo-ku (JP); Shohei Shirakami, Chuo-ku (JP); Satoshi Miyamoto, Chuo-ku (JP); Toshihiro Watanabe, Chuo-ku (JP); Tetsuo Kiso, Chuo-ku (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 12/496,993

(22) Filed: Jul. 2, 2009

(65) Prior Publication Data
US 2009/0270365 A1 Oct. 29, 2009

Related U.S. Application Data

(62) Division of application No. 10/560,282, filed as application No. PCT/JP2004/008479 on Jun. 10, 2004, now Pat. No. 7,585,878.

(30) Foreign Application Priority Data

Jun. 12, 2003 (JP) ............... 2003-167865
Dec. 3, 2003 (JP) ............... 2003-405086

(51) Int. Cl.
*C07D 413/10* (2006.01)
*C07D 413/14* (2006.01)
*A61K 31/538* (2006.01)

(52) U.S. Cl. ................... 514/230.5; 544/105
(58) Field of Classification Search ................ 544/105; 514/230.5
See application file for complete search history.

(56) References Cited

U.S. PATENT DOCUMENTS 6,110,934 A 8/2000 Harling et al.
6,841,560 B2 1/2005 Thompson et al.
2001/0016657 A1 8/2001 Thompson et al.
2002/0132853 A1 9/2002 Bakthavatchalam et al.
2003/0144320 A1 7/2003 Thompson et al.
2004/0209912 A1 10/2004 Thompson et al.
2004/0259875 A1 12/2004 Yura et al.
2005/0004133 A1 1/2005 Makings et al.
2005/0154230 A1 7/2005 Yura et al.
2005/0165049 A1 7/2005 Hulme et al.
2005/0209213 A1 9/2005 Ishihara et al.

FOREIGN PATENT DOCUMENTS

| JP | 2002-3370 | 1/2002 |
|----|-----------|--------|
| JP | 2003-55209 | 2/2003 |
| WO | WO 97/48683 | 12/1997 |
| WO | WO 98/41508 | 9/1998 |
| WO | WO 01/21577 | 3/2001 |
| WO | WO 02/08221 | 1/2002 |
| WO | WO 03/014064 | 2/2003 |
| WO | WO 03/035624 | 5/2003 |
| WO | WO 03/055848 | 7/2003 |
| WO | WO 03/068749 | 8/2003 |
| WO | WO 2004/056774 | 7/2004 |
| WO | WO 2004/072069 | 8/2004 |
| WO | WO 2004/108133 | 12/2004 |

*Primary Examiner*—Kathsay T Habte
(74) *Attorney, Agent, or Firm*—Oblon, Spivak, McClelland, Maier & Neustadt, L.L.P.

(57) ABSTRACT

There is provided a compound having a capsaicin receptor VR1 inhibitory activity and useful as a therapeutic agent for various pains including inflammatory pain and neurogenic pain, migraine, cluster headache, bladder diseases including overactive bladder, and the like.

A benzamide derivative or a salt thereof wherein a benzene ring is attached to a D ring (a monocyclic or bicyclic hydrocarbon ring or a monocyclic or bicyclic heteroaromatic ring) through an amide bond, the benzene ring is directly bonded to an E ring (a monocyclic or bicyclic hydrocarbon ring or a monocyclic or bicyclic heteroaromatic ring), and the benzene ring is further bonded to A (an amino moiety, a monocyclic or bicyclic heterocycle) through L (a lower alkylene).

19 Claims, No Drawings

BENZAMIDE DERIVATIVE OR SALT THEREOF

TECHNICAL FIELDS

The present invention relates to novel benzamide derivatives or salts thereof useful as medicaments, particularly, capsaicin receptor VR1 (Vanilloid Receptor 1) activation inhibitor, and the medicaments.

BACKGROUND ART

Capsaicin, which is a main component of chili pepper, is an irritant substance and induces pain by activating capsaicin receptor VR1 present in primary afferent sensory nerves (mainly C fibers). VR1 was cloned [Nature 389: 816-824 (1997)] and was found to be a non-selective cation channel having a high $Ca^{2+}$ permeability. VR1 is activated by not only capsaicin but also thermal stimulation or acid (proton) stimulation. Moreover, it was also revealed that inflammation-related substances such as ATP and bradykinin act on a metabotropic receptor and regulate VR1 activity through activation of phospholipase C (PLC)/activation of protein kinase C (PKC). Furthermore, it is known that not only a pain reaction by capsaicin disappears but also hyperalgesia at inflammation decreases in VR1-deficit mice [Nature 405: 183-187 (2000)]. From these facts, VR1 is considered to participate in pains at various clinical conditions.

Capsaicin induces pain by activating VR1 but is known to exhibit an analgesic action inversely by desensitizing afferent nerves through continuous activation and thereby inhibiting subsequent activation. Actually, a capsaicin cream is used for treating neuropathic pains such as postherpetic neuralgia or pain in diabetic neuropathy and inflammatory pains such as rheumatic joint pain. Moreover, the reason why the bladder dysfunction observed in patients like spinal cord injury and the like is alleviated by injection of capsaicin or an analogous substance, reginiferatoxin (RTX) into bladder is consider to be based on desensitization of afferent nerves as in the case of the analgesic action.

Not only desensitization induced by a VR1 agonist but also a VR1 antagonist exhibits an analgesic action. It is known that capsazepine known as a VR1 antagonist from long ago exhibits efficiency for neuropathic pains and inflammatory pains in animal models [J. Pharmacol. Exp. Ther. 304: 56-62 (2003)]. An endogenous ligand for VR1 is unclear, but a plurality of candidate substances have been reported. An antagonist is considered to exhibit the analgesic action through inhibition of VR1 activation by competition with these substances. Thus, the inhibition of VR1 activation not only exhibit an analgesic action, but also is expected to lead to prevention or therapy of symptoms and diseases relevant to VR1 activation.

Therefore, a compound having an inhibitory activity of VR1 activation is considered to be useful for various pains including neuropathic pains and inflammatory pains, headaches such as migraine and cluster headache, pruritus, bladder diseases including overactive bladder and interstitial cystitis.

Recently, investigation on the compounds having an inhibitory activity of VR1 activation has been advanced. For example, a pamphlet of International Publication No. 02/08221 (Patent Document 1) describes that piperazine derivatives represented by the following general formula:

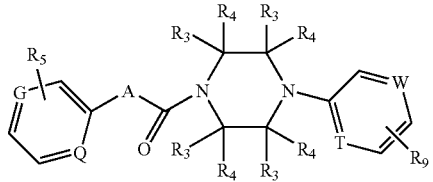

wherein G, Q, T, and W are the same or different and each represents N, CH, or $CR_5$, A is absent or represents O, S, or the like, $R_3$ and $R_4$ each independently represents hydrogen atom, halogen atom, hydroxy, amino, cyano, or the like, $R_5$ represents cyano, hydroxy, amino, or the like, and $R_9$ represents halogen atom, cyano, nitro, or the like (cf. Patent Document 1 for details of the symbols in the formula), can be used for treatment of chronic and acute pains, psoriasis, incontinence of urine, and the like as a ligand for receptor of capsaicin receptor.

Moreover, a pamphlet of International Publication No. 03/014064 (Patent Document 2) describes that amine derivatives represented by the following general formula:

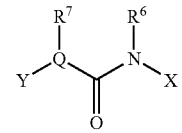

wherein Q represents CH or N, Y represents substituted naphthalene, $R^6$ represents hydrogen atom or methyl, $R^7$ represents hydrogen atom or methyl, X represents substituted benzene, substituted naphthalene, or the like (cf. the Publication for details of the symbols in the formula), can be used for therapy of incontinence of urine, overactive bladder, chronic pain, neurogenic pains, postoperative pain, and the like.

Furthermore, a pamphlet of International Publication No. 03/068749 (Patent Document 3) describes that amide derivatives represented by the following general formula:

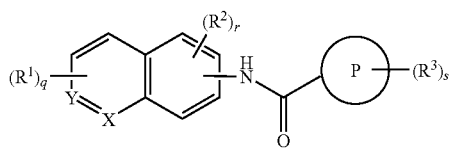

| X | Y |
|---|---|
| N | $CR^9$ |
| $NR^8$ | $C(R^9)_2$ |
| $CR^9$ | N |
| $C(R^9)_2$ | $NR^8$ | wherein X and Y represent a combination described in the above table, P represents a phenyl or a heteroaryl or the like, $R^1$ and $R^2$ each represents halo, alkyl, alkoxy, $NR^4R^5$, or the like, $R^3$ represents alkyl, alkoxy, phenyl, or the like which may be substituted by $R^2$ group, q, r, and s each represents 0 to 3, and $R^4$ and $R^5$ each represents hydrogen atom, alkyl, or R[4] and R[5] together with the nitrogen atom form a heterocyclic ring (cf. the Publication for details of the symbols in the formula), can be used as an antagonist of VR1 for therapy and prevention of various pains.

In the application, there are disclosed compounds wherein a combination of P and R[3] is biphenyl but, with regard to the compound wherein the biphenyl ring contains further substituents R[3], all the substituent are low-molecular-weight groups such as lower alkyl groups, halogens, or substituted alkoxy groups.

On the other hand, there have been reported biphenylcarboxamide compounds having a nitrogen-containing heterocycle, such as quinoline or tetrahydroquinoline on the amide nitrogen. For example, a pamphlet of International Publication No. 01/21577 (Patent Document 4) and a pamphlet of International Publication No. 03/035624 (Patent Document 5) describe tetrahydroquinoline derivatives and quinoline derivatives having an anti-obesity activity based on MCH receptor antagonism, respectively. Moreover, a pamphlet of International Publication No. 98/41508 (Patent Document 6) and a pamphlet of International Publication No. 97/48683 (Patent Document 7) describe tetrahydroisoquinoline derivatives having anticonvulsant activity. However, all the compounds are restricted to those having no substituent or only low-molecular-weight substituents on the biphenyl ring. Furthermore, there is neither disclosure nor suggestion on inhibitory activity of VR1 receptor activation.

As mentioned above, a capsaicin receptor VR1 activation inhibitor is expectable as a therapeutic agent for various pains including inflammatory pains and neurogenic pains, migraine, cluster headache, bladder diseases including overactive bladder, and the like. It is highly desired to develop a novel capsaicin receptor VR1 activation inhibitor which is different in chemical structure from the above known compounds and has a further excellent effect.

DISCLOSURE OF THE INVENTION

As a result of the extensive studies on compounds having an inhibitory activity of capsaicin receptor VR1 activation, the present inventors have found that a compound represented by the following general formula (I) wherein a benzene ring is attached to a D ring (a monocyclic or bicyclic hydrocarbon ring or a monocyclic or bicyclic heteroaromatic ring) through an amide bond, the benzene ring is directly bonded to an E ring (a monocyclic or bicyclic hydrocarbon ring or a monocyclic or bicyclic heteroaromatic ring), and the benzene ring is further bonded to A (an amino moiety, a monocyclic or bicyclic heterocycle) through L (a lower alkylene) has an excellent inhibitory activity of VR1 activation. Thus, they have accomplished the present invention. Namely, the invention relates to a compound represented by the following formula (I) and a salt thereof, and a medicament containing them as an active ingredient.

In this connection, the invention includes those wherein a cyclic group represented by D is a nitrogen-containing bicyclic heterocycle such as quinoline or tetrahydroisoquinoline, however, the compound is different in chemical structure from the specifically disclosed compounds described in Patent Document 3 in such a viewpoint that the benzene ring is bonded to A (an amino moiety, a monocyclic or bicyclic heterocycle) through L (a lower alkylene).

[1] A benzamide derivative represented by the following general formula (I):

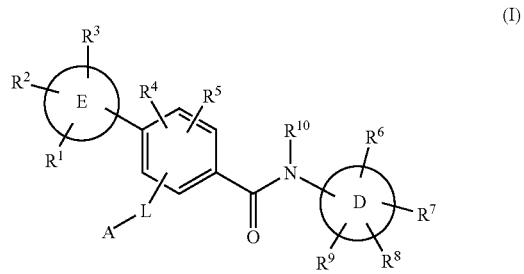

wherein the symbols have the following meanings:

A:

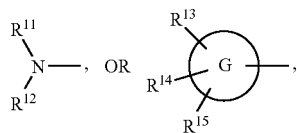

L: a lower alkylene,

D ring and E ring: the same or different, a monocyclic or bicyclic hydrocarbon ring, or a 5- to 12-membered monocyclic or bicyclic heteroaromatic ring containing 1 to 4 atoms of one or more kinds of heteroatoms selected from the group consisting of N, S, and O, G ring: a 4- to 12-membered monocyclic or bicyclic heterocycle containing 1 to 4 atoms of one or more kinds of heteroatoms selected from the group consisting of N, S, and O, R[1] to R[9]: the same or different, a hydrogen atom, a halogen atom, a lower alkyl, a halogen-substituted lower alkyl, —OH, —SH, —O-lower alkyl, —O-lower alkyl-NH-lower alkyl, —O-lower alkyl-N(lower alkyl)$_2$, =O, —NH$_2$, —NH-lower alkyl, —N(lower alkyl)$_2$, —S-lower alkyl, —SO-lower alkyl, —SO$_2$-lower alkyl, —CN, —COOH, —C(=O)—O-lower alkyl, —C(=O)—NH$_2$, —C(=O)—NH-lower alkyl, —C(=O)—N(lower alkyl)$_2$, —NH—C(=O)-lower alkyl, —NH—SO$_2$-lower alkyl, —SO$_2$—NH$_2$, —SO$_2$—NH-lower alkyl, —C(=O)-lower alkyl, —NO$_2$ or a nitrogen-containing saturated heterocycle, R[10]: a hydrogen atom or a lower alkyl, R[11] to R[15]: the same or different, a hydrogen atom, a halogen atom, a lower alkyl, a halogen-substituted lower alkyl, —OH, —O-lower alkyl, —S-lower alkyl, —SO-lower alkyl, —SO$_2$-lower alkyl, =O, —C(=O)H, —C(=O)-lower alkyl, —COOH, —CN, —NH$_2$, —NH-lower alkyl, —N(lower alkyl)$_2$, —C(=O)—NH$_2$, —C(=O)—NH-lower alkyl, —C(=O)—N(lower alkyl)$_2$, —C(=O)-aryl, —C(=O)—NH-aryl, —NH—C(=O)-lower alkyl, —NH—C(=O)-aryl, —NH—SO$_2$-lower alkyl, —N(lower alkyl)-SO$_2$-lower alkyl, -lower alkylene-NH—SO$_2$-lower alkyl, -lower alkylene-NH—SO$_2$-aryl, —C(=O)—O-lower alkyl, -lower alkylene-OH, -lower alkylene-C(=O)—NH-lower alkyl, -lower alkylene-C(=O)—N(lower alkyl)$_2$, -lower alkylene-C(=O)—NH$_2$, -lower alkylene-C(=O)—OH, -lower alkylene-O-lower alkyl, -lower alkylene-S-lower alkyl, -lower alkylene-O—C(=O)-lower alkyl, -lower alkylene-NH-lower alkyl, -lower alkylene-N(lower alkyl)$_2$-lower alkylene-aryl, a cycloalkyl, an aryl, -(4- to 12-membered monocyclic or bicyclic heterocycle containing 1 to 4 atoms of one or more kinds of heteroatoms selected from the group consisting of N, S, and O), —O-(4- to 12-membered monocyclic or bicyclic heterocycle containing 1 to 4 atoms of one or more kinds of heteroatoms selected from the group consisting of N, S, and O), -lower alkylene-(4- to 12-membered monocyclic or bicyclic heterocycle containing 1 to 4 atoms of one or more kinds of heteroatoms selected from the group consisting of N, S, and O), —C(=O)-(4- to 12-membered monocyclic or bicyclic heterocycle containing 1 to 4 atoms of one or more kinds of heteroatoms selected from the group consisting of N, S, and O), -lower alkylene-N(lower alkyl)-(4- to 12-membered monocyclic or bicyclic heterocycle containing 1 to 4 atoms of one or more kinds of heteroatoms selected from the group consisting of N, S, and O), or —C(=O)—NH-(4- to 12-membered monocyclic or bicyclic heterocycle containing 1 to 4 atoms of one or more kinds of heteroatoms selected from the group consisting of N, S, and O), and the above monocyclic or bicyclic heterocycle may be substituted by halogen atom(s), lower alkyl(s), —O-lower alkyl, or —OH, and the same shall apply hereinafter, or a salt thereof.

[2] The compound according to the above [1], wherein the symbols represented by D, E, $R^1$ to $R^9$, and $R^{11}$ to $R^{15}$ in the above formula (I) have the following meanings:

D ring and E ring: the same or different, a benzene ring, a naphthalene ring, or a 5- to 12-membered monocyclic or bicyclic heteroaromatic ring containing 1 to 4 atoms of one or more kinds of heteroatoms selected from the group consisting of N, S, and O, $R^1$ to $R^9$: the same or different, a hydrogen atom, a halogen atom, a lower alkyl, a halogen-substituted lower alkyl, —OH, —SH, —O-lower alkyl, —O-lower alkyl-NH-lower alkyl, —O-lower alkyl-N(lower alkyl)$_2$, =O, —NH$_2$, —NH-lower alkyl, —N(lower alkyl)$_2$, —S-lower alkyl, —SO-lower alkyl, —SO$_2$-lower alkyl, —CN, —COOH, —C(=O)—NH$_2$, —C(=O)—NH-lower alkyl, —C(=O)—N(lower alkyl)$_2$, or —NH—C(=O)-lower alkyl, $R^{11}$ to $R^{15}$: the same or different, a hydrogen atom, a halogen atom, a lower alkyl, a halogen-substituted lower alkyl, —OH, —O-lower alkyl, —S-lower alkyl, —SO-lower alkyl, —SO$_2$-lower alkyl, =O, —C(=O)H, —C(=O)-lower alkyl, —COOH, —CN, —NH$_2$, —NH-lower alkyl, —N(lower alkyl)$_2$, —C(=O)—NH$_2$, —C(=O)—NH-lower alkyl, —C(=O)—N(lower alkyl)$_2$, —C(=O)-aryl, —C(=O)—NH-aryl, —NH—C(=O)-lower alkyl, —NH—C(=O)-aryl, —NH—SO$_2$-lower alkyl, —N(lower alkyl)-SO$_2$-lower alkyl, —C(=O)—O-lower alkyl, -lower alkylene-O-lower alkyl, -lower alkylene-NH-lower alkyl, -lower alkylene-N(lower alkyl)$_2$, -lower alkylene-aryl, a cycloalkyl, an aryl, a 4- to 12-membered monocyclic or bicyclic heterocycle containing 1 to 4 atoms of one or more kinds of heteroatoms selected from the group consisting of N, S, and O, -lower alkylene-(4- to 12-membered monocyclic or bicyclic heterocycle containing 1 to 4 atoms of one or more kinds of heteroatoms selected from the group consisting of N, S, and O), —C(=O)-(4- to 12-membered monocyclic or bicyclic heterocycle containing 1 to 4 atoms of one or more kinds of heteroatoms selected from the group consisting of N, S, and O), -lower alkylene-N(lower alkyl)-(4- to 12-membered monocyclic or bicyclic heterocycle containing 1 to 4 atoms of one or more kinds of heteroatoms selected from the group consisting of N, S, and O), or —C(=O)—NH-(4- to 12-membered monocyclic or bicyclic heterocycle containing 1 to 4 atoms of one or more kinds of heteroatoms selected from the group consisting of N, S, and O).

There may be mentioned the compound according to the following [3] as a preferred embodiment of the invention, the compounds according to the following [4] to [9] as more preferred embodiments, and the compound according to the following [10] as a particularly preferred embodiment.

[3] The compound according to the above [1], wherein the ring represented by E in the above formula (I) is a benzene or thiophene ring, more preferably a benzene ring.

[4] The compound according to the above [3], wherein the compound represented by A in the above formula (I) is the following formula:

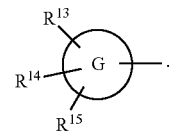

[4a] More preferably, the compound according to the above [4], wherein the ring represented by G in the above formula (I) is a nitrogen-containing saturated heterocycle, more preferably a ring selected from tetrahydropyridine, tetrahydroquinoline, tetrahydroisoquinoline, piperidine, pyrrolidine, morpholine, azepane, and 1,4-oxazepane and the ring nitrogen atom is bonded to L.

[4b] More preferably, the compound according to the above [4], wherein the ring represented by G in the above formula (I) is a ring selected from morpholine, piperidine, and pyrrolidine and the ring nitrogen atom is bonded to L.

[4c] More preferably, the compound according to the above [4], wherein the ring represented by D in the above formula (I) is a ring selected from benzothiazole, quinoline, isoquinoline, indoline, tetrahydroquinoline, tetrahydroisoquinoline, 3,4-dihydro-2H-1,4-benzoxazine, dihydroquinoline, and dihydroisoquinoline.

[4d] More preferably, the compound according to the above [4], further preferably according to the above [4a], more further preferably according to the above [4b], wherein the ring represented by D in the above formula (I) together with the groups represented by $R^6$ to $R^9$ to be bonded thereto form a group selected from the following formulae:

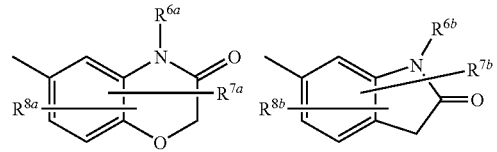

wherein the symbols have the following meanings: $R^{6a}$ and $R^{6b}$: the same or different, a hydrogen atom, a lower alkyl, or a halogen-substituted lower alkyl, and $R^{7a}$, $R^{8a}$, $R^{7b}$, and $R^{8b}$: the same or different, a hydrogen atom, a halogen atom, a lower alkyl, or a halogen-substituted lower alkyl.

Or, the compound according to the above [4], further preferably according to the above [4a], more further preferably according to the above [4b], wherein the ring represented by D in the above formula (I) together with the groups represented by $R^6$ to $R^9$ to be bonded thereto form a group selected from the following formulae:

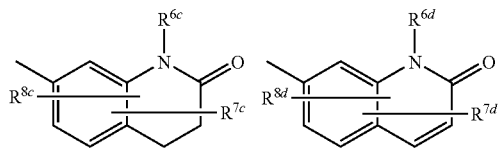

wherein the symbols have the following meanings:

$R^{6c}$ and $R^{6d}$: the same or different, a hydrogen atom, a lower alkyl, or a halogen-substituted lower alkyl, and $R^{7c}$, $R^{8c}$, $R^{7d}$, and $R^{8d}$: the same or different, a hydrogen atom, a halogen atom, a lower alkyl, or a halogen-substituted lower alkyl.

[4e] The compound according to the above [4], wherein at least one of the groups represented by $R^{13}$ to $R^{15}$ is a halogen atom, a lower alkyl, a halogen-substituted lower alkyl, —OH, —O-lower alkyl, —NH$_2$, —N(lower alkyl)$_2$, —C(=O)—NH$_2$, —C(=O)—N(lower alkyl)$_2$, —NH—C(=O)-lower alkyl, —C(=O)—O-lower alkyl, -lower alkylene-O-lower alkyl, an aryl, a -(4- to 12-membered monocyclic or bicyclic heterocycle containing 1 to 4 atoms of one or more kinds of heteroatoms selected from the group consisting of N, S, and O), or -lower alkylene-(4- to 12-membered monocyclic or bicyclic heterocycle containing 1 to 4 atoms of one or more kinds of heteroatoms selected from the group consisting of N, S, and O), and the other is a hydrogen atom. More preferably, the compound according to the above [4], wherein at least one of the symbols represented by $R^{13}$ to $R^{15}$ is a lower alkyl, —O-lower alkyl, —N(lower alkyl)$_2$, -(4- to 12-membered monocyclic or bicyclic heterocycle containing 1 to 4 atoms of one or more kinds of heteroatoms selected from the group consisting of N, S, and O), or -lower alkylene-(4- to 12-membered monocyclic or bicyclic heterocycle containing 1 to 4 atoms of one or more kinds of heteroatoms selected from the group consisting of N, S, and O) and the other is a hydrogen atom.

[5] The compound according to the above [3], wherein the group represented by A in the above formula (I) is the following formula:

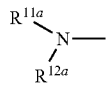

wherein the symbols have the following meanings:

$R^{11a}$ and $R^{12a}$: the same or different, a hydrogen atom, a lower alkyl, a halogen-substituted lower alkyl, —O-lower alkyl, —SO$_2$-lower alkyl, —C(=O)H, —C(=O)-lower alkyl, —CN, —NH$_2$, —NH-lower alkyl, —N(lower alkyl)$_2$, —C(=O)—NH$_2$, —C(=O)—NH-lower alkyl, —C(=O)—N(lower alkyl)$_2$, —C(=O)-aryl, —C(=O)—NH-aryl, —NH—C(=O)-lower alkyl, —NH—C(=O)-aryl, —NH—SO$_2$-lower alkyl, —N(lower alkyl)-SO$_2$-lower alkyl, -lower alkylene-NH—SO$_2$-lower alkyl, -lower alkylene-NH—SO$_2$-aryl, —C(=O)—O-lower alkyl, -lower alkylene-OH, -lower alkylene-C(=O)—NH-lower alkyl, -lower alkylene-C(=O)—N(lower alkyl)$_2$, -lower alkylene-C(=O)—NH$_2$, -lower alkylene-C(=O)—OH, -lower alkylene-O-lower alkyl, -lower alkylene-S-lower alkyl, -lower alkylene- O—C(=O)-lower alkyl, -lower alkylene-NH-lower alkyl, -lower alkylene-N(lower alkyl)$_2$, -lower alkylene-aryl, a cycloalkyl, an aryl, -(4- to 12-membered monocyclic or bicyclic heterocycle containing 1 to 4 atoms of one or more kinds of heteroatoms selected from the group consisting of N, S, and O), —O-(4- to 12-membered monocyclic or bicyclic heterocycle containing 1 to 4 atoms of one or more kinds of heteroatoms selected from the group consisting of N, S, and O), -lower alkylene-(4- to 12-membered monocyclic or bicyclic heterocycle containing 1 to 4 atoms of one or more kinds of heteroatoms selected from the group consisting of N, S, and O), —C(=O)-(4- to 12-membered monocyclic or bicyclic heterocycle containing 1 to 4 atoms of one or more kinds of heteroatoms selected from the group consisting of N, S, and O), -lower alkylene-N(lower alkyl)-(4- to 12-membered monocyclic or bicyclic heterocycle containing 1 to 4 atoms of one or more kinds of heteroatoms selected from the group consisting of N, S, and O), or —C(=O)—NH-(4- to 12-membered monocyclic or bicyclic heterocycle containing 1 to 4 atoms of one or more kinds of heteroatoms selected from the group consisting of N, S, and O), and the above monocyclic or bicyclic heterocycle may be substituted by halogen atom(s), lower alkyl(s), —O-lower alkyl, or —OH.

[5a] The compound according to the above [5], wherein $R^{11a}$ is a lower alkyl and $R^{12a}$ is a group selected from -lower alkylene-O-lower alkyl, -lower alkylene-S-lower alkyl, -lower alkylene-NH-lower alkyl, -lower alkylene-N(lower alkyl)$_2$, -lower alkylene-OH, -lower alkylene-C(=O)—NH-lower alkyl, -lower alkylene-C(=O)—N(lower alkyl)$_2$, -lower alkylene-aryl, a cycloalkyl, an aryl, -(4- to 12-membered monocyclic or bicyclic heterocycle containing 1 to 4 atoms of one or more kinds of heteroatoms selected from the group consisting of N, S, and O), and -lower alkylene-(4- to 12-membered monocyclic or bicyclic heterocycle containing 1 to 4 atoms of one or more kinds of heteroatoms selected from the group consisting of N, S, and O).

[5b] More preferably the compound according to the above [5], wherein the ring represented by D in the above formula (I) is a ring selected from benzothiazole, quinoline, isoquinoline, indoline, tetrahydroquinoline, tetrahydroisoquinoline, 3,4-dihydro-2H-1,4-benzoxazine, dihydroquinoline, and dihydroisoquinoline.

[5c] More preferably, the compound according to the above [5], more preferably the compound according to the above [5a], wherein the ring represented by D in the above formula (I) together with the groups represented by $R^6$ to $R^9$ to be bonded thereto form a group selected from the following formulae:

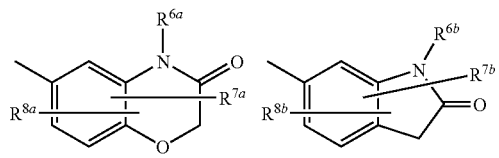

wherein the symbols have the following meanings:

$R^{6a}$ and $R^{6b}$: the same or different, a hydrogen atom, a lower alkyl, or a halogen-substituted lower alkyl, and $R^{7a}$, $R^{8a}$, $R^{7b}$, and $R^{8b}$: the same or different, a hydrogen atom, a halogen atom, a lower alkyl, or a halogen-substituted lower alkyl.

Or, the compound according to the above [5], more preferably the compound according to the above [5b], wherein the ring represented by D in the above formula (I) together with the groups represented by $R^6$ to $R^9$ to be bonded thereto form a group selected from the following formulae:

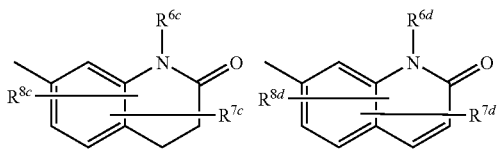

wherein the symbols have the following meanings:

$R^{6c}$ and $R^{6d}$: the same or different, a hydrogen atom, a lower alkyl, or a halogen-substituted lower alkyl, and $R^{7c}$, $R^{8c}$, $R^{7d}$, and $R^{8d}$: the same or different, a hydrogen atom, a halogen atom, a lower alkyl, or a halogen-substituted lower alkyl.

[6] The compound according to the above [1], wherein $R^1$ to $R^5$ are the same or different and each is a hydrogen atom, a halogen, a halogen-substituted lower alkyl, a lower alkyl, —N(lower alkyl)$_2$, or —O-lower alkyl.

[7] The compound according to the above [1], wherein $R^6$ to $R^9$ are the same or different and each is a hydrogen atom, a halogen atom, a lower alkyl, a halogen-substituted lower alkyl, —OH, —O-lower alkyl, =O, —NH-lower alkyl, —N(lower alkyl)$_2$, —CN, —C(=O)—NH$_2$, —NH—SO$_2$-lower alkyl, —SO$_2$—NH$_2$, —C(=O)-lower alkyl, —NO$_2$, or a nitrogen-containing saturated heterocycle, more preferably, a hydrogen atom, a halogen, a halogen-substituted lower alkyl, a lower alkyl, —OH, =O, —N(lower alkyl)$_2$, or —SO$_2$—NH$_2$. Further preferably, the compound according to the above [1], wherein $R^6$ to $R^8$ are the same or different and each is a hydrogen atom, a halogen atom, a lower alkyl, or a halogen-substituted lower alkyl and $R^9$ is =O.

[8] The compound according to the above [1], wherein $R^{10}$ in the above formula (I) is a hydrogen atom.

[9] The compound according to the above [1], wherein the group represented by L is methylene or ethylene, more preferably methylene.

[10] The compound according to the above [1] or a salt thereof, wherein the benzamide derivative represented by the above formula (I) is at least one compound selected from the group consisting of N-1,3-benzothiazol-5-yl-2-{[cyclohexyl (isopropyl)amino]methyl}biphenyl-4-carboxamide, N-(1-methyl-2-oxo-1,2,3,4-tetrahydroquinolin-7-yl)-2-(piperidin-1-ylmethyl)biphenyl-4-carboxamide, N-(3,3-dimethyl-2-oxo-2,3-dihydro-1H-indol-6-yl)-2-(piperidin-1-ylmethyl)biphenyl-4-carboxamide, 2-{[ethyl(2-hydroxy-2-methylpropyl)amino]methyl}-N-(2-methyl-3-oxo-3,4-dihydro-2H-1,4-benzoxazin-6-yl)biphenyl-4-carboxamide, N-(1-methyl-2-oxo-1,2-dihydroquinolin-7-yl)-2-(piperidin-1-ylmethyl)biphenyl-4-carboxamide, N-(3-methyl-2-oxo-1,2-dihydroquinolin-7-yl)-2-(piperidin-1-ylmethyl)biphenyl-4-carboxamide, N-(2,4-dimethyl-3-oxo-3,4-dihydro-2H-1,4-benzoxazin-6-yl)-2-(piperidin-1-ylmethyl)biphenyl-4-carboxamide, 2-{[ethyl(tetrahydro-2H-pyran-4-yl)amino]methyl}-N-(1-methyl-2-oxo-1,2,3,4-tetrahydroquinolin-7-yl)biphenyl-4-carboxamide, N-(1-methyl-2-oxo-1,2,3,4-tetrahydroquinolin-7-yl)-3-(piperidin-1-ylmethyl)-4-(2-thienyl)benzamide, 2-{[ethyl(tetrahydro-2H-thiopyran-4-yl)amino]methyl}-N-(1-methyl-2-oxo-1,2,3,4-tetrahydroquinolin-7-yl)biphenyl-4-carboxamide, 2-{[isobutyl(2-piperidin-1-ylethyl)amino]methyl}-N-(2-methyl-3-oxo-3,4-dihydro-2H-1,4-benzoxazin-6-yl)biphenyl-4-carboxamide, N,N-diethyl-4-[(4-{[(1-methyl-2-oxo-1,2,3,4-tetrahydroquinolin-7-yl)amino]carbonyl}biphenyl-2-yl)methyl]morpholine-3-carboxamide, and 2-[(4-methyl-1,3'-bipiperidin-1'-yl)methyl]-N-(2-methyl-3-oxo-3,4-dihydro-2H-1,4-benzoxazine-6-yl)biphenyl-4-carboxamide.

Moreover, the invention relates to a pharmaceutical composition comprising a benzamide derivative represented by the above formula (I) or a salt thereof and pharmaceutically acceptable carrier. Preferably, it is the aforementioned pharmaceutical composition, which is a VR1 activation inhibitor and more preferably, it is the aforementioned pharmaceutical composition, which is a preventive or therapeutic agent for pains.

Furthermore, the other embodiments include use of a benzamide derivative represented by the general formula (I) according to [1] to [10] or a salt thereof for manufacturing a preventive or therapeutic agent for pains and a method for preventing or treating pain, comprising administering an effective amount of a benzamide derivative represented by the general formula (I) according to [1] to [10] or a salt thereof.

The following will describe the invention in detail.

The "capsaicin receptor VR1 activation inhibitor" herein is a generic name of both compounds (VR1 antagonist) which bind to the VR1 receptor and inhibit VR1 activation by competition with an endogenous ligand and compounds (VR1 agonist) which desensitize nerves where the receptor is present and inhibit their subsequent activation by continuous activation of the VR1 receptor. As the "VR1 activation inhibitor", a VR1 antagonist is preferable.

In the definition of the general formulae herein, the term "lower" means a linear or branched carbon chain having from 1 to 6 carbon atoms, unless otherwise specified. Therefore, the "lower alkyl" is preferably alkyl having 1 to 5 carbon atoms, and particularly preferred are methyl, ethyl, propyl, isopropyl, butyl, isobutyl, and 1,2-dimethylpropyl. As the "lower alkylene", preferred are linear alkylenes such as methylene, ethylene, propylene, and butylene, and branched alkylenes such as methylmethylene. Particularly preferred are methylene and ethylene.

The "halogen atom" includes fluorine, chlorine, bromine, and iodine atoms. Particularly, a fluorine atom and a chlorine atom are preferred. The "halogen-substituted lower alkyl" means a group wherein the above lower alkyl is substituted by 1 to 3 halogens which are the same or different. Particularly, trifluoromethyl is preferred.

As the "monocyclic or bicyclic hydrocarbon ring", there may be mentioned benzene, naphthalene, cycloalkyl rings having 3 to 8 ring members, cycloalkenyl rings having 4 to 8 ring members, and saturated hydrocarbon ring-condensed aryl rings wherein a cycloalkyl or a cycloalkenyl ring is fused to benzene. Preferred are benzene, naphthalene, indane, and tetrahydronaphthalene.

The "aryl" is an aryl having 6 to 14 carbon atoms, and is further preferably phenyl or naphthyl.

The "cycloalkyl" is preferably a cycloalkyl group having 3 to 10 carbon atoms which may possess brige(s), and further preferred are cyclopropyl, cyclopentyl, cyclohexyl, cycloheptyl, and adamantyl groups.

The "nitrogen-containing saturated heterocycle" is a 5- to 8-membered saturated or partially unsaturated monocyclic heterocycle which contains one N atom and may further contain one heteroatom selected from N, S, and O, and preferred are pyrrolidine, piperidine, piperazine, azepane, diazepane, morpholine, thiomorpholine, and tetrahydropyridine rings.

The "5- to 12-membered monocyclic or bicyclic heteroaromatic ring containing 1 to 4 atoms of one or more kinds of heteroatoms selected from the group consisting of N, S, and O" is a 5- to 6-membered monocyclic heteroaromatic ring containing 1 to 4 atoms of heteroatoms selected from the group consisting of N, S, and O and a bicyclic heteroaryl group wherein this monocyclic heteroaromatic ring is condensed with a benzene ring or a 5- to 6-membered monocyclic heteroaromatic ring. These rings may be partially saturated. Moreover, in the case that an N atom or an S atom is included in the ring atoms, the atom may form an oxide or a dioxide. As the 5- to 6-membered monocyclic heteroaromatic ring, preferred are pyridine, pyrimidine, pyrazine, pyridazine, triazine, pyrrole, furan, thiophene, thiazole, imidazole, oxazole, isothiazole, pyrazole, isozazole, thiadiazole, triazole, and tetrazole rings. As the bicyclic heterocycle, preferred are benzothiazole, benzoisothiazole, benzoxazole, benzisoxazole, benzimidazole, benzotriazole, benzothiadiazole, benzoxadiazole, quinoline, isoquinoline, naphthylidine, quinoxaline, quinazoline, phthalazine, cinnoline, indole, indazole, imidazopyridine, benzothiophene, benzothiophene-1,1-dioxide, benzofuran, dihydrobenzofuran, dihydro-1,3-benzoxazole, dihydro-1,3-benzothiazole, 1,3-benzodioxole, benzazepine, benzodiazepine, benzoxazine, tetrahydrobenzoxazepine, tetrahydrobenzazepine, tetrahydroquinoline, tetrahydroisoquinoline, tetrahydronaphthopyridine, tetrahydroquinoxaline, chroman, dihydrobenzodioxine, 3,4-dihydro-2H-1,4-benzothiazine, dihydrobenzothiazole, 3,4-dihydro-2H-1,4-benzoxazine, isochroman, indoline, and pteridine rings. Further preferred are pyridine, benzothiazole, benzoxazole, quinoline, isoquinoline, dihydroquinoline, dihydroisoquinoline, indoline, tetrahydroquinoline, tetrahydroisoquinoline, benzothiophene, 3,4-dihydro-2H-1,4-benzoxazine, 3,4-dihydro-2H-1,4-benzothiazine, and dihydro-1,3-benzoxazole rings.

The "4- to 12-membered monocyclic or bicyclic heterocycle containing 1 to 4 atoms of one or more kinds of heteroatoms selected from the group consisting of N, S, and O" is, in addition to the above monocyclic or bicyclic heteroaromatic rings, a 4- to 8-membered saturated or partially unsaturated monocyclic heterocycle, and a bicyclic heterocycle obtained by condensing it with a cycloalkyl ring, a cycloalkenyl ring, or a saturated or partially unsaturated monocyclic heterocycle. Preferred are saturated or partially unsaturated monocyclic heterocycles such as pyrrolidine, imidazolidine, pyrazolidine, quinuclidine, piperidine, piperazine, morpholine, thiomorpholine, thiomorpholine 1,1-dioxide, azepane, azocane, 1,4-ozazepane, azetidine, 1,2,3,6-tetrahydropyridine, and imidazoline, and saturated or partially unsaturated bicyclic heterocycles such as decahydroquinoline and decahydroisoquinoline. More preferred are nitrogen-containing saturated heterocycles and further preferred are pyrrolidine, piperidine, piperazine, and morpholine rings.

In the case that the substituent is described as $R^{7a}$ or $R^{8a}$ in the following formula, it shows that the substituent may be bonded to a carbon atom on any of left and right rings.

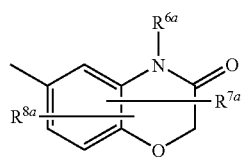

Moreover, among the compounds of the invention, there exist geometrical isomers, tautomers, and optical isomers depending on the kind of substituents. The invention encompasses mixtures of such isomers and those isolated.

The compounds of the invention form acid addition salts in some cases. Also, they form salts with bases in some cases. Specifically, such salts include addition salts with inorganic acids such as hydrochloric acid, hydrobromic acid, hydroiodic acid, sulfuric acid, nitric acid, and phosphoric acid; or with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, and glutamic acid; the salts with inorganic bases such as sodium, potassium, magnesium, calcium, and aluminum; with organic bases such as methylamine, ethylamine, ethanolamine, lysine and ornithine; ammonium salts; and the like.

Furthermore, the invention encompasses hydrates of the compounds of the invention, pharmaceutically acceptable various solvates, compounds having crystalline polymorphism, and the like.

The compounds of the invention also include compounds which are metabolized in a living body to be converted into the compound represented by the above general formula (I) or salts thereof, so-called prodrugs. The groups that form the prodrugs of the compounds of the invention are groups described in Prog. Med. 5:2157-2161 (1985) and groups described in "Iyakuhinn no Kaihatsu (Development of Medicines) published by Hirokawa Shoten, 1990, Vol. 7, Bunshi Sekkei (Molecular Design), pp. 163-198.

(Production Methods)

The following will describe representative methods of the compounds of the invention.

In this connection, in the following production process, depending on the kind of functional groups, it is sometimes technically effective to replace the functional groups to suitable protective groups at a stage of starting materials or intermediates, i.e., groups easily convertible into the functional groups. Thereafter, the protective groups can be removed to obtain desired compound when required. As such functional groups, there may be, for example, an amino group, a hydroxyl group, a carboxyl group, and the like. As such protective groups, there can be mentioned protective groups described in Protective Groups in Organic Synthesis 3rd edition (written by T. W. Green and P. G. M. Wuts, published by JOHN WILLY & SONS, INC), which may be suitably used depending on the reaction conditions. The method described in said reference can be applicable to introduction and removal of the protective groups.

(Production Method 1)

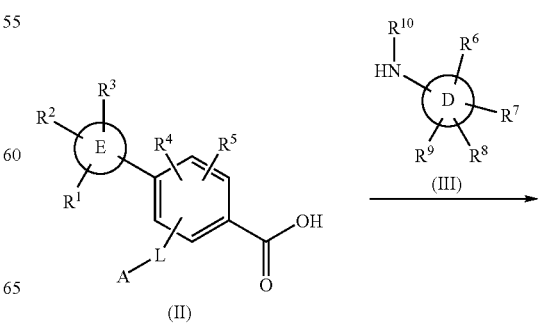

-continued

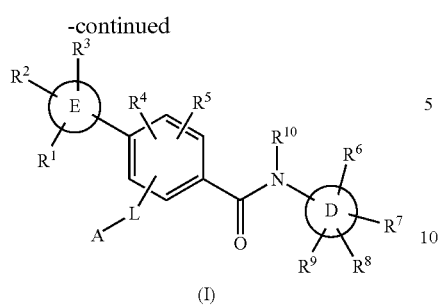

(I)

The production method 1 is a reaction of synthesizing a compound (I) by a condensation reaction of a carboxylic acid with an amine using a compound (II) and a compound (III).

The present reaction may be carried out according to a usual method using the compound (II) and the amine derivative (III) in equimolar amounts or in an excess of one of them in the presence of a condensing agent. As the condensing agent, there can be suitably used N,N-dicyclohexylcarbodiimide (DCC), 1-ethyl-3-[3-(N,N-dimethylamino)propyl]carbodiimide, O-benzotriazol-1-yl-N,N,N',N'-tetramethyluronium hexafluorophosphate (HBTU), carbonyldiimidazole, diphenylphosphoryl azide (DPPA), diethylphosphoryl cyanide, or the like. These condensing agents are used in an equimolar amount or in an excess amount of carboxylic acid. As a solvent, there can be used a solvent which does not participate in the reaction, N,N-dimethylformamide (DMF), dioxane, tetrahydrofuran, ether, dichloroethane, dichloromethane, chloroform, carbon tetrachloride, dimethoxymethane, dimethoxyethane, ethyl acetate, benzene, acetonitrile, dimethyl sulfoxide, or a mixed solvent thereof, and the solvent is suitably selected according to the applying method. Moreover, depending on the applying method, there is a case that the reaction easily proceeds by carrying out the reaction in the presence of a base such as N-methylmorpholine, triethylamine, trimethylamine, pyridine, or 4-dimethylaminopyridine or using the base as a solvent. Usually, the above reaction is carried out under cooling to under room temperature but it is sometimes preferred that the reaction is carried out under an elevated temperature depending on the kind of acylation reaction.

Moreover, the compound (I) can be also produced by the method of introducing a carboxylic acid into an active derivative and then condensing the resulting product with an amine. In this case, the reaction is carried out using the compound (II) and the amine derivative (III) in equimolar amounts or in an excess of one of them. As the active derivative of the carboxylic acid, there may be mentioned an active ester obtained by reacting the acid with a phenolic compound such as p-nitrophenol or an N-hydroxyamine compound such as 1-hydroxysuccinimide or 1-hydroxybenzotriazole, a monoalkylcarbonate, a mixed anhydride obtained by reacting it with an organic acid, a phosphate type mixed anhydride obtained by reacting it with diphenylphosphoryl chloride and N-methylmorpholine, an acid azide obtained by successively reacting an ester with hydrazine and alkyl nitrite, an acid halide such as an acid chloride or an acid bromide, and a symmetric acid anhydride. The reaction is carried out using an activation reagent in an equimolar amount to the compound (II) or in an excess thereof relative to the compound. The reaction conditions in this case are also the same as those in the case using the condensing agent.

Moreover, other than the reactions described above, any reactions can be used as far as they form amide bonds.

(Production Method 2)

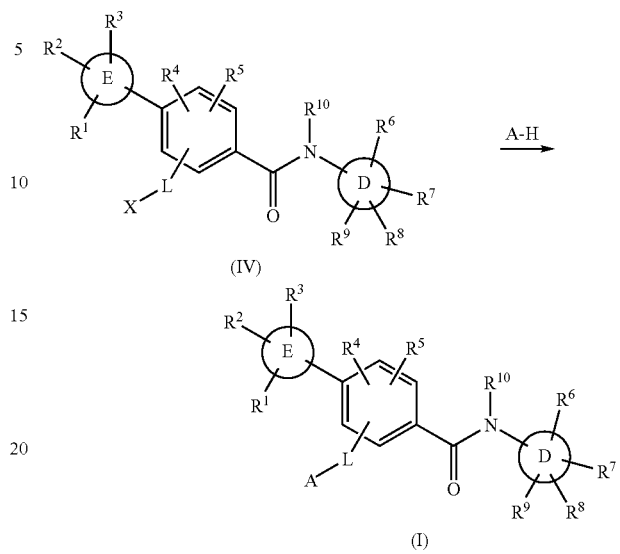

wherein X means a leaving group such as —Cl, —Br, —I, methanesulfonyloxy, or toluenesulfonyloxy, and the same shall apply hereinafter.

The production method 2 is a reaction of synthesizing the compound (I) by a nucleophilic substitution reaction using a compound (IV) and an amine compound A-H.

The present reaction is carried out using the compound (IV) and A-H in equimolar amounts or in an excess of one of them under ice cooling to under an elevated temperature by adding a base (preferably, potassium carbonate, sodium carbonate, sodium hydrogen carbonate, potassium tert-butoxide, triethylamine, pyridine, N-methylmorpholine, sodium hydroxide) using the solvent described in the production method 1 as a solvent.

In the case that the compounds (I) of the invention have various side chains and functional groups, these compounds can be easily synthesized using the compounds of the invention or production intermediates thereof as starting materials by means of reactions obvious for those skilled in the art or modified method thereof. As such examples, there may be mentioned conversion of any of $R^1$ to $R^9$ of the compound (I) obtained by the production method 1 or conversion of newly introducing it. For example, the following reactions can be applied.

The compound wherein any substituent of $R^1$ to $R^9$ in the formula (I) is —$SO_2$—$NH_2$ or CO—$NH_2$ can be produced using a compound wherein each of the corresponding $R^1$ to $R^9$ is —$SO_3H$ or $CO_2H$. The reaction is carried out by condensing —$SO_3H$ or $CO_2H$ of $R^1$ to $R^9$ with ammonia under the same conditions as those in the first production reaction.

Moreover, the compound wherein the D ring in the formula (I) is a saturated ring and any substituent of $R^1$ to $R^9$ in the formula (I) is —OH can be produced using a compound wherein the present substituent is a carbonyl group by applying a usual method for a reduction reaction. For example, the reaction can be carried out with referring to the method described in Tetrahedron, 35, 567-607 (1979).

Furthermore, the compound wherein the D ring or the E ring is a heterocycle and a heteroatom in the ring is oxidized into an oxide can be synthesized by oxidizing the heteroatom using a usual method for the oxidation reaction. The reaction can be carried out with referring to the method described in *J. Hetrocycl. Chem.* 19, 237-240, (1982), *J. Chem. Soc. Perkin Trans.* 1, 1949-1955, (1984).

(Production Method of Starting Materials)

The following will describe representative production methods for the starting materials described in the production method 1 and the production method 2.

(1) Starting Compound (II)

The first step to the eleventh step show production steps for producing the starting material (II) in the production method 1.

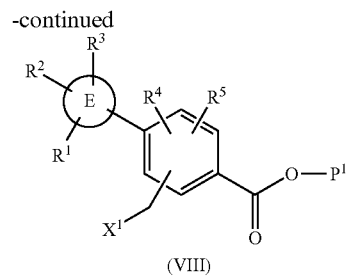

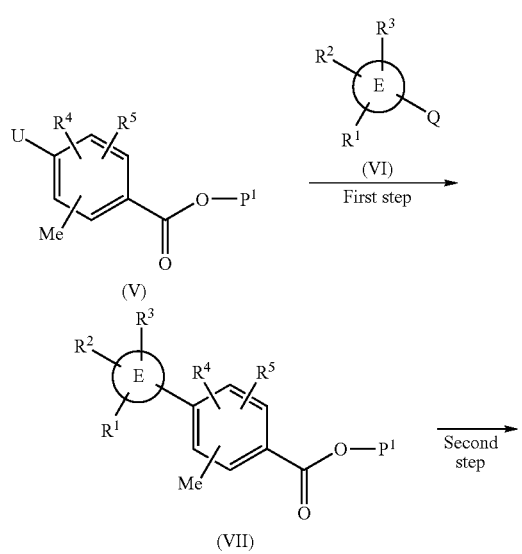

wherein any one of U and Q is —Br, —Cl, —I, or —O—SO$_2$—CF$_3$ and another one means —B(OH)$_2$ or —B(O-lower alkyl)$_2$, P$^1$ means a protective group of carboxyl, such as a methyl group, an ethyl group, a benzyl group, or a tert-butyl group and X$^1$ means —Cl, —Br, or —I, and the same shall apply hereinafter.

First, the first step is a step of producing a compound (VII) by a cross-coupling reaction using a compound (V) and a compound (VI). The reaction can be carried out with referring to the method described in *Synth. Commun.*, 11, 513-519 (1981), *Synlett* 2000, No. 6, 829-831, and *Chem. lett.*, 1989, 1405-1408.

The second step is a step of producing (VIII) by treating the compound (VII) with a halogenating agent. The reaction is carried out under room temperature to under reflux with heating using N-bromosuccinimide (NBS), bromine, sulfuryl chloride, or copper bromide as a halogenating agent in a solvent such as carbon tetrachloride, chloroform, or benzene, with adding benzoyl peroxide, 2,2'-azobisisobutyronitrile, tert-butyl hydroperoxide, or tetrakistriphenylphosphine palladium or under irradiation with light, if necessary.

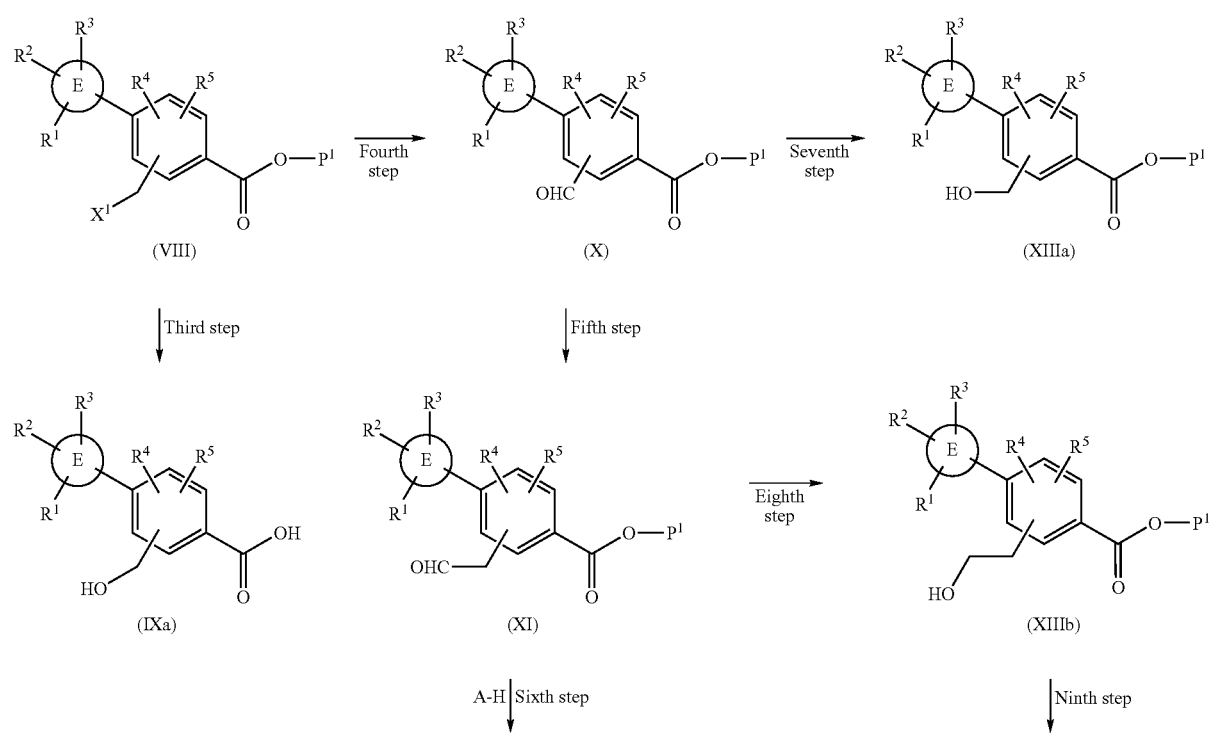

-continued

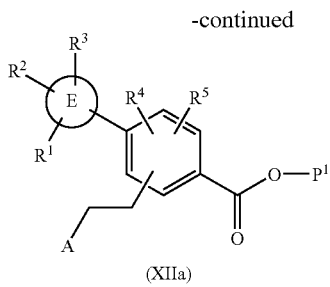

(XIIa)

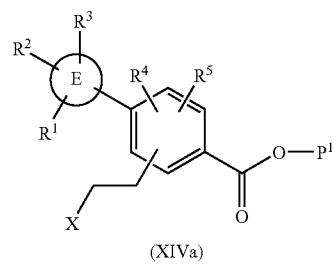

(XIVa)

The third step is a step of producing a compound (IXa) by removing the protective group $P^1$ of the compound (VIII) and simultaneously hydrolyzing the $X^1$ group. The present reaction may be carried out following a usual method for basic hydrolysis of halides. However, in the case that the protective group is not deprotected by hydrolysis with a base, after the hydrolysis of the $X^1$ group of the compound (VIII), the deprotection reaction may be carried out by hydrolysis with an acid such as hydrochloric acid or trifluoroacetic acid or by reduction such as catalytic hydrogenation. The reaction conditions may be used according to the aforementioned "Protective Groups in Organic Synthesis".

The fourth step is a step of producing a compound (X) by an oxidation reaction of the compound (VIII). The reaction is carried out using an oxidizing agent such as N-methylmorpholine-N-oxide, trimethylamine-N-oxide, sodium salt of 2-nitropropane described in *J. Am. Chem. Soc.*, 71, 1767-1769 (1949), or silver nitrate, in a solvent such as acetonitrile or ethanol under ice cooling to under reflux.

The fifth step is a step of producing a compound (XI) from the compound (X). The reaction is carried out using (methoxymethyl)triphenylphosphonium chloride, (methoxymethyl)triphenylphosphonium bromide, or the like as a reacting agent in the presence of a base such as n-butyllithium, sec-butyllithium, sodium hydride, or potassium tert-butoxide in a solvent such as tetrahydrofuran, diethyl ether, or cyclopentyl methyl ether under −78° C. to under an elevated temperature.

The sixth step is a step of producing a compound (XIIa) by condensing the compound (XI) with A-H by a reductive amination reaction. The reaction is carried out using sodium triacetoxyborohydride, sodium borohydride, or the like as a reducing agent, with adding an organic acid (preferably, acetic acid, formic acid, or p-toluenesulfonic acid), a Lewis acid such as a metal salt (preferably, tetraisopropoxytitanium), if necessary. The reaction is carried out using a solvent such as dichloromethane, dichloroethane, chloroform, carbon tetrachloride, or tetrahydrofuran under ice cooling to under an elevated temperature.

The seventh step and the eighth step are steps of producing compounds (XIIIa) and (XIIIb) by reducing the formyl group of the compounds (X) and (XI), respectively. The reaction can be carried out with referring to the method described in *Tetrahedron*, 35, 567-607 (1979).

The ninth step is a step of producing a compound (XIVa) by halogenating the hydroxyl group of the compound (XIIIb) or by converting it into a sulfonate ester. The halogenation is carried out using an acid halide (preferably, thionyl chloride, phosphorus trichloride, phosphorus pentachloride, phosphorus oxychloride, or phosphorus tribromide, etc.) or using triphenylphosphine and carbon tetrachloride, triphenylphosphine and carbon tetrabromide, or the like. The conversion into a sulfonate ester is carried out by treating it with methanesulfonyl chloride or p-toluenesulfonyl chloride in the presence of a base (preferably, triethylamine, pyridine, or potassium carbonate). It is carried out using dichloroethane, methylene chloride, chloroform, dioxane, or hexane as a solvent under ice cooling to under reflux with heating. Moreover, by treating the resulting chloride, bromide, or sulfate ester with sodium iodide, potassium iodide, or the like, an iodide can be also obtained. As a solvent in this case, acetone, 2-butanone, ethanol, or the like is used.

By applying the same reaction conditions as those of the ninth step to the compound (XIIIa), the hydroxyl group of the compound (XIIIa) can be halogenated or converted into a sulfonate ester.

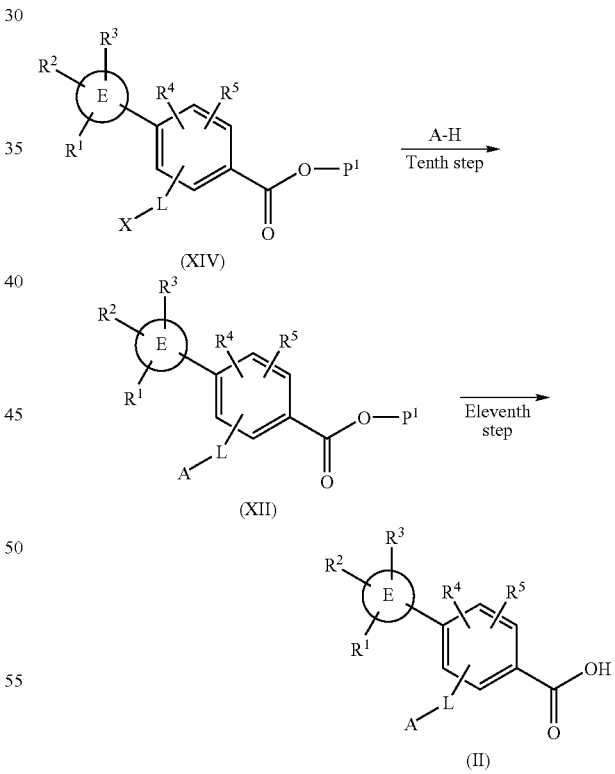

The tenth step is a step of producing a compound (XII) by reacting the compound (VIV) with A-H. The reaction is carried out under the same conditions as those of the production method 2.

The eleventh step is a step of producing the compound (II) by removing the protective group $P^1$ of the compound (XII). The deprotection reaction may be preferably carried out using procedures described in the aforementioned "Protective Groups in Organic Synthesis".

(2) Starting Compound (IV)

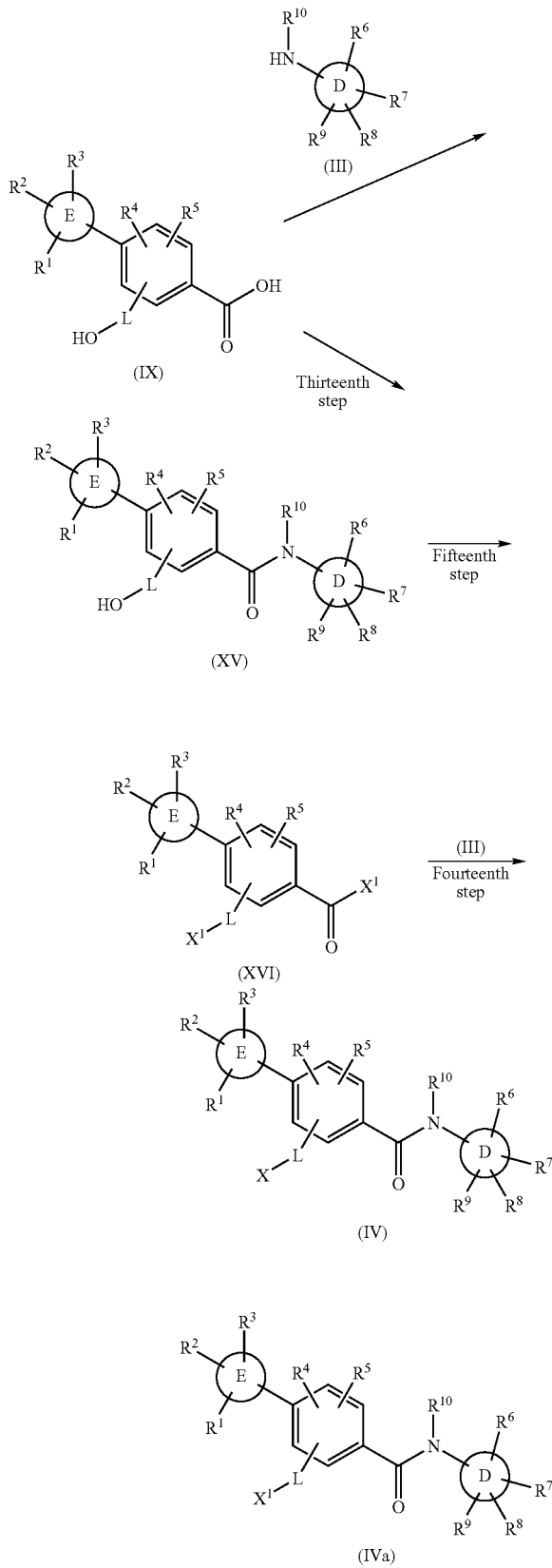

The twelfth to fifteenth steps show how to produce the starting compound (IV) in the production method 2.

First, the compound (IV) can be produced by sequentially carrying out the twelfth and fifteenth steps. The reaction can be carried out by condensing the compound (IX) and the compound (III) in the same manner as in the production method 1 and then halogenating the hydroxyl group of the resulting compound (XV) or by converting it into a sulfonate ester as in the ninth step.

Moreover, it is possible to produce a compound in the formula (IV) wherein X is restricted to $X^1$, namely a compound (IVa) via the thirteenth step and the fourteenth step. Namely, by treating the compound (IX) under the halogenation reaction conditions according to the ninth step, halogenation of the hydroxyl group and conversion of the carboxyl group into an acid halide are simultaneously carried out and an amide bond may be formed by reacting the resulting acid halide (XVI) with the amine derivative (III) separately prepared. The reaction is carried out in dichloroethane, methylene chloride, or the like in the presence of a base (pyridine, triethylamine, potassium carbonate, or sodium hydrogen carbonate) under cooling to under room temperature but under an elevated temperature depending on the kind of acyl reactions.

Furthermore, it is also possible to synthesize the compound (IV) by removing the protective group $P^1$ of the compound (XIV) and condensing the resulting carboxylic acid with the amine compound (III) under the same conditions as those of the production method 1.

The compounds of the invention thus produced may be isolated and purified, as free compounds or their salts, by applying usual chemical operations such as extraction, precipitation, fractional chromatography, fractional crystallization, and recrystallization. Salts of the compounds can be produced by treating the free compounds to an ordinary salt formation.

Moreover, in the case that the compound of the invention has an asymmetric carbon, optical isomers are present. These optical isomers can be produced by methods of leading them to diastereomeric salts with an optically active acid or base, followed by fractional crystallization, optical resolution by a usual method such as column chromatography, or synthesis using an optically active starting material.

BEST MODE FOR CARRYING OUT THE INVENTION

Examples

The following will explain the process for producing the compound of the invention specifically with reference to the following Examples. In this connection, processes for producing starting materials are shown as Reference Examples.

Reference Example 1

Into 150 ml of water were suspended 55.9 g of sodium carbonate and 38.6 g of phenylboronic acid. Thereto was added 51.4 g of ethyl 4-bromo-3-methylbenzoate dissolved in 400 ml of toluene and then was added 4.0 g of tetrakistriphenylphosphine palladium, followed by 2 hours of reflux with heating. After the reaction solution was cooled to room temperature, filtration was conducted using celite, water was added to the filtrate and the organic layer was extracted with toluene. After the organic layer was dried over anhydrous magnesium sulfate, the solvent was removed by evaporation and the resulting residue was purified by silica gel column chromatography (hexane:ethyl acetate) to obtain 50.4 g of ethyl 2-methylbiphenyl-4-carboxylate as a colorless oil.

Reference Example 2

In 130 ml of carbon tetrachloride was dissolved 10 g of 2-methylbiphenyl-4-carboxylate, the whole was heated to 90° C. and then 1.0 g of NBS and 136 mg of 2,2'-azobisisobutyronitrile were added thereto. After the reaction solution was heated under reflux, 6.78 g of NBS was added thereto and the whole was heated under reflux for 1 hour and a half. After the reaction solution was cooled to room temperature, precipitate was removed by filtration, water was added to the filtrate, and the organic layer was extracted with carbon tetrachloride. After the resulting organic layer was dried over anhydrous magnesium sulfate, the solvent was removed by evaporation to obtain 13.6 g of ethyl 2-(bromoethyl)biphenyl-4-carboxylate as a white solid.

Reference Example 3

In 50 ml of DMF was dissolved 13.6 g of ethyl 2-(bromoethyl)biphenyl-4-carboxylate, and then a suspension of 50 ml of DMF, 6.2 ml of piperidine, and 9.2 g of potassium carbonate were added thereto under ice cooling, followed by 3 hours of stirring at room temperature. Water was added to the reaction solution, the whole was extracted with ethyl acetate, and the resulting organic layer was dried over anhydrous magnesium sulfate, followed by removal of the solvent by evaporation. The obtained residue was purified by silica gel column chromatography (chloroform:methanol:aqueous ammonia) to obtain 12.6 g of ethyl 2-(piperidin-1-ylmethyl)biphenyl-4-carboxylate as a pale yellow oil.

Reference Examples 4 to 16

The compounds of Reference Examples 4 to 16 shown in the following Table were obtained in the same manner as in Reference Example 3.

Reference Example 17

In 150 ml of ethanol was dissolved 11 g of ethyl 2-(piperidin-1-ylmethyl)biphenyl-4-carboxylate, and then 51 ml of a 1M aqueous sodium hydroxide was added thereto under ice cooling, followed by 10 hours of stirring at room temperature. Under ice cooling, 51 ml of a 1M aqueous hydrochloric acid was added to the reaction solution and then the solvent was removed by evaporation to obtain 12.6 g of a pale pink solid which was a mixture of 2-(piperidin-1-ylmethyl)biphenyl-4-carboxylic acid and 1.5 equivalents of sodium chloride.

Reference Examples 18 to 40

The compounds of Reference Examples 18 to 30 shown in the following Tables were obtained in the same manner as in Reference Example 17.
The compounds of Reference Examples 31 to 35 shown in the following Table were obtained in the same manner as in Reference Example 3.
The compounds of Reference Examples 36 to 40 shown in the following Table were obtained in the same manner as in Reference Example 17.

Reference Example 41

In 100 ml of acetonitrile was dissolved 9.3 g of ethyl 2-(bromomethyl)biphenyl-4-carboxylate, and 7.0 g of N-methylmorpholine-N-oxide was added thereto at room temperature, followed by 4 hours of stirring. Water was added to the reaction solution, which was then extracted with ethyl acetate. The resulting organic layer was dried over anhydrous magnesium sulfate. After the solvent was removed by evaporation, the obtained residue was purified by silica gel column chromatography (hexane:ethyl acetate) to obtain 4.94 g of ethyl 2-formylbiphenyl-4-carboxylate as a white solid.

Reference Example 42

A suspension of 17.1 g of (methoxymethyl)triphenylphosphonium chloride in 150 ml of tetrahydrofuran was cooled to −78° C. and a 1.59M hexane solution of n-butyllithium was added dropwise to the suspension, followed by 30 minutes of stirring. Further, after the reaction solution was warmed to −40° C. and stirred for 10 minutes, it was again cooled to −78° C. and 4.2 g of ethyl 2-formylbiphenyl-4-carboxylate dissolved in 20 ml of tetrahydrofuran was added dropwise over a period of 20 minutes. The reaction solution was warmed from −50° C. to 10° C. over a period of 12 hours, followed by 4 hours of stirring at room temperature. The reaction solution was subjected to removal by evaporation, and ethyl acetate and water were added to the residue, followed by separation of an organic layer. The organic layer was dried over anhydrous magnesium sulfate, the solvent was removed by evaporation, and the obtained residue was purified by silica gel column chromatography (hexane:ethyl acetate) to obtain 1.66 g of a colorless oil. The substance was dissolved in 50 ml of 1,2-dichloroethane and 25 ml of formic acid was added thereto at room temperature, followed by 51 hours of stirring. Water and ethyl acetate were added to the reaction solution, an operation for separation was conducted, and the resulting organic layer was dried over anhydrous magnesium sulfate. After the solvent was removed by evaporation, the residue was purified by silica gel column chromatography (hexane: ethyl acetate) to obtain 1.06 g of ethyl 2-(2-oxoethyl)biphenyl-4-carboxylate as a white solid.

Reference Example 43

In 20 ml of 1,2-dichloroethane was dissolved 1.06 g of ethyl 2-(2-oxoethyl)biphenyl-4-carboxylate, and then 3.95 ml of piperidine, 589 µl of acetic acid, and 1.09 g of sodium triacetoxyborohydride were added thereto, followed by 3 hours of stirring. Water and chloroform were added to the reaction solution, and the organic layer obtained by an operation of separation was dried over anhydrous magnesium sulfate, followed by removal of the solvent by evaporation. The obtained residue was purified by silica gel column chromatography (chloroform:methanol:aqueous ammonia) to obtain 1.3 g of oily ethyl 2-(piperidin-1-ylethyl)biphenyl-4-carboxylate.

Reference Example 44

The compound of Reference Example 44 shown in the following Table was obtained in the same manner as in Reference Example 17 using ethyl 2-(piperidin-1-ylethyl)biphenyl-4-carboxylate as a starting material.

Reference Examples 45 to 56

The compound of Reference Example 45 shown in the following Table was obtained in the same manner as in Reference Example 1.

The compound of Reference Example 46 shown in the following Table was obtained in the same manner as in Reference Example 2.

The compounds of Reference Examples 47 to 50 shown in the following Table were obtained in the same manner as in Reference Example 3.

The compounds of Reference Examples 51 to 56 shown in the following Table was obtained in the same manner as in Reference Example 17.

Reference Example 57

To 160 ml of 1,2-dichloroethane was added 14.71 g of 2-(hydroxymethyl)biphenyl-4-carboxylate, and thereto was added 0.5 ml of DMF and 11.75 ml of thionyl chloride. After the reaction solution was stirred for 1 hour under reflux with heating, 8 ml of thionyl chloride was added at room temperature and the whole was stirred for 3 hours under reflux with heating. After cooling to room temperature, the reaction solvent was removed by evaporation under reduced pressure and 200 ml of 1,2-dichloroethane was added to the residue. Under ice cooling, 8.07 g of 1,3-benzothiazol-5-amine and 17.4 ml of pyridine were added thereto, followed by stirring at room temperature. The reaction solvent was removed by evaporation under reduced pressure and the obtained residue was purified by silica gel column chromatography (hexane:ethyl acetate) to obtain 11.23 g of yellow foamy N-1,3-benzothiazol-5-yl-2-(chloromethyl)biphenyl-4-carboxamide.

Reference Example 58

In 50 ml of methylene chloride was dissolved 2.5 g of 6-nitroindoline, and then 6.37 ml of triethylamine was added thereto. Under ice cooling, 3.51 g of methanesulfonyl chloride was added dropwise, the reaction solution was stirred at room temperature for 3 hours, and then ice-water was added thereto, followed by 1 hour of stirring. The reaction solvent was removed by evaporation under reduced pressure, a 1M aqueous hydrochloric acid solution was added to the residue, and precipitated was filtrated off, whereby 3.52 g of 1-methylsulfonyl-6-nitroindoline was obtained as a brown solid.

Reference Example 59

In 11.5 ml of DMF was dissolved 500 mg of 6-nitro-2H-benzothiazin-3(4H)-one, and thereto was added 114 mg of sodium hydride of 55% purity under ice cooling, followed by 30 minutes of stirring at room temperature. To the reaction solution was added 444 μl of methyl iodide, and the whole was stirred at room temperature for 2 hours. To the reaction solution was added 2 ml of methanol under ice cooling, followed by 10 minutes of stirring at room temperature. Thereafter, water was added and the organic layer was extracted with ethyl acetate. The organic layer was dried over anhydrous sodium sulfate and then the solvent was removed by evaporation. The obtained residue was purified by silica gel column chromatography (chloroform) to obtain 308 mg of 4-methyl-6-nitro-2H-1,4-benzothiazin-3(4H)-one.

Reference Examples 60 and 61

The compounds of Reference Examples 60 and 61 shown in the following Table shown were obtained in the same manner as in Reference Example 59.

Reference Example 62

In 7.4 ml of tetrahydrofuran was dissolved 160 mg of 2-chloro-5-nitro-1,3-benzothiazole, and thereto was added 1.86 ml of a 1M dimethylamine tetrahydrofuran solution, followed by 16.5 hours of stirring. Water was added to the reaction solution and the organic layer was extracted with ethyl acetate. After the organic layer was dried over anhydrous sodium sulfate, the solvent was removed by evaporation. The obtained residue was purified by silica gel column chromatography (hexane:ethyl acetate) to obtain 173 mg of N,N-dimethyl-5-nitro-1,3-benzothiazol-2-amine as a yellow solid.

Reference Example 63

In 13.5 ml of a 2M dimethylamine tetrahydrofuran solution was dissolved in 2.0 g of 2,3-dichloropyridine, followed by 6 hours of stirring at 100° C. under sealed-tube conditions. After the reaction solution was cooled to room temperature, a saturated sodium bicarbonate solution was added thereto and an extraction operation was conducted with ethyl acetate. The organic layer was dried over sodium sulfate, filtration was conducted, and the filtrate was concentrated under reduced pressure to obtain 693 mg of a yellow oil. Then, 693 mg of the resulting oil was dissolved in 5 ml of concentrated sulfuric acid, and a mixed solution of 1.2 g of fuming nitric acid and 0.7 ml of concentrated sulfuric acid was slowly added. After stirred for 30 minutes under ice cooling, cold water was added to the reaction solution and then sodium carbonate was added until the solution was rendered basic. Ethyl acetate was added, the organic layer was extracted, dried over sodium sulfate, and filtrated, and the filtrate was concentrated under reduced pressure. The obtained residue was purified by silica gel column chromatography (hexane:ethyl acetate) to obtain 347 mg of 3-chloro-N-methyl-5-nitropyridin-2-amine as a yellow solid.

Reference Example 64

In 20 ml of tert-butyl alcohol was dissolved 1.4 g of 1-methyl-6-nitro-1H-indole, and then 3.5 g of N-bromosuccinimide was added as four divided portions.

After stirred at room temperature for 4 hours, the reaction solution was concentrated under reduced pressure. Water was added to the residue and the organic layer was extracted with ethyl acetate. After the organic layer was dried over anhydrous magnesium sulfate, the solvent was removed by evaporation. The obtained residue was purified by silica gel column chromatography (hexane:ethyl acetate) to obtain 2.44 g of 3,3-dibromo-1-methyl-6-nitro-1,3-dihydro-2H-indol-2-one as a yellow solid.

Reference Example 65

To 2.00 g of 1-methylsulfonyl-6-nitroindoline and a mixed solvent of 100 ml of ethanol and 100 ml of tetrahydrofuran was added 300 mg of 10% palladium/carbon under an argon atmosphere, followed by 3 hours of stirring at room temperature under a hydrogen atmosphere. The reaction solution was filtrated through celite and the organic solvent in the filtrate was removed under reduced pressure. To the residue was added 200 ml of a mixed solution of methanol, ethyl acetate, and tetrahydrofuran. Under an argon atmosphere, 1 g of 10% palladium/carbon was added and the whole was stirred at room temperature for 3 hours under a hydrogen atmosphere. The reaction solution was filtrated through celite and the organic solvent in the filtrate was removed under reduced pressure to obtain 1.66 g of 1-methylsulfonyl-6-aminoindoline as a pale yellow solid.

Reference Examples 66 to 71

The compounds of Reference Examples 66 to 71 shown in the following Table were obtained in the same manner as in Reference Example 65.

Reference Example 72

In 70 ml of toluene was dissolved 3.2 g of ethyl 4-formyl-3-nitrobenzoate and then 5.75 g of methyl triphenylphosphoranylideneacetate, followed by 6 hours of stirring under reflux. After cooling, the reaction solution was concentrated under reduced pressure and the obtained residue was purified by silica gel column chromatography (hexane:ethyl acetate) to obtain 3.63 g of ethyl 4-[(1E)-3-methoxy-3-oxoprop-1-en-1-yl]-3-nitrobenzoate as a white solid.

Reference Example 73

To a mixture of 1.8 g of ethyl 4-[(1E)-3-methoxy-3-oxoprop-1-en-1-yl]-3-nitrobenzoate, 32 ml of ethanol and 32 ml of tetrahydrofuran was added 640 mg of 10% palladium/carbon under an argon atmosphere, followed by 2 hours of stirring at room temperature under a hydrogen atmosphere. The reaction solution was filtrated through celite and the organic solvent in the filtrate was removed under reduced pressure. To the residue were added 50 ml of methanol and 2 drops of concentrated hydrochloric acid, followed by 30 minutes of stirring at 60° C. After cooling to room temperature, the reaction solution was concentrated under reduced pressure and water and chloroform were added to the residue, followed by an analytical operation. The organic layer was dried over anhydrous sodium sulfate and the solvent was removed by evaporation. The obtained residue was purified by silica gel column chromatography (hexane:ethyl acetate) to obtain 1.16 g of ethyl 2-oxo-1,2,3,4-tetrahydroquinoline-7-carboxylate as a white solid.

Reference Example 74

Into 10 ml of toluene was suspended 200 mg of 1-methyl-2-oxo-1,2,3,4-tetrahydroquinoline-7-carboxylic acid, and then 268 mg of diphenylphosphoryl azide (DPPA), 722 mg of tert-butyl alcohol, and 0.135 ml of triethylamine were added thereto, followed by 14 hours of stirring under reflux with heating. After cooling, the reaction solution was concentrated under reduced pressure, water was added to the residue, and the organic layer was extracted with ethyl acetate. After the organic layer was dried over anhydrous sodium sulfate, the solvent was removed by evaporation. To the residue was added 5 ml of a 4M ethyl acetate solution of hydrochloric acid, followed by 7 hours of stirring at room temperature. Then, the reaction solution was concentrated under reduced pressure. To the residue was added a saturated aqueous sodium hydrogen carbonate, and the organic layer was extracted with chloroform. After the organic layer was dried over anhydrous sodium sulfate, the solvent was removed by evaporation. The obtained residue was purified by silica gel column chromatography (chloroform:methanol:aqueous ammonia) to obtain 80 mg of 7-amino-1-methyl-3,4-dihydroquinolin-2(1H)-one as a white solid.

Reference Example 75

A suspension of 329 mg of 3-chloro-N-methyl-5-nitropyridin-2-ylamine, 489 mg of iron powder, and 9 ml of acetic acid was stirred at 60° C. for 2 hours. After the reaction solution was cooled to room temperature, ethanol was added thereto and the solution was filtrated through celite. The filtrate was concentrated under reduced pressure and ethyl acetate and a saturated aqueous sodium bicarbonate solution were added thereto. To the organic layer obtained by an operation of separation was added a 1M aqueous sodium hydroxide solution, followed by an operation of separation. The resulting organic layer was dried over anhydrous sodium sulfate and filtrated and then the resulting filtrate was concentrated under reduced pressure. The residue was purified by silica gel column chromatography (chloroform:methanol) to obtain 193 mg of 3-chloro-2-methylamino-5-aminopyridine as a brown oil.

Reference Examples 76 to 124

The compound of Reference Example 76 shown in the following Table was obtained in the same manner as in Reference Example 1.

The compound of Reference Example 77 shown in the following Table was obtained in the same manner as in Reference Example 2.

The compounds of Reference Examples 78 to 80 shown in the following Table were obtained in the same manner as in Reference Example 3.

The compounds of Reference Examples 81 to 83 shown in the following Table were obtained in the same manner as in Reference Example 17.

The compounds of Reference Examples 84 to 89 shown in the following Tables were obtained in the same manner as in Reference Example 1.

The compounds of Reference Examples 90 to 95 shown in the following Table were obtained in the same manner as in Reference Example 2.

The compounds of Reference Examples 96 to 124 shown in the following Tables were obtained in the same manner as in Reference Example 3.

Reference Example 125

2,4-Dinitrobenzaldehyde was dissolved in dioxane and water, methyl acrylate and triethylenediamine were added thereto at room temperature, and the whole was stirred to obtain methyl 2-[(2,4-dinitrophenyl)(hydroxy)methyl]acrylate.

Reference Examples 126 to 162

The compounds of Reference Examples 126 to 162 shown in the following Tables were obtained in the same manner as in Reference Example 17.

Reference Example 163

N-(8-Chloro-3-oxo-3,4-dihydro-2H-1,4-benzoxazin-6-yl)-2,2,2-trifluoroacetamide was hydrolyzed with sodium hydroxide to obtain 6-amino-8-chloro-2H-1,4-benzoxazin-3(4H)-one.

Reference Examples 164 to 166

The compound of Reference Example 164 shown in the following Table was obtained in the same manner as in Reference Example 41.

The compound of Reference Example 165 shown in the following Table was obtained in the same manner as in Reference Example 42.

The compound of Reference Example 166 shown in the following Table was obtained in the same manner as in Reference Example 43.

Reference Example 167

Ethyl 2-[(ethylamino)methyl]biphenyl-4-carboxylate and tetrahydro-4H-pyran-4-one were treated with sodium triacetoxyborohydride in the presence of acetic acid to obtain ethyl 2-{[ethyl(tetrahydro-2H-pyran-4-yl)amino]methyl}biphenyl-4-carboxylate.

Reference Examples 168 to 189

The compounds of Reference Examples 168 to 170 shown in the following Table were obtained using the same reagents as in Reference Example 167.

The compound of Reference Example 171 shown in the following Table was obtained in the same manner as in Reference Example 57.

The compound of Reference Example 172 shown in the following Table was obtained in the same manner as in Reference Example 58.

The compounds of Reference Examples 173 to 175 shown in the following Tables were obtained in the same manner as in Reference Example 59.

After N-alkylation was carried out in the same manner as in Reference Example 59, the compounds of Reference Examples 176 to 177 shown in the following Table were obtained by hydrolyzing the ester group in the same manner as in Reference Example 17.

The compounds of Reference Examples 178 to 179 shown in the following Table were obtained in the same manner as in Reference Example 63.

Reference Example 180

Methyl 2,6-dichloro-5-fluoronicotinate was treated with dimethylamine in a sealed tube to obtain methyl 2-chloro-6-(dimethylamino)-5-fluoronicotinate, which was then reacted under a hydrogen atmosphere in the presence of palladium/carbon to obtain methyl 6-(dimethylamino)-5-fluoronicotinate.

Reference Examples 181 to 182

The compounds of Reference Examples 181 to 182 shown in the following Tables were obtained in the same manner as in Reference Example 65.

Reference Example 183

Ethyl (2S)-2-(2,4-dinitrophenoxy)propanoate was subjected to a reduction reaction with palladium/carbon under a hydrogen atmosphere in ethanol to obtain (2S)-6-amino-2-methyl-2H-1,4-benzoxadin-3(4H)-one.

Reference Examples 184 to 186

The compound of Reference Example 184 shown in the following Table was obtained in the same manner as in Reference Example 183.

The compounds of Reference Examples 185 to 186 shown in the following Table were obtained in the same manner as in Reference Example 72.

Reference Example 187

Palladium/carbon was added to an ethanol solution of [2,4-dinitro-6-(trifluoromethyl)phenyl]malonic acid dibenzyl ester and the reaction was carried out under a hydrogen atmosphere to obtain 6-amino-4-(trifluoromethyl)-1,3-dihydro-2H-indol-2-one.

Reference Example 188

The compound of Reference Example 189 shown in the following Table was obtained in the same manner as in Reference Example 188.

Reference Example 189

Methyl 3-amino-4-(1-hydroxy-3-methoxy-2-methyl-3-oxopropyl)benzoate was treated with hydrochloric acid in 1,4-dioxane to obtain methyl 3-methyl-2-oxo-1,2-dihydroquinolin-7-carboxylate.

Reference Example 190

Methyl 4-[(1E)-3-ethoxy-2-methyl-3-oxoprop-1-en-1-yl]-3-nitrobenzoate and palladium/carbon were added to ethanol and the whole was stirred under a hydrogen atmosphere to obtain methyl 3-methyl-2-oxo-1,2,3,4-tetrahydroquinolin-7-carboxylate.

Reference Examples 191 to 198

The compounds of Reference Examples 191 to 198 shown in the following Tables were obtained in the same manner as in Reference Example 74.

Reference Example 199

Methyl 2-[(2,4-dinitrophenyl) (hydroxy)methyl]acrylate was reacted in ethanol in the presence of palladium/carbon under a hydrogen atmosphere to obtain 7-amino-3-methylquinolin-2(1H)-one.

Reference Example 200

4-(t-Butoxycarbonyl)morpholine-2-carboxylic acid and diethylamine were dissolved in DMF, 1-ethyl-3-(3'-dimethylaminopropyl)carbodiimide was added thereto at room temperature, and the whole was stirred to obtain t-butyl 2-[(diethylamino)carbonyl]morpholine-4-carboxylate.

Reference Examples 201 to 203

The compounds of Reference Examples 201 to 203 shown in the following Table were obtained in the same manner as in Reference Example 201.

Reference Example 204

N-(3-Aminophenyl)acetamide was treated with cinnamoyl chloride in the presence of a base and then the resulting N-[3-(acetylamino)phenyl]-3-phenylacrylamide was treated with aluminum chloride to obtain N-(2-oxo-1,2-dihydroquinolin-7-yl)acetamide.

Reference Example 205

N-(3-Aminophenyl)acetamide was treated with 2-nitrophenylsulfonyl chloride in the presence of triethylamine and then the resulting compound was treated with iodomethane and potassium carbonate. Thereafter, the product was treated with thioglycolic acid to obtain N-[3-(methylamino)phenyl]acetamide.

Reference Example 206

The compound of Reference Example 206 shown in the following Table was obtained in the same manner as in Reference Example 204.

Reference Example 207

A 1.2M hydrochloric acid-ethanol solution of N-(2-oxo-1,2-dihydroquinolin-7-yl)acetamide was heated under reflux to obtain 7-aminoquinolin-2(1H)-one.
The compound of Reference Example 208 shown in the following Table was obtained in the same manner as in Reference Example 207.

Reference Example 209

2-Chloro-1,5-dinitro-3-(trifluoromethyl)benzene was treated with malonic acid dibenzyl ester in the presence of sodium hydride to obtain [2,4-dinitro-6-(trifluoromethyl)phenyl]malonic acid dibenzyl ester.

Reference Example 210

The compound of Reference Example 210 shown in the following Table was obtained in the same manner as in Reference Example 209.

Reference Example 211

Ethyl 5,6-dichloronicotinate, (2,4-dimethoxybenzyl)amine hydrochloride, and triethylamine were added to chloroform and the whole was stirred at room temperature to obtain 5-chloro-6-[(2,4-dimethoxybenzyl)amino]nicotinate.

Reference Example 212

5-Chloro-6-[(2,4-dimethoxybenzyl)amino]nicotinate was treated with sodium hydroxide in ethanol to obtain 5-chloro-6-[(2,4-dimethoxybenzyl)amino]nicotinic acid. To the compound were added toluene, diphenylphosphoryl azide (DPPA), tert-butyl alcohol, and triethylamine, and the whole was stirred under reflux with heating. The resulting compound was treated with trifluoroacetic acid to obtain 3-chloropyridin-2,5-diamine.

Reference Example 213

1-Methyl-5-nitro-1H-indol-2,3-dione was treated with (diethylamino)sulfur trifluoride to obtain 3,3-difluoro-1-methyl-5-nitro-1,3-dihydro-2H-indol-2-one.

Reference Example 214

3,3-Difluoro-1-methyl-5-nitro-1,3-dihydro-2H-indol-2-one was subjected to a hydrogenation reaction using a Raney-Ni catalyst under a hydrogen stream to obtain 5-amino-3,3-difluoro-1-methyl-1,3-dihydro-2H-indol-2-one.

Reference Example 215

5-Nitro-3-(trifluoromethyl)pyridin-2(1H)-one was treated with thionyl chloride and then the resulting 2-chloro-5-nitro-3-(trifluoromethyl)pyridine was treated with dimethylamine to obtain N,N-dimethyl-5-nitro-3-(trifluoromethyl)pyridin-2-amine.

Reference Example 216

In the presence of potassium carbonate, 1-fluoro-2,4-dinitrobenzen was treated with ethyl (2S)-(−)-2-hydroxypropanoate to obtain ethyl (2S)-2-(2,4-dinitrophenyl)propionate.

Reference Example 217

The compound of Reference Example 218 shown in the following Table was obtained in the same manner as in Reference Example 217.

Reference Example 218

Trifluoroacetic anhydride was added to a mixed solution of 6-amino-2H-1,4-benzoxazin-3(4H)-one and chloroform-tetrahydrofuran to obtain 2,2,2-trifluoro-N-(3-oxo-3,4-dihydro-2H-1,4-benzoxazin-6-yl)acetamide.

Reference Example 219

2,2,2-Trifluoro-N-(3-oxo-3,4-dihydro-2H-1,4-benzoxazin-6-yl)acetamide was treated with N-chlorosuccinimide in DMF to obtain N-(8-chloro-3-oxo-3,4-dihydro-2H-1,4-benzoxazin-6-yl)-2,2,2-trifluoroacetamide.

Reference Examples 220 to 221

The compounds of Reference Examples 220 to 221 shown in the following Table were obtained in the same manner as in Reference Example 219.

Reference Example 222

Ethyl 3-chloro-4-hydroxy-5-methylbenzoate was treated with trifluoromethanesulfonyl anhydride in the presence of a base to obtain ethyl 3-chloro-5-methyl-4-{[(trifluoromethyl)sulfonyl]oxy}benzoate.

Reference Example 223

Ethyl 2-({ethyl[(2-nitrophenyl)sulfonyl]amino}methyl)biphenyl-4-carboxylate was treated with thioglycolic acid in the presence of a base to obtain ethyl 2-[(ethylamino)methyl]biphenyl-4-carboxylate.

Reference Example 224

1-Chloro-2-methylpropan-2-ol was treated with ethylamine to obtain 1-(ethylamino)-2-methylpropan-2-ol.

Reference Example 225 t-Butyl 2-[(diethylamino)carbonyl]morpholine-4-carboxylate was treated with a 4M ethyl acetate solution of hydrochloric acid in ethyl acetate to obtain N,N-diethylmorpholine-2-carboxamide hydrochloride.

Reference Examples 226 to 229

The compounds of Reference Examples 226 to 229 shown in the following Table were obtained in the same manner as in Reference Example 225.

Reference Example 230

(2R,6S)-2,6-Dimethylpiperazine was treated with di-t-butylcarbonyl to obtain 4-butoxycarbonyl-2,6-dimethylpiperazine, which was then treated with acetyl chloride in dichloromethane in the presence of triethylamine to obtain 1-acetyl-4-butoxycarbonyl-2,6-dimethylpiperazine. Thereafter, the compound was treated with hydrochloric acid to obtain (2R,6S)-1-acetyl-2,6-dimethylpiperazine.

Reference Example 231

(2-Piperidin-1-ylethyl)amine was treated with 2-methylpropanoyl chloride in the presence of triethylamine to obtain 2-methyl-N-(2-piperidin-1-ylethyl)propanamide.

Reference Example 232

The compound of Reference Example 232 shown in the following Table was obtained in the same manner as in Reference Example 231.

Reference Example 233

(2R,6S)-1-Acetyl-2,6-dimethylpiperazine was reduced with lithium aluminum hydride to obtain (2R,6S)-1-ethyl-2,6-dimethylpiperazine.

Reference Example 234

3-(Isobutylamino)propyl-2-methylpropanoate was reduced with lithium aluminum hydride to obtain N-(3-hydroxypropyl)-2-methylpropanamide.

Reference Example 235

The compound of Reference Example 235 shown in the following Table was obtained in the same manner as in Reference Example 234.

Example 1

Into 20 ml of 1,2-dichloroethane were suspended 500 mg of a mixture of 2-(piperidin-1-ylmethyl)biphenyl-4-carboxylic acid and 1.5 equivalents of sodium chloride, and then 174 mg of 3-methoxyaniline dissolved in 2 ml of 1,2-dichloroethane was added thereto. Under ice cooling, 694 mg of O-benzotriazol-1-yl-N,N,N',N'-tetramethyluronium hexafluorophosphate and 211 µl of N-methylmorpholine were added thereto, followed by 30 hours of stirring at room temperature. Water was added to the reaction solution and the organic layer was extracted with chloroform. The organic layer was dried over anhydrous magnesium sulfate, followed by removal of the solvent by evaporation. The obtained residue was purified by silica gel column chromatography (chloroform:methanol:aqueous ammonia) to obtain N-(3-methoxyphenyl)-2-(piperidin-1-ylmethyl)biphenyl-4-carboxamide. The compound was dissolved in 3 ml of ethyl acetate and then 1 ml of a 4M ethyl acetate solution of hydrochloric acid was added thereto. The solvent was removed by evaporation and crystallization was effected from ethanol to obtain 103 mg of N-(3-methoxyphenyl)-2-(piperidin-1-ylmethyl)biphenyl-4-carboxamide hydrochloride as a white powder.

Example 2

A mixture of 227 mg of 3-aminophenol, 3-(piperidin-1-ylmethyl)biphenyl-4-carboxylic acid (2.08 mmol), and sodium chloride was suspended into 7 ml of DMF and then 599 mg of 1-ethyl-3-(3'-dimethylaminopropyl)carbodiimide was added thereto at room temperature, followed by 10 hours of stirring. Ethyl acetate and a 1M aqueous hydrochloric acid solution were added to the reaction solution and sodium hydrogen carbonate was added to the aqueous layer obtained by an operation of separation until the aqueous layer was rendered basic. Ethyl acetate was added to the aqueous layer and an operation of separation was conducted. The resulting organic layer was dried over anhydrous magnesium sulfate and then the solvent was removed by evaporation. The obtained white solid was dissolved in ethanol and a 4M ethyl acetate solution of hydrochloric acid was added thereto, followed by removal of the solvent by evaporation. Ethanol and water were added to the obtained reside and crystallization was effected to obtain 436 mg of N-(3-hydroxyphenyl)-3-(piperidin-1-ylmethyl)biphenyl-4-carboxamide hydrochloride as a white powder.

Example 3 to 9

The compounds of Examples 3 to 5 shown in the following Table were obtained in the same manner as in Example 2.
The compounds of Examples 6 to 9 shown in the following Table were obtained in the same manner as in Example 1.

Example 10

To 30 ml of thionyl chloride were added 500 mg of a mixture of 2-(piperidin-1-ylmethyl)biphenyl-4-carboxylic acid and 1.5 equivalents of sodium chloride and 1 drop of DMF under ice cooling, followed by 2 hours of stirring at room temperature. The reaction solution was concentrated under reduced pressure and toluene was added to the residue, followed by concentration under reduced pressure. After the residue was dried under reduced pressure, 20 ml of methylene chloride was added. Under ice cooling, 277 mg of 3,4,5-trichloroaniline and 0.59 ml of triethylamine were added to the reaction mixture, and the whole was stirred at room temperature for 3 hours and at 40° C. overnight. The reaction mixture was concentrated under reduced pressure and the residue was purified by silica gel column chromatography (chloroform:methanol:aqueous ammonia) to obtain N-(3,4,5-trichlorophenyl)-2-(piperidin-1-ylmethyl)biphenyl-4-carboxamide. The compound was dissolved in chloroform and 1 ml of a 4M dioxane solution of hydrochloric acid was added thereto. The solvent was removed by evaporation and the resulting oil was crystallized from ether to obtain 450 mg of N-(3,4,5-trichlorophenyl)-2-(piperidin-1-ylmethyl)biphenyl-4-carboxamide hydrochloride as a white powder.

Example 11 to 99

The compound of Example 11 shown in the following Table was obtained in the same manner as in Example 10.
The compounds of Examples 12 to 43 shown in the following Tables were obtained in the same manner as in Example 1.
The compounds of Examples 44 to 99 shown in the following Tables were obtained in the same manner as in Example 10.

Example 100

To 10 ml of chloroform were added 250 mg of N-1,3-benzothiazol-5-yl-2-(chloromethyl)biphenyl-4-carboxamide and 169 mg of piperidine-4-carboxamide, followed by 3 days of stirring at room temperature. The reaction solvent was removed by evaporation under reduced pressure and the obtained residue was purified by silica gel column chromatography (chloroform:methanol) to obtain a yellow foamy substance. Thereto were added 2 ml of ethanol and 1 ml of a 4M ethyl acetate solution of hydrochloric acid, followed by removal of the solvent under reduced pressure. The residue was crystallized (ethanol:water:ethyl acetate) to obtain 205 mg of 1-({4-[(1,3-benzothiazol-5-ylamino)carbonyl]biphenyl-2-yl}methyl)piperidine-4-carboxamide hydrochloride.

Example 101 to 111

The compounds of Examples 101 to 111 shown in the following Tables were obtained in the same manner as in Example 100.

Example 112

In 5 ml of N,N-dimethylacetamide was dissolved 230 mg of N-(4-methyl-3-oxo-3,4-dihydro-2H-1,4-benzothiazin-6-yl)-2-(piperidin-1-ylmethyl)biphenyl-4-carboxamide, and then 252 mg of m-chloroperbenzoic acid was added under ice cooling, followed by 24 hours of stirring at room temperature. To the reaction solution was added 5 ml of water and 1016 mg of sodium hydrogen sulfite as two divided portions, followed by 2 hours of stirring at room temperature. Water was added to the reaction system, the organic layer was extracted with ethyl acetate and dried over anhydrous sodium sulfate, and the solvent was removed by evaporation. The obtained residue was purified by silica gel column chromatography (chloroform:methanol:aqueous ammonia) to obtain a yellow oil. It was dissolved in 5 ml of ethyl acetate and then 1 ml of a 4M ethyl acetate solution of hydrochloric acid was added thereto. The solvent was removed by evaporation and the resulting solid was recrystallized from ethanol to obtain 61 mg of N-(4-methyl-1,1-dioxo-3-oxo-3,4-dihydro-2H-1,4-benzothiazin-6-yl)-2-(piperidin-1-ylmethyl)biphenyl-4-carboxamide hydrochloride as a white powder.

Example 113

The compounds of Example 113 shown in the following Table were obtained in the same manner as in Example 10.

Example 114

Into 15 ml of methanol was suspended 250 mg of N-(3-oxo-2,3-dihydro-1H-1-inden-5-yl)-2-(piperidin-1-ylmethyl) biphenyl-4-carboxamide, and then 40 mg of sodium borohydride was added at room temperature. The reaction solution was stirred at room temperature for 1 hour and then 5 ml of water was added. The reaction solution was subjected to removal by evaporation under reduced pressure. After the obtained residue was dissolved in a mixed solution of chloroform and water, the solution was extracted with chloroform. The organic layer was dried over anhydrous sodium sulfate and then filtered, and the solvent was removed by evaporation. The obtained residue was dissolved in 10 ml of ethanol and then 0.5 ml of a 4M ethyl acetate solution of hydrochloric acid was added thereto. The solvent was removed by evaporation and the obtained residue was crystallized from ethanol to obtain 113 mg of N-(3-hydroxy-2,3-dihydro-1H-1-inden-5-yl)-2-(piperidin-1-ylmethyl)biphenyl-4-carboxamide hydrochloride as a white powder.

Example 115 to 181

The compounds of Example 115 to 121 shown in the following Tables were obtained in the same manner as in Example 1.

The compounds of Examples 122 and 123 shown in the following Table were obtained in the same manner as in Example 2.

The compounds of Examples 124 to 181 shown in the following Tables were obtained in the same manner as in Example 10.

Example 182

In 20 ml of DMF were dissolved 500 mg of 4-{[(2-methyl-3-oxo-3,4-dihydro-2H-1,4-benzoxazin-6-yl)amino] carbonyl}biphenyl-2-yl)methyl methanesulfonate, 123 mg of N-methylhexan-1-amine, 177 mg of potassium carbonate, and 212 mg of potassium iodide, followed by 3 hours of stirring at 70° C. After subjected to an analytical operation, the solvent was removed by evaporation. The obtained residue was purified by silica gel column chromatography (chloroform:methanol:aqueous ammonia) to obtain a colorless viscous substance. Ethanol and 0.4 ml of a 4M ethyl acetate solution of hydrochloric acid was added thereto and the solvent was removed by evaporation. The residue was washed (2-propanol:ethanol) to obtain 233 mg of 2-{[hexyl(methyl) amino]methyl}-N-(2-methyl-3-oxo-3,4-dihydro-2H-1,4-benzothiazin-6-yl) biphenyl-4-carboxamide hydrochloride as a white solid.

Example 183 to 196

The compounds of Example 183 to 196 shown in the following Tables were obtained in the same manner as in Example 182.

Example 197

To a 1,4-dioxane 0.7 ml solution of 19 mg of N-1,3-benzothiazol-5-yl-2-(chloromethyl)biphenyl-4-carboxamide was added a N-methyl-2-pyrrolidinone 0.1 ml solution of 12 mg of 4-(4-chlorophenyl)pyrrolidine-3-methylcarboxylate, and further 14 mg of potassium carbonate and 12 mg of potassium iodide were added, followed by 1 day of stirring at room temperature. To the filtrate obtained by filtrating the reaction solution was added 0.4 ml of ethyl acetate, extracted through a diatomaceous column containing 0.1 ml of water, and eluted with 0.4 ml of ethyl acetate. The solvent of the eluate was removed by evaporation under reduced pressure and the obtained residue was purified preparatively by HPLC (column: Symmetry (registered trademark) C18 5 μm 19 mm×100 mm, solvent: MeOH/0.1% HCOOH—H$_2$O=10/90 (0 min)-10/90 (1 min)-100/0 (9 min)-100/0 (12 min), flow rate: 30 mL/min) to obtain 0.4 mg of methyl-(3R,4S)-1-({4-[(1,4-benzothiazolo-5-ylamino)carbonyl]biphenyl-2-yl}methyl)-4-(4-chlorophenyl)pyrrolidine-3-carboxylate.

Examples 198 to 232

The compounds of Example 198 to 232 shown in the following Tables were obtained in the same manner as in Example 197.

The structural formulae and physical properties of the above compounds of Reference Examples and compounds of Examples are shown in the following Tables 1 to 38. Moreover, the compounds described in the following Tables 39 and 40 can be easily produced in about the same manner as the methods described in the above Reference Examples, Examples, or production methods or by applying slightly changed methods obvious for those skilled in the art to those methods. In this connection, the symbols in Tables have the following meanings.

Rf: Reference Example No., Ex: Example No., No: Compound No., Structure: structural formula, salt: salt (2HCl: dihydrochloride, no description shows a free base), Me: methyl group, Et: ethyl group, Ac: acetyl group, iPr: isopropyl group, nPr: n-propyl group, tBu: t-butyl group, Boc: t-butoxycarbonyl group, Ph: phenyl group, Ts: p-toluenesulfonyl group, Ms: methanesulfonyl group, DATA: physical property data, NMR: nuclear magnetic resonance spectrum (TMS internal standard: $^1$H NMR: 400 MHz or 300 MHz, solvent in case that particularly not specified: DMSO-$d_6$), FP: FAB-MS (M+H)$^+$, H: retention time on HPLC under the following HPLC conditions (minute), Conditions Column: Wakosil-II 5C18 AR 2 mm×30 mm, solvent: MeOH/5 mM trifluoroacetic acid-H$_2$O=10/90 (0 min)-100/0 (4.0 min)-100/0 (4.5 min), flow rate: 1.2 mL/min.

INDUSTRIAL APPLICABILITY

Since the compounds of the present invention have an excellent inhibitory activity of capsaicin receptor VR1 activation, they are useful as medicaments, particularly therapeutic agents for various pains including neuropathic pains and inflammatory pains, headaches such as migraine and cluster headache, pruritus, bladder diseases including overactive bladder and interstitial cystitis, and the like.

The excellent inhibitory activity on capsaicin receptor VR1 activation of the compounds of the invention is confirmed by test methods shown below.

Test Example 1

Receptor Binding Assay Using VR1 Stably Expressing Cell

1) Construction of Human VR1 Stably Expressing Cell

A full-length cDNA encoding human VR1 was obtained by the following method. First, human brain mRNA was reverse transcribed using a reverse transcriptase to synthesize a first strand cDNA. Then, using the first strand cDNA as a template, PCR according to Hot Start method was carried out using Taq DNA polymerase. The above PCR was carried out by first conducting thermal denaturation of 98° C. (1 min) and then repeating a cycle consisting of 98° C. (15 sec)/63° C. (30 sec)/72° C. (3 min) 35 times using an oligonucleotide consisting of a base sequence of 424th to 443rd in a known human VR1 cDNA sequence (Genbank AJ277028.1) as a sense primer and an oligonucleotide consisting of a complimentary sequence of a base sequence of 3082nd to 3100th as an antisense primer.

An amplified DNA fraction was cloned using pCR-XL-TOPO vector (TOPO XL PCR Cloning Kit; Invitrogen, USA). The resulting plasmid DNA was digested with a restriction enzyme EcoRI to isolate human VR1-cDNA alone, which was then integrated into pcDNA3.1(+) plasmid (Invitrogen, USA). The above genetic engineering operations were carried out in accordance with known methods (Sambrook, J. et al, Molecular Cloning—A Laboratory Manual", Cold Spring Harbor Laboratory Press, NY, 2001) and directions attached to individual reagents.

Next, the resulting pcDNA3.1-VR1 was transduced into HEK293 cells or CHO-KL cells. VR1/HEK293 cells were selected using a DMEM medium (Invitrogen, USA) containing 10% FBS, 100 μg/ml streptomycin, 100 U/ml penicillin, and 400 μg/ml G418 and VR1/CHO cells were selected using a HumF12 medium (Invitrogen, USA) containing 10% FBS, 100 μg/ml streptomycin, 100 U/ml penicillin, and 400 μg/ml G418 to prepare receptor stably expressing cell lines. The receptor stably expressing cells were subcultured in respective above media.

2) A Method of Membrane Preparation

After the above VR1/HEK293 cells were cultured in glass dishes in a large quantity, the medium was removed and cells were scraped up with adding ice-cooled PBS. They were centrifuged at 1,000 rpm at 4° C. for 10 minutes. After a buffer for homogenization (25 mM Tris-HCl, 220 mM sucrose, pH 7.4) was added to the resulting sediment and the whole was homogenized, it was centrifuged at 2,200 rpm at 4° C. for 10 minutes. The resulting supernatant was centrifuged at 30,000×g at 4° C. for 20 minutes and an operation of adding 25 mM Tris-HCl, pH 7.4 to the resulting sediment and centrifuging it at 30,000×g at 4° C. for 20 minutes was repeated twice. The resulting sediment was suspended in 25 mM Tris-HCl, pH 7.4 and protein concentration was determined using a protein assay staining solution (Bio Rad, USA). The membrane preparation thus prepared was stored at −80° C.

3) Receptor Binding Assay

The test was carried out by modifying the method of [Neurosci. 57: 747-757 (1993)]. Assay buffer (25 mM Tris-HCl, 0.025% BSA, pH 7.4) (147 μl), 3 μl of a test compound, 50 μl of [$^3$H]RTX (about 50,000 dpm; Perkin-Elmer Life Science, USA), 100 μl of the above membrane preparation (protein amount of about 25 μg) were mixed and incubated at 37° C. for 60 minutes, and then the whole was incubated on ice for 10 minutes. An ice-cooled $\alpha_1$ acid protein (AGP; Sigma) was added in an amount of 200 μg/50 μl, followed by further 5 minutes of incubation. The completion of the incubation was effected by rapid filtration of the mixture using a GF/B filter (Perkin-Elmer Life Science, USA). After the filter was washed with ice-cooled 25 mM Tris-HCl buffer (pH 7.4) seven times, radioactivity of the filter was measured by means of a liquid scintillation counter (2500TR; Packard, USA). With regard to a specific binding, of the total binding amount of [$^3$H]RTX and membrane fractions of VR1 receptor stably expressing cell, a portion substituted by 1 μM RTX was regarded as a specific binding derived from VR1 receptor. Evaluation of the test compound was conducted as follows. Namely, a binding decrease at the addition of the compound was determined as a relative value when a binding decrease at the addition of RTX was regarded as 100%. Then, an IC$_{50}$ value was calculated according to the logistic regression method.

For example, the compounds of Examples 1, 7, 21, 33, 60, 71, 78, 85, 87, 110, 117, 122, 123, 129, 130, 143, 163, 170, 181, and 195 showed an IC$_{50}$ value of 1 μM or less. By the present test, it was confirmed that the compounds of the invention had affinity to VR1 receptor.

Test Example 2

$^{45}$Ca Uptake Assay Using VR1 Stably Expressing Cell

VR1/CHO cells were seeded in a 96-well white culture plate in a density of 30,000 cells per well. After 24 hours of culture in the previous-mentioned medium, the medium was replaced by 25 μl of assay buffer (PBS, 0.1 mM CaCl$_2$, 1 mM MgCl$_2$, 10 mM HEPES, 10 mM glucose, 0.025% BSA, pH 7.4), followed by 10 minutes of incubation at 37° C. To the well was added 25 µl of a mixed solution of about 4 kBq of $^{45}$Ca, capsaicin (Sigma, USA) adjusted so as to be a final concentration of 300 nM, and a test compound, followed by 10 minutes of incubation at 37° C. The mixed solution was washed with a buffer for washing (PBS, 0.1 mM CaCl$_2$, 1 mM MgCl$_2$) three times, 17 µl of 0.1 N NaOH and 100 µl of a liquid scintillator (microscinti-PS; Perkin-Elmer Life Science, USA) were added, and radioactivity was measured by means of a scintillation counter for microplate (Top Count; Perkin-Elmer Life Science, USA). VR1 receptor-specific $^{45}$Ca uptake induced by capsaicin was determined as a decrease induced by 10 µM capsazepine, VR1 antagonist, (Sigma, USA) from total $^{45}$Ca uptake in the cell at the stimulation with 300 nM capsaicin. Evaluation of the test compound was conducted as follows. Namely, an uptake decrease at the addition of the compound was determined as a relative value when an uptake decrease at the addition of capsazepine was regarded as 100%. Then, an IC$_{50}$ value was calculated according to the logistic regression method.

As a result, the compounds of the invention showed a potent inhibitory activity against $^{45}$Ca uptake via VR1.

Test Example 3

Capsaicin Test

The test was carried out in accordance with [Neuropharmacol. 31: 1279-1285 (1992)]. When 1.6 µg of capsaicin was administered to the planta of a mouse (ddY, male, 4- to 5-weeks old), a paw-licking action is induced. By measuring a time of expressing paw-licking action during 5 minutes after the administration, an inhibitory effect on pain behavior was evaluated. A test compound was administered intraperitoneally 30 minutes before the capsaicin administration or administered orally 45 minutes before the capsaicin administration. Evaluation of the test compound was conducted by determining each inhibition ratio in a test compound-administered group when the time of expressing paw-licking action in a vehicle-administered group was regarded as 100%.

As a result, the compounds of the invention showed a potent inhibitory effect on pain behavior in both of intraperitoneal administration and oral administration. With regard to representative compounds of Examples, inhibition ratios in the orally administered group (30 mg/kg) are shown in the following Table 41.

TABLE 41

| Compound | Inhibition ratio (%) |
|---|---|
| Example 33 | 66 |
| Example 78 | 76 |
| Example 85 | 86 |
| Example 87 | 67 |
| Reference compound[1] | 17 (26[2]) |
| Example 123 | 69 |
| Example 129 | 91 |
| Example 130 | 62 |
| Example 170 | 68 |

[1] The compound of example 115 in Patent Document 3
[2] A value at oral administration of 100 mg/kg On the other hand, the compound of example 115 described in the above Patent Document 3 did not show a significant inhibitory activity even at a dose of 100 mg/kg in the present test.

As a result of Test Examples 1 to 3, since the compounds of the invention show a remarkable pain inhibitory activity based on inhibition of VR1 receptor activation, it is expected that they can be effective anti-analgesics.

A pharmaceutical composition containing one or more types of the compounds of the invention and pharmaceutically acceptable salts thereof as the active ingredient can be prepared into tablets, powders, fine granules, granules, capsules, pills, liquids, injections, suppositories, ointments, paps, and the like, using carriers and excipients generally used for formulation, and other additives, which are orally or parenterally administered.

As the solid composition for oral administration in accordance with the invention, tablets, powders, granules, and the like are used. For such a solid composition, one or more active substances are mixed with at least one inactive diluent, for example lactose, mannitol, glucose, hydroxypropyl cellulose, microcrystalline cellulose, starch, polyvinylpyrrolidone, magnesium metasilicate aluminate, and the like. According to usual methods, the composition may contain additives other than inactive diluents, for example lubricants such as magnesium stearate, disintegrators such as cellulose calcium glycolate, stabilizers, solubilizers, or dissolution-auxiliary agents. If necessary, the tablets or pills may be coated with coating agents dissolvable in stomach or intestine.

The liquid composition for oral administration includes pharmaceutically acceptable emulsions, solutions, suspensions, syrups, and elixirs, and the like and contains inactive diluents generally used, for example purified water and ethyl alcohol. The composition may contain auxiliary agents such as solubilizers, dissolution-auxiliary agents, moisturizers and suspending agents, sweeteners, flavoring agents, aromatic agents, and preservatives.

The injections for parenteral administration encompass aseptic, aqueous or non-aqueous solutions, suspensions, and emulsions. The diluents for aqueous solutions and suspensions include, for example, distilled water for injections and physiological saline. The diluents for non-aqueous solutions and suspensions include, for example, propylene glycol, polyethylene glycol, vegetable oils such as olive oil, alcohols such as ethyl alcohol, polysorbate 80 (trade name), and the like.

Such composition may further contain additives including isotonic agents, preservatives, moisturizers, emulsifiers, dispersants, stabilizers, solubilizers, and dissolution-auxiliary agents. These may be sterilized by filtration through, for example, bacteria-retaining filter, blending with germicides, or irradiation. These may be also prepared into aseptic solid compositions and the compositions may be used, after dissolution in aseptic water or aseptic solvents for injections prior to use.

The clinical dose of the compounds of the invention to humans is appropriately determined in consideration of symptom, body weight, age, sex, and the like of patients to be applied. However, the dose is usually from 0.1 to 500 mg per day per adult in the case of oral administration and from 0.01 to 100 mg in the case of parenteral administration, which is administered once a day or by dividing into several doses. Since the dose may vary depending on various conditions, it is sufficient in a smaller amount than the above dose range in some cases.

TABLE 1

| Rf | Structure(salt) | DATA |
|---|---|---|
| 1 | 4-Ph, 3-Me-C6H3-CO2Et | FAB-MS 241 (M + H)+ |
| 2 | 4-Ph, 3-(BrCH2)-C6H3-CO2Et | FAB-MS 319 (M + H)+ |
| 3 | 4-Ph, 3-(piperidin-1-ylmethyl)-C6H3-CO2Et | FAB-MS 324 (M + H)+ |
| 4 | 4-Ph, 3-((2-methylpiperidin-1-yl)methyl)-C6H3-CO2Et | FAB-MS 310 (M + H)+ |
| 5 | 4-Ph, 3-(pyrrolidin-1-ylmethyl)-C6H3-CO2Et | FAB-MS 310 (M + H)+ |
| 6 | 4-Ph, 3-((3-acetamidopyrrolidin-1-yl)methyl)-C6H3-CO2Et | FAB-MS 367 (M + H)+ |
| 7 | 4-Ph, 3-(azepan-1-ylmethyl)-C6H3-CO2Et | FAB-MS 338 (M + H)+ |
| 8 | 4-Ph, 3-(morpholin-4-ylmethyl)-C6H3-CO2Et | FAB-MS 326 (M + H)+ |
| 9 | 4-Ph, 3-((4-methylpiperazin-1-yl)methyl)-C6H3-CO2Et | FAB-MS 339 (M + H)+ |
| 10 | 4-Ph, 3-((4-(pyridin-2-yl)piperazin-1-yl)methyl)-C6H3-CO2Et | FAB-MS 402 (M + H)+ |

TABLE 1-continued

| Rf | Structure(salt) | DATA |
|---|---|---|
| 11 | (3,6-dihydro-2H-pyridin-1-ylmethyl connected to 4-Ph-phenyl with CO₂Et) | FAB-MS 322 (M + H)⁺ |
| 12 | (1,2,3,4-tetrahydroisoquinolin-2-ylmethyl on 4-Ph-phenyl-CO₂Et) | FAB-MS 372 (M + H)⁺ |
| 13 | (Et₂N-CH₂ on 4-Ph-phenyl-CO₂Et) | FAB-MS 312 (M + H)⁺ |
| 14 | (Et(PhCH₂)N-CH₂ on 4-Ph-phenyl-CO₂Et) | FAB-MS 374 (M + H)⁺ |
| 15 | (Et(MeOCH₂CH₂)N-CH₂ on 4-Ph-phenyl-CO₂Et) | FAB-MS 342 (M + H)⁺ |
| 16 | ((MeOCH₂CH₂)₂N-CH₂ on 4-Ph-phenyl-CO₂Et) | FAB-MS 372 (M + H)⁺ |
| 17 | (piperidin-1-ylmethyl on 4-Ph-phenyl-CO₂H) | FAB-MS 296 (M + H)⁺ |
| 18 | (2-Me-piperidin-1-ylmethyl on 4-Ph-phenyl-CO₂H) | FAB-MS 310 (M + H)⁺ |
| 19 | (pyrrolidin-1-ylmethyl on 4-Ph-phenyl-CO₂H) | FAB-MS 282 (M + H)⁺ |
| 20 | (3-acetamido-pyrrolidin-1-ylmethyl on 4-Ph-phenyl-CO₂H) | FAB-MS 339 (M + H)⁺ |

TABLE 1-continued

| Rf | Structure(salt) | DATA |
|----|-----------------|------|
| 21 | 4-Ph, 3-(azepan-1-ylmethyl)benzoic acid | FAB-MS 310 (M + H)+ |
| 22 | 4-Ph, 3-(morpholin-4-ylmethyl)benzoic acid | FAB-MS 298 (M + H)+ |

TABLE 2

| Rf | Structure(salt) | DATA |
|----|-----------------|------|
| 23 | 4-Ph, 3-((4-methylpiperazin-1-yl)methyl)benzoic acid | FAB-MS 311 (M + H)+ |
| 24 | 4-Ph, 3-((4-(pyridin-2-yl)piperazin-1-yl)methyl)benzoic acid | FAB-MS 374 (M + H)+ |
| 25 | 4-Ph, 3-((3,6-dihydropyridin-1(2H)-yl)methyl)benzoic acid | FAB-MS 294 (M + H)+ |
| 26 | 4-Ph, 3-((3,4-dihydroisoquinolin-2(1H)-yl)methyl)benzoic acid | FAB-MS 344 (M + H)+ |
| 27 | 4-Ph, 3-((diethylamino)methyl)benzoic acid | FAB-MS 284 (M + H)+ |
| 28 | 4-Ph, 3-((N-benzyl-N-ethylamino)methyl)benzoic acid | FAB-MS 346 (M + H)+ |
| 29 | 4-Ph, 3-((N-ethyl-N-(2-methoxyethyl)amino)methyl)benzoic acid | FAB-MS 314 (M + H)+ |

TABLE 2-continued

| Rf | Structure(salt) | DATA |
|---|---|---|
| 30 | (structure) | FAB-MS 344 (M + H)+ |
| 31 | (structure) | FAB-MS 338 (M + H)+ |
| 32 | (structure) | FAB-MS 338 (M + H)+ |
| 33 | (structure) | FAB-MS 352 (M + H)+ |
| 34 | (structure) | FAB-MS 352 (M + H)+ |
| 35 | (structure) | FAB-MS 380 (M + H)+ |
| 36 | (structure) | FAB-MS 310 (M + H)+ |
| 37 | (structure) | FAB-MS 310 (M + H)+ |
| 38 | (structure) | FAB-MS 324 (M + H)+ |
| 39 | (structure) | FAB-MS 324 (M + H)+ |

TABLE 2-continued

| Rf | Structure(salt) | DATA |
|---|---|---|
| 40 | (cyclohexyl-iPr-N-CH2-)(4-Ph)C6H3-CO2H | FAB-MS 352 (M + H)+ |
| 41 | (2-OHC)(4-Ph)C6H3-CO2Et | FAB-MS 254 M− |
| 42 | (2-OHC-CH2-)(4-Ph)C6H3-CO2Et | FAB-MS 269 (M + H)+ |
| 43 | (piperidinyl-CH2CH2-)(4-Ph)C6H3-CO2Et | FAB-MS 338 (M + H)+ |
| 44 | (piperidinyl-CH2CH2-)(4-Ph)C6H3-CO2H | FAB-MS 310 (M + H)+ |

TABLE 3

| Rf | Structure(salt) | DATA |
|---|---|---|
| 45 | (4-F-C6H4)(2-Me)C6H3-CO2Et | FAB-MS 259 (M + H)+ |
| 46 | (4-F-C6H4)(2-BrCH2-)C6H3-CO2Et | FAB-MS 337 (M + H)+ |
| 47 | (4-Ph-4-HO-piperidinyl-CH2-)(4-Ph)C6H3-CO2Et | FAB-MS 416 (M + H)+ |
| 48 | (4-F-C6H4)(2-piperidinyl-CH2-)C6H3-CO2Et | FAB-MS 342 (M + H)+ |
| 49 | (4-F-piperidinyl-CH2-)(4-Ph)C6H3-CO2Et | FAB-MS 342 (M + H)+ |
| 50 | (3,3-F2-piperidinyl-CH2-)(4-Ph)C6H3-CO2Et | FAB-MS 360 (M + H)+ |
| 51 | (4-Ph-4-HO-piperidinyl-CH2-)(4-Ph)C6H3-CO2H | FAB-MS 388 (M + H)+ |

TABLE 3-continued
| Rf | Structure(salt) | DATA |
|----|-----------------|------|
| 52 | 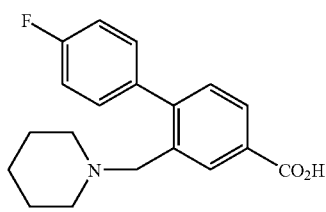 | FAB-MS 314 (M + H)+ |
| 53 | 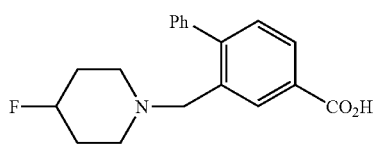 | FAB-MS 314 (M + H)+ |
| 54 | 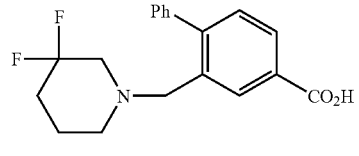 | FAB-MS 332 (M + H)+ |
| 55 | 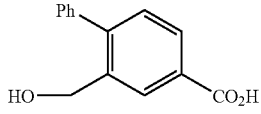 | FAB-MS 227 (M + H)− |
| 56 | 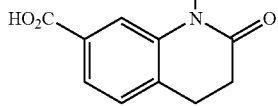 | FAB-MS 206 (M + H)+ |
| 57 | 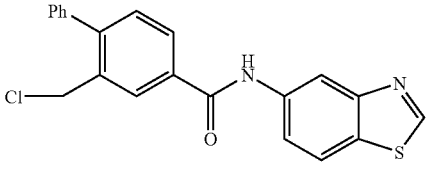 | FAB-MS 379 (M + H)+ |
| 58 | 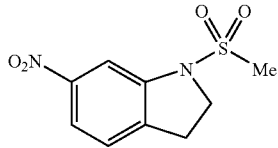 | FAB-MS 242 M+ |
| 59 | 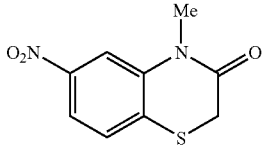 | FAB-MS 224 M− |
| 60 | 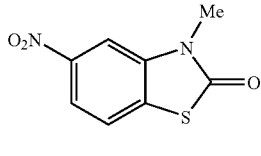 | FAB-MS 211 (M + H)+ |
TABLE 3-continued
| Rf | Structure(salt) | DATA |
|----|-----------------|------|
| 61 | 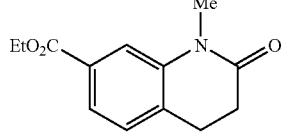 | FAB-MS 234 (M + H)+ |
| 62 | 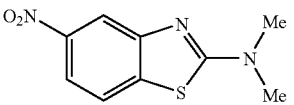 | ESI-MS 224 (M + H)+ |
| 63 | 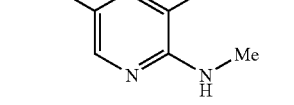 | FAB-MS 188 (M + H)+ |
| 64 | 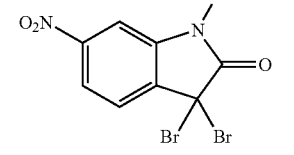 | EI-MS 350 M+ |
TABLE 4
| Rf | Structure(salt) | DATA |
|----|-----------------|------|
| 65 | 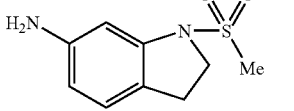 | FAB-MS 213 (M + H)+ |
| 66 | 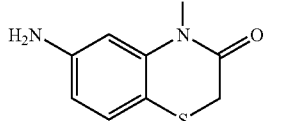 | FAB-MS 193 (M + H)+ |
| 67 | 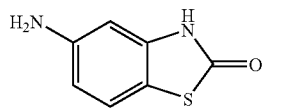 | EI-MS 166 M+ |
| 68 | 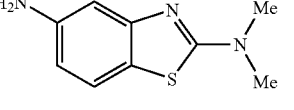 | EI-MS 193 M+ |
| 69 | 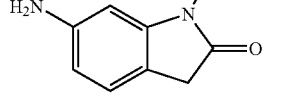 | EI-MS 162 M+ |
| 70 | 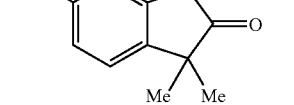 | FAB-MS 177 (M + H)+ |

TABLE 4-continued

| Rf | Structure(salt) | DATA |
|---|---|---|
| 71 | 5-amino-3,3-difluoroindolin-2-one | FAB-MS 185 (M + H)+ |
| 72 | methyl (E)-3-(4-(ethoxycarbonyl)-2-nitrophenyl)acrylate | FAB-MS 280 (M + H)+ |
| 73 | ethyl 2-oxo-1,2,3,4-tetrahydroquinoline-7-carboxylate | FAB-MS 220 (M + H)+ |
| 74 | 7-amino-1-methyl-3,4-dihydroquinolin-2(1H)-one | ESI-MS 177 (M + H)+ |
| 75 | 5-amino-3-chloro-N-methylpyridin-2-amine | FAB-MS 158 (M + H)+ |
| 76 | ethyl 2-methyl-4-phenylbenzoate | FAB-MS 241 (M + H)+ |
| 77 | ethyl 2-(bromomethyl)-4-phenylbenzoate | EI-MS 318, 320 M+ |
| 78 | ethyl 2-((dimethylamino)methyl)-4-phenylbenzoate | FAB-MS 284 (M + H)+ |
| 79 | ethyl 2-(piperidin-1-ylmethyl)-4-phenylbenzoate | FAB-MS 324 (M + H)+ |

TABLE 4-continued

| Rf | Structure(salt) | DATA |
|---|---|---|
| 80 | ethyl 3-((dimethylamino)methyl)-4-phenylbenzoate | FAB-MS 284 (M + H)+ |
| 81 | 4-phenyl-2-(piperidin-1-ylmethyl)benzoic acid | FAB-MS 296 (M + H)+ |
| 82 | ethyl 2-((dimethylamino)methyl)-4-phenylbenzoate | FAB-MS 254 (M − H)− |
| 83 | 3-((dimethylamino)methyl)-4-phenylbenzoic acid | FAB-MS 256 (M + H)+ |
| 84 | ethyl 4'-chloro-2-methyl-[1,1'-biphenyl]-4-carboxylate | FAB-MS 275 (M + H)+ |
| 85 | ethyl 3'-chloro-2-methyl-[1,1'-biphenyl]-4-carboxylate | FAB-MS 275 (M + H)+ |
| 86 | ethyl 2-methyl-3'-(trifluoromethyl)-[1,1'-biphenyl]-4-carboxylate | FAB-MS 309 (M + H)+ |

TABLE 5

| Rf | Structure(salt) | DATA |
|---|---|---|
| 87 | 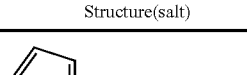 | FAB-MS 247 (M + H)+ |

TABLE 5-continued

| Rf | Structure(salt) | DATA |
|---|---|---|
| 88 | 3'-F, 2-Me, 4-CO2Et biphenyl | FAB-MS 275 (M + H)+ |
| 89 | 3-Cl, 4-Ph, 5-Me, benzoate CO2Et | FAB-MS 275 (M + H)+ |
| 90 | 4'-Cl, 2-CH2Br, 4-CO2Et biphenyl | NMR δ 1.32-1.40 (3 H, m), 4.30-4.40 (2 H, m), 4.68 (2 H, brs), 7.38-8.20 (7 H, m) |
| 91 | 3'-Cl, 2-CH2Br, 4-CO2Et biphenyl | NMR δ 1.30-1.40 (3 H, m), 4.30-4.44 (2 H, m), 4.67 (2 H, brs), 7.40-8.25 (7 H, m) |
| 92 | 3'-CF3, 2-CH2Br, 4-CO2Et biphenyl | NMR δ 1.30-1.40 (3 H, m), 4.30-4.44 (2 H, m), 4.66 (2 H, brs), 7.46-8.25 (7 H, m) |
| 93 | 2-thienyl, 2-CH2Br, 4-CO2Et phenyl | NMR δ 1.29-1.40 (3 H, m), 4.29-4.44 (2 H, m), 4.87 (2 H, brs), 7.23-8.24 (6 H, m) |
| 94 | 3-Cl, 4-Ph, 5-CH2Br, benzoate CO2Et | FAB-MS 353 (M + H)+ 355 (M + H)+ |
| 95 | 3'-F, 2-CH2Br, 4-CO2Et biphenyl | GC-MS 336 M+ 338 M+ |

TABLE 5-continued

| Rf | Structure(salt) | DATA |
|---|---|---|
| 96 | 4-Cl-C6H4 / Ph with piperidinyl-CH2 and CO2Et | FAB-MS 358 (M + H)+ |
| 97 | 3-Cl-C6H4 / Ph with piperidinyl-CH2 and CO2Et | FAB-MS 358 (M + H)+ |
| 98 | 3-F3C-C6H4 / Ph with piperidinyl-CH2 and CO2Et | FAB-MS 392 (M + H)+ |
| 99 | 2-thienyl / Ph with piperidinyl-CH2 and CO2Et | FAB-MS 330 (M + H)+ |
| 100 | 4-CN-piperidinyl-CH2, Ph, CO2Et | FAB-MS 349 (M + H)+ |
| 101 | 3-(MeOCH2)-piperidinyl-CH2, Ph, CO2Et | FAB-MS 368 (M + H)+ |
| 102 | 3-(piperidinyl-C(O))-piperidinyl-CH2, Ph, CO2Et | FAB-MS 435 (M + H)+ |
| 103 | 2,5-dimethylpyrrolidinyl-CH2, Ph, CO2Et | FAB-MS 338 (M + H)+ |
| 104 | 2,6-dimethylmorpholinyl-CH2, Ph, CO2Et | FAB-MS 354 (M + H)+ |

TABLE 5-continued

| Rf | Structure(salt) | DATA |
|---|---|---|
| 105 | Et-N-Et, C=O on piperidine-3-yl, N-CH2-[2-Ph-5-CO2Et-phenyl] | FAB-MS 423 (M + H)+ |
| 106 | Et-N-Et, C=O on piperidine-2-yl, N-CH2-[2-Ph-5-CO2Et-phenyl] | FAB-MS 423 (M + H)+ |
| 107 | 2-Me-pyrrolidin-1-yl-CH2-[2-Ph-5-CO2Et-phenyl] | FAB-MS 324 (M + H)+ |
| 108 | 2-(MeOCH2)-pyrrolidin-1-yl-CH2-[2-Ph-5-CO2Et-phenyl] | FAB-MS 354 (M + H)+ |

TABLE 6

| Rf | Structure(salt) | DATA |
|---|---|---|
| 109 | 3-OEt-pyrrolidin-1-yl-CH2-[2-Ph-5-CO2Et-phenyl] | FAB-MS 354 (M + H)+ |
| 110 | 3-Me-pyrrolidin-1-yl-CH2-[2-Ph-5-CO2Et-phenyl] | FAB-MS 324 (M + H)+ |
| 111 | 3-CF3-piperidin-1-yl-CH2-[2-Ph-5-CO2Et-phenyl] | FAB-MS 392 (M + H)+ |
| 112 | nPr-CO-NH-piperidin-3-yl, N-CH2-[2-Ph-5-CO2Et-phenyl] | FAB-MS 409 (M + H)+ |
| 113 | 2-NO2-C6H4-SO2-N(Et)-CH2-[2-Ph-5-CO2Et-phenyl] | FAB-MS 469 (M + H)+ |

TABLE 6-continued

| Rf | Structure(salt) | DATA |
|---|---|---|
| 114 | (structure) | FAB-MS 409 (M + H)+ |
| 115 | (structure) | FAB-MS 407 (M + H)+ |
| 116 | (structure) | FAB-MS 425 (M + H)+ |
| 117 | (structure) | FAB-MS 425 (M + H)+ |
| 118 | (structure) | FAB-MS 342 (M + H)+ |
| 119 | (structure) | FAB-MS 358 (M + H)+ |
| 120 | (structure) | FAB-MS 338 (M + H)+ |
| 121 | (structure) | FAB-MS 356 (M + H)+ |
| 122 | (structure) | FAB-MS 407 (M + H)+ |

TABLE 6-continued

| Rf | Structure(salt) | DATA |
|---|---|---|
| 123 | (4-Me-piperidinyl)-piperidinyl-CH2-(2-Ph-phenyl)-5-CO2Et | FAB-MS 421 (M + H)+ |
| 124 | Et2N-C(O)-CH2-N(Et)-CH2-(2-Ph-phenyl)-5-CO2Et | FAB-MS 397 (M + H)+ |
| 125 | 2,4-dinitrophenyl-CH(OH)-C(=CH2)-CO2Me | FAB-MS 282 M− |
| 126 | 7-HO2C-1-Me-3-Me-quinolin-2(1H)-one | FAB-MS 218 (M + H)+ |
| 127 | 7-HO2C-1-n-Pr-3,4-dihydroquinolin-2(1H)-one | FAB-MS 234 (M + H)+ |
| 128 | 7-HO2C-1-Me-3-Me-3,4-dihydroquinolin-2(1H)-one | FAB-MS 220 (M + H)+ |
| 129 | 5-HO2C-3-Br-2-(N-Me)pyridine | ESI-MS 245, 247 (M + H)+ |
| 130 | 5-HO2C-3-Cl-2-(N-Me)pyridine | ESI-MS 201 (M + H)+ |

TABLE 7

| Rf | Structure(salt) | DATA |
|---|---|---|
| 131 | 5-HO2C-3-F-2-(N-Me)pyridine | ESI-MS 185 (M + H)+ |
| 132 | 4-Ph-2-(2-piperidin-1-yl-ethyl)benzoic acid | FAB-MS 310 (M + H)+ |

TABLE 7-continued
| Rf | Structure(salt) | DATA |
|---|---|---|
| 133 | 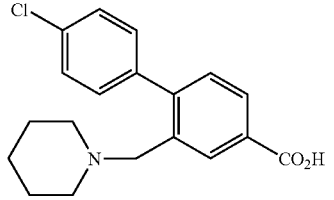 | FAB-MS 330 (M + H)+ |
| 134 | 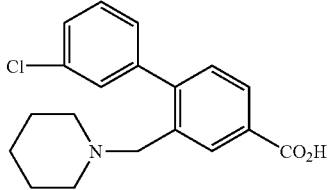 | FAB-MS 330 (M + H)+ |
| 135 | 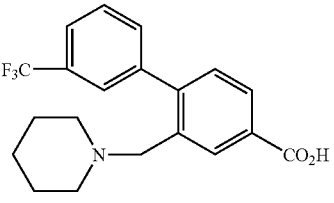 | FAB-MS 364 (M + H)+ |
| 136 | 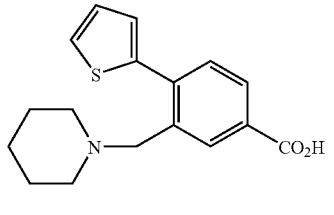 | FAB-MS 302 (M + H)+ |
| 137 | 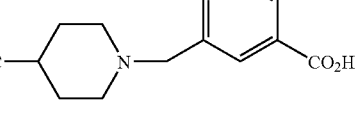 | FAB-MS 321 (M + H)+ |
| 138 | 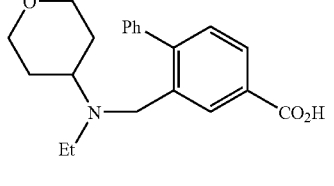 | FAB-MS 340 (M + H)+ |
| 139 | 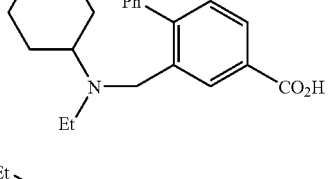 | FAB-MS 356 (M + 2H)+ |
| 140 | 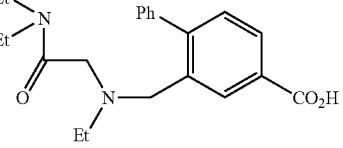 | FAB-MS 369 (M + H)+ |
| 141 | 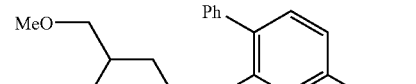 | FAB-MS 340 (M + H)+ |
| 142 | 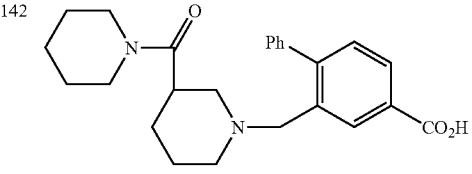 | FAB-MS 407 (M + H)+ |
| 143 | 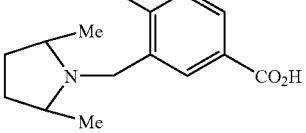 | FAB-MS 310 (M + H)+ |
| 144 | 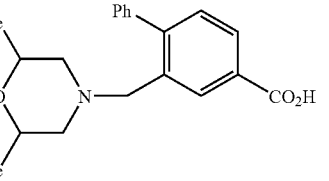 | FAB-MS 326 (M + H)+ |
| 145 | 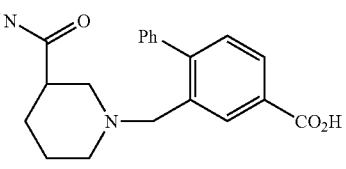 | FAB-MS 395 (M + H)+ |
| 146 | 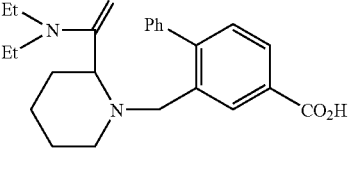 | FAB-MS 395 (M + H)+ |
| 147 | 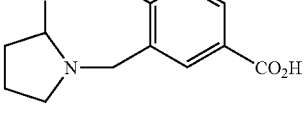 | FAB-MS 296 (M + H)+ |
| 148 | 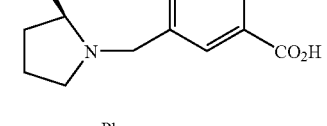 | FAB-MS 326 (M + H)+ |
| 149 | 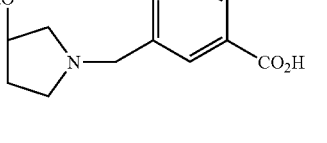 | FAB-MS 326 (M + H)+ |

TABLE 7-continued
| Rf | Structure(salt) | DATA |
|---|---|---|
| 150 | 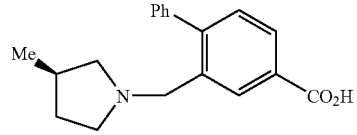 | FAB-MS 296 (M + H)+ |
| 151 | 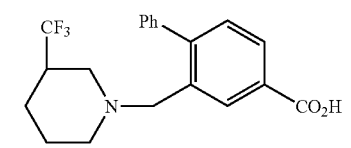 | FAB-MS 364 (M + H)+ |
TABLE 7-continued
| Rf | Structure(salt) | DATA |
|---|---|---|
| 152 | 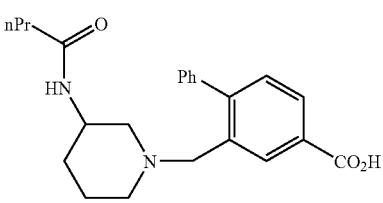 | FAB-MS 381 (M + H)+ |
TABLE 8
| Rf | Structure(salt) | DATA |
|---|---|---|
| 153 | 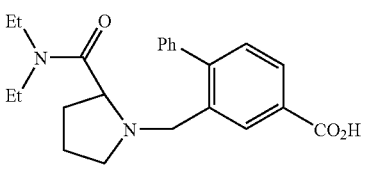 | FAB-MS 381 (M + H)+ |
| 154 | 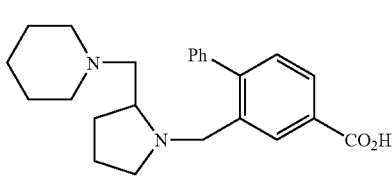 | FAB-MS 379 (M + H)+ |
| 155 | 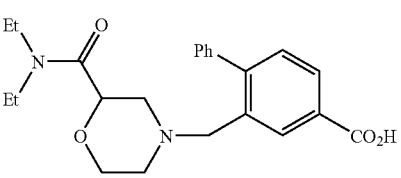 | FAB-MS 397 (M + H)+ |
| 156 | 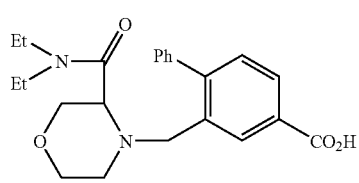 | FAB-MS 397 (M + H)+ |
| 157 | 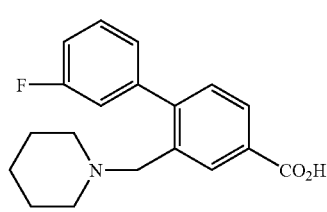 | FAB-MS 314 (M + H)+ |
| 158 | 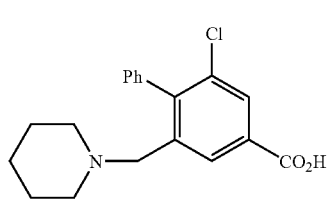 | FAB-MS 330 (M + H)+ |

TABLE 8-continued
| Rf | Structure(salt) | DATA |
|---|---|---|
| 159 | 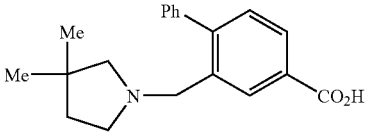 | FAB-MS 310 (M + H)+ |
| 160 | 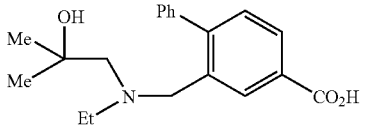 | FAB-MS 328 (M + H)+ |
| 161 | 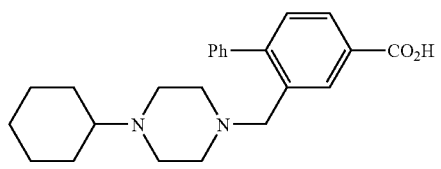 | FAB-MS 379 (M + H)+ |
| 162 | 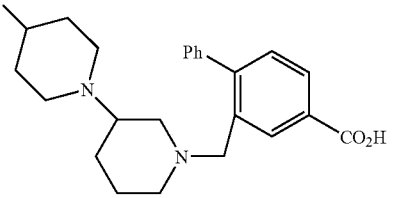 | FAB-MS 393 (M + H)+ |
| 163 | 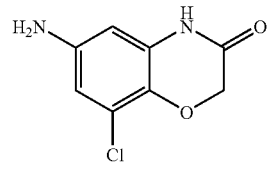 | FAB-MS 198 M+ |
| 164 | 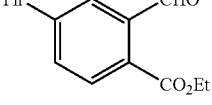 | FAB-MS 254 M+ |
| 165 | 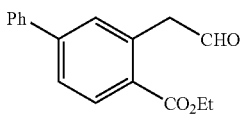 | FAB-MS 269 (M + H)+ |
| 166 | 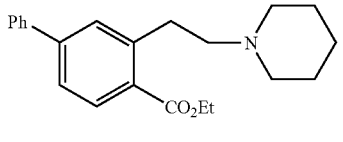 | FAB-MS 338 (M + H)+ |
| 167 | 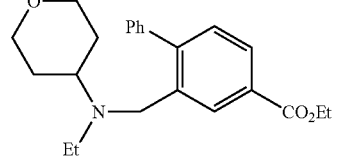 | FAB-MS 368 (M + H)+ |

TABLE 8-continued

| Rf | Structure(salt) | DATA |
|---|---|---|
| 168 | (tetrahydrothiopyran-4-yl)-N-ethyl-N-[(2-phenyl-5-ethoxycarbonylphenyl)methyl]amine | FAB-MS 384 (M + H)⁺ |
| 169 | Boc-N-piperidine-3-yl-piperidine | FAB-MS 269 (M + H)⁺ |
| 170 | Boc-N-piperidine-3-yl-(4-methylpiperidine) | FAB-MS 283 (M + H)⁺ |
| 171 | 4-Ph-3-(CH₂Cl)-C₆H₃-C(O)NH-(1-Me-3,4-dihydroquinolin-2(1H)-one-7-yl) | ESI-MS 405 (M + H)⁺ |
| 172 | 4-Ph-3-(CH₂OMs)-C₆H₃-C(O)NH-(2-Me-3-oxo-3,4-dihydro-2H-1,4-benzoxazin-6-yl) | FAB-MS 467 (M + H)⁺ |
| 173 | MeO₂C-(1-Me-3-Me-3,4-dihydroquinolin-2(1H)-one-7-yl) | FAB-MS 232 (M + H)⁺ |
| 174 | EtO₂C-(1-n-Pr-3,4-dihydroquinolin-2(1H)-one-7-yl) | FAB-MS 262 (M + H)⁺ |

TABLE 9

| Rf | Structure(salt) | DATA |
|---|---|---|
| 175 | MeO₂C-(1-Me-3-Me-3,4-dihydroquinolin-2(1H)-one-7-yl) | FAB-MS 234 (M + H)⁺ |
| 176 | HO₂C-(1-Et-3,4-dihydroquinolin-2(1H)-one-7-yl) | ESI-MS 220 (M + H)⁺ |
| 177 | HO₂C-(1-(2-fluoroethyl)-3,4-dihydroquinolin-2(1H)-one-7-yl) | ESI-MS 238 (M + H)⁺ |
| 178 | EtO₂C-(3-chloro-6-(N,N-dimethylamino)pyridin-5-yl) | ESI-MS 230 (M + H)⁺ |

TABLE 9-continued
| Rf | Structure(salt) | DATA |
|---|---|---|
| 179 | 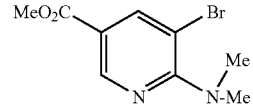 | ESI-MS 259, 261 (M + H)+ |
| 180 | 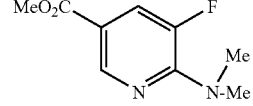 | ESI-MS 199 (M + H)+ |
| 181 | 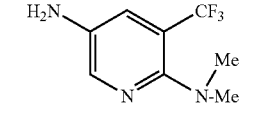 | ESI-MS 206 (M + H)+ |
| 182 | 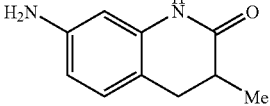 | FAB-MS 177 (M + H)+ |
| 183 | 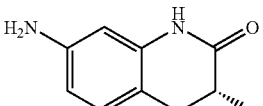 | FAB-MS 179 (M + H)+ |
| 184 | 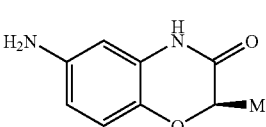 | FAB-MS 179 (M + H)+ |
| 185 | 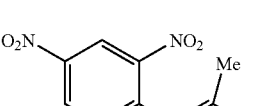 | ESI-MS 281 (M + H)+ |
| 186 | 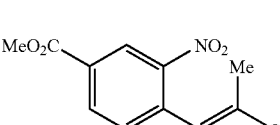 | FAB-MS 294 (M + H)+ |
| 187 | 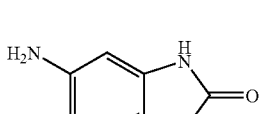 | ESI-MS 217 (M + H)+ |
| 188 | 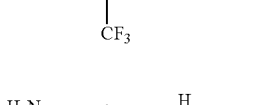 | FAB-MS 162 (M + H)+ |
TABLE 9-continued
| Rf | Structure(salt) | DATA |
|---|---|---|
| 189 | 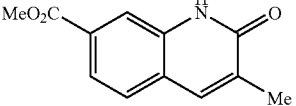 | FAB-MS 218 (M + H)+ |
| 190 | 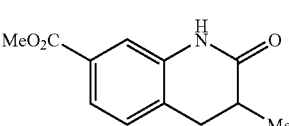 | FAB-MS 220 (M + H)+ |
| 191 | 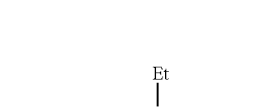 | ESI-MS 191 (M + H)+ |
| 192 | 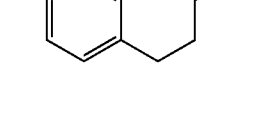 | ESI-MS 209 (M + H)+ |
| 193 | 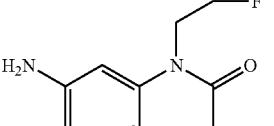 | FAB-MS 189 (M + H)+ |
| 194 | 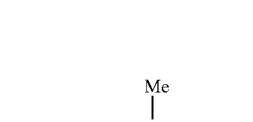 | FAB-MS 205 (M + H)+ |
| 195 | 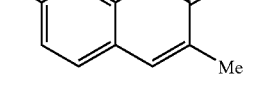 | ESI-MS 156 (M + H)+ |
| 196 | 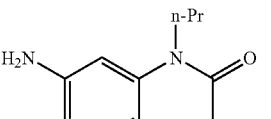 | ESI-MS 172 (M + H)+ |

TABLE 10
| Rf | Structure(salt) | DATA |
|----|-----------------|------|
| 197 | 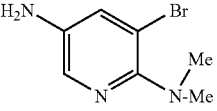 | ESI-MS 216, 218 (M + H)+ |
| 198 | 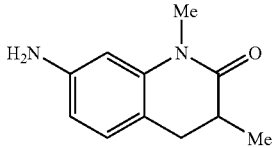 | EI-MS 190 M+ |
| 199 | 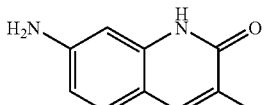 | FAB-MS 175 (M + H)+ |
| 200 | 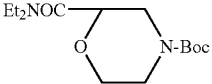 | FAB-MS 287 (M + H)+ |
| 201 | 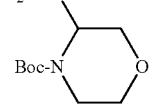 | FAB-MS 287 (M + H)+ |
| 202 | 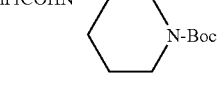 | FAB-MS 271 (M + H)+ |
| 203 | 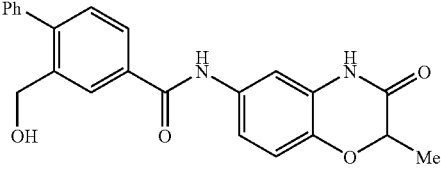 | FAB-MS 389 (M + H)+ |
| 204 | 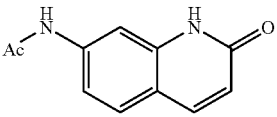 | FAB-MS 203 (M + H)+ |
| 205 | 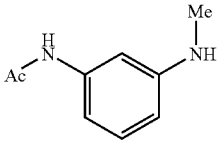 | FAB-MS 165 (M + H)+ |
| 206 | 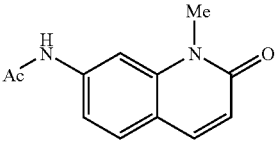 | EI-MS 216 M+ |
| 207 | 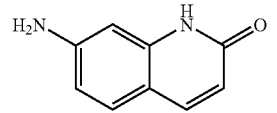 | EI-MS 160 M+ |

TABLE 10-continued

| Rf | Structure(salt) | DATA |
|---|---|---|
| 208 | 7-amino-1-methylquinolin-2(1H)-one | EI-MS 174 M+ |
| 209 | Benzyl 2-(2,4-dinitro-6-(trifluoromethyl)phenyl)malonate | ESI-MS 517 (M + H)+ |
| 210 | Dibenzyl 2-(2,4-dinitro-6-methylphenyl)malonate | FAB-MS 465 (M + H)+ |
| 211 | Ethyl 5-chloro-6-((2,4-dimethoxybenzyl)amino)nicotinate | ESI-MS 351 (M + H)+ |
| 212 | 3-chloropyridine-2,5-diamine | ESI-MS 144 (M + H)+ |
| 213 | 3,3-difluoro-1-methyl-5-nitroindolin-2-one | FAB-MS 229 (M + H)+ |
| 214 | 5-amino-3,3-difluoro-1-methylindolin-2-one | EI-MS 198 M+ |
| 215 | N,N-dimethyl-5-nitro-3-(trifluoromethyl)pyridin-2-amine | FAB-MS 236 (M + H)+ |
| 216 | Ethyl (S)-2-(2,4-dinitrophenoxy)propanoate | FAB-MS 285 (M + H)+ |
| 217 | Methyl (S)-2-(2,4-dinitrophenoxy)propanoate | FAB-MS 271 (M + H)+ |

TABLE 10-continued

| Rf | Structure(salt) | DATA |
|---|---|---|
| 218 | (structure: 6-(trifluoroacetamido)-2H-benzo[b][1,4]oxazin-3(4H)-one) | FAB-MS 261 (M + H)+ |

TABLE 11

| Rf | Structure(salt) | DATA |
|---|---|---|
| 219 | (structure: 8-chloro-6-(trifluoroacetamido)-2H-benzo[b][1,4]oxazin-3(4H)-one) | FAB-MS 293 (M − H)− |
| 220 | (structure: 7-amino-6-chloro-3,4-dihydroquinolin-2(1H)-one) | EI-MS 196 M+ |
| 221 | (structure: ethyl 3-chloro-4-hydroxy-5-methylbenzoate) | FAB-MS 215 (M + H)+ |
| 222 | (structure: ethyl 3-chloro-5-methyl-4-(trifluoromethylsulfonyloxy)benzoate) | NMR (300 MHz, DMSO-$d_6$) δ 1.33 (3 H, t, J = 5.1 Hz), 2.47 (3 H, s), 4.35 (2 H, q, J = 5.1 Hz), 8.03 (1 H, s), 8.04 (1 H, s) |
| 223 | (structure: ethyl 3-((ethylamino)methyl)-4-phenylbenzoate) | FAB-MS 284 (M + H)+ |
| 224 | (structure: 1-(ethylamino)-2-methylpropan-2-ol) | FAB-MS 118 (M + H)+ |
| 225 | (structure: N,N-diethyl morpholine-2-carboxamide · HCl) | FAB-MS 187 (M + H)+ |
| 226 | (structure: N,N-diethyl morpholine-3-carboxamide · HCl) | FAB-MS 187 (M + H)+ |
| 227 | (structure: N-(piperidin-3-yl)butanamide · HCl) | FAB-MS 171 (M + H)+ |

TABLE 11-continued

| Rf | Structure(salt) | DATA |
| --- | --- | --- |
| 228 | [piperidin-3-yl-piperidine] 2(HCl) | FAB-MS 169 (M + H)+ |
| 229 | [3-(4-methylpiperidin-1-yl)piperidine] 2(HCl) | EI-MS 182 M+ |
| 230 | [1-acetyl-2,6-dimethylpiperazine] | GC-MS 156 M+ |
| 231 | [N-(2-piperidin-1-ylethyl)isobutyramide] | FAB-MS 199 (M + H)+ |
| 232 | [3-(isobutyrylamino)propyl isobutyrate] | FAB-MS 216 (M + H)+ |
| 233 | [1-ethyl-2,5-dimethylpiperazine] | GC-MS 142 M+ |
| 234 | [3-(isobutylamino)propan-1-ol] | FAB-MS 132 (M + H)+ |
| 235 | [N-(2-piperidin-1-ylethyl)-2-methylpropan-1-amine] | LC-MS 185 (M + H)+ |

TABLE 12

| Ex | Structure(salt) | DATA |
| --- | --- | --- |
| 1 | [4-phenyl-3-(piperidin-1-ylmethyl)-N-(3-methoxyphenyl)benzamide] HCl | NMR: δ1.20-1.35(1H, m), 1.53-1.63(3H, m), 1.75-1.91(2H m), 2.54-2.65(2H, m), 3.16-3.25(2H, m), 3.76(3H, s), 4.37(2H, d, J = 5.1Hz), 6.70(1H, dd, J = 8.3, 2.0Hz), 7.26(1H t, J = 8.2Hz), 7.37-7.43(2H, m), 7.45-7.58(5H, m), 7.63-7.67(1H, m), 8.02(1H, d, J = 7.8Hz), 8.70-8.75(1H, m), 10.22 (1H, brs), 10.58(1H, s). FAB-MS: 401(M + H)+ |

TABLE 12-continued

| Ex | Structure(salt) | DATA |
|---|---|---|
| 2 | 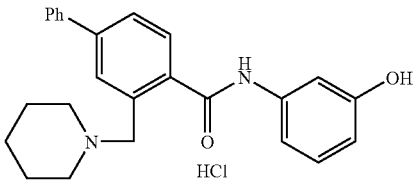 | NMR: δ1.35-1.49(1H, m), 1.64-1.72(1H, m), 1.75-1.85(4 H m), 2.93-3.06(2H, m), 3.36-3.42(2H, m), 4.47(2H, d, J = 5.2Hz), 6.53-6.59(1H, m), 7.11-7.17(2H, m), 7.34(1H, s), 7.43-7.48(1H, m), 7.51-7.57(2H, m), 7.83-8.89(3H, m), 7.91-7.95(1H, m), 8.25(1H, s), 9.52(1H, s), 10.04(1 H brs), 10.56(1H, s). FAB-MS: 387(M + H)⁺ |
| 3 | 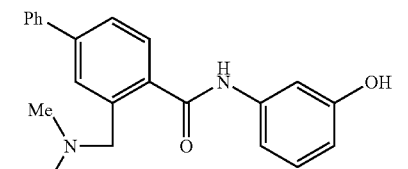 | NMR: 2.79(3H, s), 2.80(3H, s), 4.43(2H, d, J = 5.4Hz), 6.54-6.60(1H, m), 7.11-7.21(2H, m), 7.33(1H, s), 7.43-7.48 (1H, m), 7.51-7.56(2H, m), 7.84-7.96(4H, m), 8.20(1H, d, J = 1.5Hz), 9.56(1H, s), 10.18(1H, brs), 10.60(1H, s). FAB-MS: 347(M + H)⁺ |
| 4 | 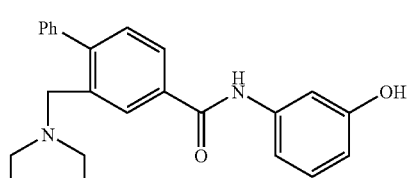 | NMR: δ1.19-1.34(1H, m), 1.52-1.63(3H, m), 1.73-1.88(2 H m), 2.53-2.64(2H, m), 3.18-3.24(2H, m), 4.37(2H, d, J = 5.4Hz), 6.50-6.55(1H, m), 7.13(1H, t, J = 8.21Hz), 7.29-7.33 (1H, m), 7.37-7.42(2H, m), 7.44-7.56(5H, m), 8.02(1H, dd, J = 8.1, 1.7Hz), 8.67(1H, d, J = 1.7Hz), 9.45(1H, s), 10.19 (1H, brs), 10.44(1H, s). FAB-MS: 387(M + H)⁺ |
| 5 | 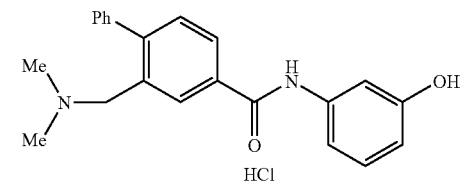 | NMR: δ2.55(6H, s), 4.38(2H, s), 6.49-6.56(1H, m), 7.13 (1H, t, J = 8.3Hz), 7.28(1H, d, J = 8.3Hz), 7.39(1H, d, J = 7.8 Hz), 7.43-7.57(5H, m), 8.03(1H, d, J = 8.3Hz), 8.54(1H, s), 9.54(1H, s), 10.32(1H, s), 10.36(1H, brs). FAB-MS: 347 (M + H)⁺ |
| 6 | 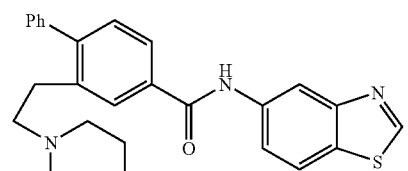 | NMR: δ1.26-1.42(1H, m), 1.61-1.79(5H, m), 2.72-2.85(2 H m), 3.04-3.13(2H, m), 3.22-3.36(4H, m), 7.39-7.45(3 H m), 7.45-7.50(1H, m), 7.45-7.56(2H, m), 7.90-8.01(2 H m), 8.10-8.16(2H, m), 8.70(1H, d, J = 1.9Hz), 9.40(1H, s), 9.97(1H, brs), 10.69(1H, s). FAB-MS: 442(M + H)⁺ |
| 7 | 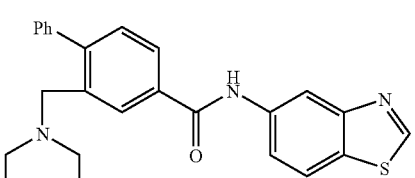 | NMR: δ1.20-1.33(1H, m), 1.52-1.65(3H, m), 1.74-1.93(2 H m), 2.54-2.68(2H, m), 3.18-3.28(2H, m), 4.41(2H, d, J = 5.4Hz), 7.42(2H, d, J = 6.8Hz), 7.46-7.58(4H, m), 8.02-8.10(2H, m), 8.15(1H, d, J = 8.8Hz), 8.79(1H, s), 9.42(1H, s), 10.20(1H, brs), 10.88(1H, s). FAB-MS: 428(M + H)⁺ |
| 8 | 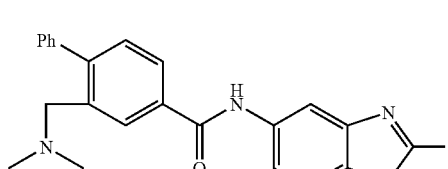 | NMR: δ1.20-1.34(1H, m), 1.52-1.66(3H, m), 1.81-1.97(2 H m), 2.55-2.68(2H, m), 2.81(3H, s), 3.17-3.30(2H, m), 4.39(2H, d, J = 4.8Hz), 7.41(2H, d, J = 7.4Hz), 7.46-7.58(4 H m), 8.01(2H, s), 8.04(1H, d, J = 7.8Hz), 8.63(1H, s), 8.85 (1H, s), 10.39(1H, brs), 10.87(1H, s). FAB-MS: 442(M + H)⁺ |

TABLE 12-continued

| Ex | Structure(salt) | DATA |
|---|---|---|
| 9 | 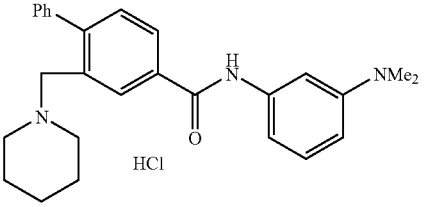 | NMR: δ1.20-1.35(1H, m), 1.52-1.62(3H, m), 1.78-1.92(2 H m), 2.53-2.64(2H, m), 2.90(6H, s), 3.17-3.26(2H, m), 4.37 (2H, d, J = 5.4Hz), 6.50(1H, dd, J = 8.3, 1.9Hz), 7.15(1H, t, J = 8.3Hz), 7.33-7.43(4H, m), 7.45-7.56(4H, m), 8.01(1 H dd, J = 8.3, 2.0Hz), 8.74-8.76(1H, m), 10.34(1H, brs), 10.40 (1H, s). FAB-MS: 414(M + H)⁺ |

TABLE 13

| Ex | Structure(salt) | DATA |
|---|---|---|
| 10 | 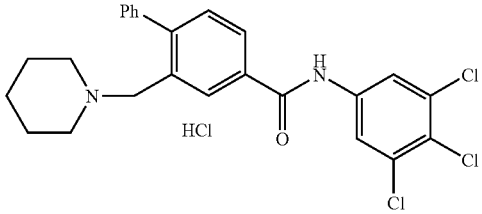 | NMR: δ1.20-1.38(1H, m), 1.52-1.68(3H, m), 1.78-1.96 (2H, m), 2.55-2.70(2H, m), 3.18-3.28(2H, m), 4.38(2 H d, J = 4.4Hz), 7.39(2H, d, J = 7.4Hz), 7.45-7.60(5H, m), 8.02(1H, d, J = 7.8Hz), 8.33(2H, s), 8.78(1H, s), 10.07 (1H, s). FAB-MS: 473(M + H)⁺ |
| 11 | 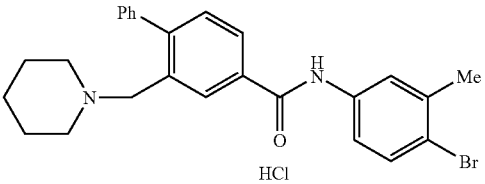 | NMR: δ1.20-1.33(1H, m), 1.53-1.63(3H, m), 1.75-1.90 (2H, m), 2.35(3H, s), 2.52-2.66(2H, m), 3.15-3.25(2 H m), 4.37(2H, d, J = 6.6Hz), 7.37-7.42(2H, m), 7.46-7.58 (5H, m), 7.76(1H, dd, J = 8.8, 2.5Hz), 7.97(1H, d, J = 2.5 Hz), 8.01(1H, dd, J = 8.3, 1.9Hz), 8.72(1H, d, J = 1.9Hz), 10.17(1H, s), 10.69(1H, s). FAB-MS: 463(M + H)⁺ |
| 12 | 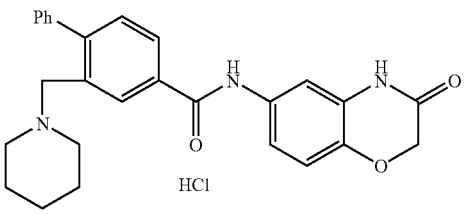 | NMR: δ1.20-1.35(1H, m), 1.53-1.63(3H, m), 1.70-.185 (2H, m), 2.53-2.65(2H, m), 3.16-3.24(2H,, m), 4.37(2 H d, J = 5.3Hz), 4.55(2H, s), 6.94(1H, d, J = 8.8Hz), 7.35 (1H, dd, J = 8.6, 2.3Hz), 7.38-7.42(2H, m), 7.46-7.57(4 H m), 7.68(1H, d, J = 2.4Hz), 8.02(1H, dd, J = 8.1, 1.7Hz), 8.64(1H, d, J = 1.7Hz), 10.04(1H, brs), 10.52(1H, s), 10.81(1H, s). FAB-MS: 442(M + H)⁺ |
| 13 | 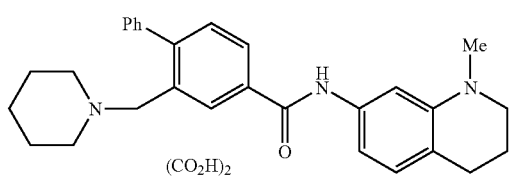 | NMR: δ1.33-1.45(2H, br), 1.46-1.57(4H, m), 1.84-1.93 (2H, m), 2.43-2.69(7H, m), 2.84(3H, s), 3.19(2H, t, J = 5.6Hz), 3.94(2H, brs), 6.85(1H, d, J = 8.3Hz), 7.01-7.08 (2H, m), 7.39-7.54(6H, m), 8.02(1H, d, J = 7.3Hz), 8.21 (1H, s), 10.05(1H, s). FAB-MS: 440(M + H)⁺ |
| 14 | 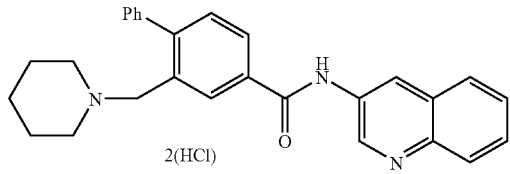 | NMR: δ1.20-1.36(1H, m), 1.52-1.66(3H, m), 1.81-1.97 (2H, m), 2.58-2.70(2H, m), 3.18-3.31(2H, m), 4.42(2 H d, J = 5.3Hz), 7.39-7.46(2H, m), 7.47-7.59(4H, m), 7.73 (1H, t, J = 7.8Hz), 7.82(1H, t, J = 7.8Hz), 8.07-8.17(3 H m), 8.90(1H, s), 9.20(1H, s), 9.57(1H, s), 10.21(1H, brs), 11.43(1H, s). FAB-MS: 422(M + H)⁺ |
| 15 | 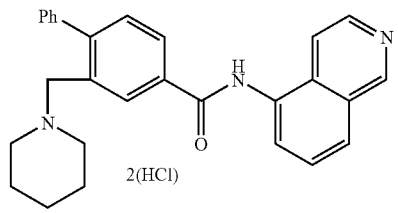 | NMR: δ1.20-1.35(1H, m), 1.52-1.65(3H, m), 1.76-1.92 (2H, m), 2.56-2.68(2H, m), 3.18-3.28(2H, m), 4.41(2 H d, J = 4.9Hz), 7.41-7.46(2H, m), 7.48-7.60(4H, m), 7.85-7.93(1H, m), 8.00(1H, d, J = 7.3Hz), 8.02-8.22(3H, m), 8.93(1H, s), 9.10-9.18(1H, m), 9.21(1H, d, J = 3.9Hz), 10.34(1H, brs), 11.112(1H, s). FAB-MS: 422(M + H)⁺ |

TABLE 13-continued

| Ex | Structure(salt) | DATA |
|---|---|---|
| 16 | (2-methylpiperidin-1-yl)methyl-4-phenyl-N-(1,3-benzothiazol-5-yl)benzamide 2(HCl) | NMR: δ1.03-1.95(6H, m), 2.21-2.74(1H, m), 2.96-3.04 (1H, m), 3.18-3.50(1H, m), 3.96-4.05(1H, m), 4.10-4.40 (2H, br), 4.91-4.99(1H, m), 7.39-7.59(6H, m), 8.08 (2H, d, J = 8.3Hz), 8.15(1H, d, J = 8.8Hz), 8.79(2H, brs), 9.41(1H, s), 10.00(1H, br), 10.26(1H, br), 10.89(1H, s, ). FAB-MS: 442(M + H)⁺ |
| 17 | (3,6-dihydro-2H-pyridin-1-yl)methyl-4-phenyl-N-(1,3-benzothiazol-5-yl)benzamide HCl | NMR: 1.95-2.09(1H, m), 2.32-2.52(1H, m), 2.86-2.99 (1H, m), 3.24-3.38(2H, m), 3.56-3.68(1H, m), 4.49(2 H d, J = 5.4Hz), 5.45-5.55(1H, m), 5.70-5.80(1H, m), 7.39-7.58(6H, m), 8.02(1H, d, J = 8.8, 2.0Hz), 8.10(1H, dd, J = 7.8, 1.5Hz), 8.16(1H, d, J = 8.3Hz), 8.70-8.80(2H, m), 9.41(1H, s), 10.55(1H, brs), 10.81(1H, s). FAB-MS: 426(M + H)⁺ |

TABLE 14

| Ex | Structure(salt) | DATA |
|---|---|---|
| 18 | (3,4-dihydro-1H-isoquinolin-2-yl)methyl-4-phenyl-N-(1,3-benzothiazol-5-yl)benzamide HCl | NMR: δ2.75-2.85(1H, m), 3.07-3.26(2H, m), 3.47-3.59 (1H, m), 3.98-4.08(1H, m), 4.27-4.36(1H, m), 4.52-4.64(2H, brs), 7.08(1H, d, J = 7.3Hz), 7.13(1H, d, J = 7.4Hz), 7.15-7.25(2H, m), 7.53(5H, m), 7.56(1H, d, J = 8.3Hz), 7.97(1H, d, J = 8.8Hz), 8.14(2H, d, J = 8.8Hz), 8.73(2H.s.), 9.40(1H, s), 10.77(2H, brs). FAB-MS: 476(m + H)⁺ |
| 19 | (pyrrolidin-1-yl)methyl-4-phenyl-N-(1,3-benzothiazol-5-yl)benzamide HCl | NMR: δ1.72-1.91(4H, m), 2.70-2.82(2H, m), 3.33-3.42 (2H, m), 4.48(2H, d, J = 5.9Hz), 7.39-7.58(6H, m), 8.03-8.11(2H, m), 8.15(1H, d, J = 8.8Hz), 8.74-8.82(2H, m), 9.42(1H, s), 10.78-10.89(2H, m). FAB-MS: 414 (M + H)⁺ |
| 20 | (azepan-1-yl)methyl-4-phenyl-N-(1,3-benzothiazol-5-yl)benzamide HCl | NMR: δ1.35-1.59(6H, m), 1.60-1.73(2H, m), 2.79-2.90 (2H, m), 3.20-3.32(2H, m), 4.42(2H, d, J = 5.4Hz), 7.38-7.44(2H, m), 7.47-7.58(4H, m), 8.03-8.11(2H, m), 8.16(1H, d, J = 8.8Hz), 8.79(2H, s), 9.41(1H, s), 10.36 (1H, br), 10.83(1H, s). FAB-MS: 442(M + H)⁺ |
| 21 | (morpholin-4-yl)methyl-4-phenyl-N-(1,3-benzothiazol-5-yl)benzamide HCl | NMR: δ2.73-2.90(2H, m), 3.25(2H, d, J = 12.3Hz), 3.72-3.94(4H, m), 4.00-4.60(2H, m), 7.36-7.58(6H, m), 8.01-8.11(2H, m), 8.15(1H, d, J = 8.8Hz), 8.72-8.82 (2H, m), 9.41(1H, s), 10.74-10.89(2H, m). FAB-MS: 430(M + H)⁺ |
| 22 | (3-acetamidopyrrolidin-1-yl)methyl-4-phenyl-N-(1,3-benzothiazol-5-yl)benzamide HCl | NMR: δ1.69-1.84(4H, m), 2.08-2.20(1H, m), 2.48-2.72 (1H, m), 2.76-2.98(1H, m), 3.06-3.30(1H, m), 3.42-3.71(1H, m), 3.30-4.60(3H, m), 7.38-7.58(6H, m), 8.00-8.30(4H, m), 8.69(1H, d, J = 9.8Hz), 8.77(1H, d, J = 1.4Hz), 9.42(1H, s), 10.66-10.95(2H, m). FAB-MS: 471(M + H)⁺ |

TABLE 14-continued

| Ex | Structure(salt) | DATA |
|----|-----------------|------|
| 23 | 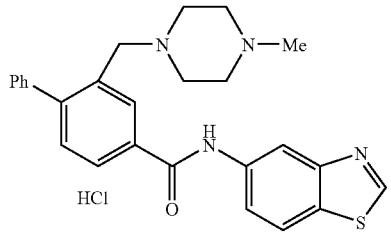 | NMR: δ2.75(3H, m), 3.00-4.40(10H, m), 7.40-7.58 (6H, m), 7.95-8.08(2H, m), 8.15(1H, d, J = 8.8Hz), 8.49 (1H, brs), 8.73(1H, s), 9.41(1H, s), 10.68(1H, s). FAB-MS: 443(M + H)+ |
| 24 | 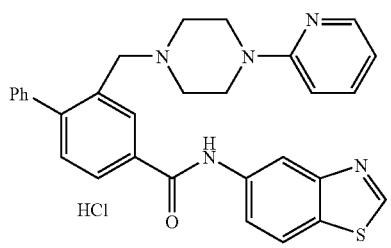 | NMR: δ3.33-3.50(2H, m), 3.54-3.80(2H, m), 4.25-4.40 (2H, m), 4.49(2H, d, J = 5.4Hz), 4.52(2H, s), 6.82-6.92(1H, m), 7.06-7.18(1H, m), 7.38-7.57(6H, m), 7.77-7.90(1H, m), 8.03-8.12(3H, m), 8.16(1H, d, J = 8.8 Hz), 8.78-8.88(2H, m), 9.42(1H, s), 10.86(1H, s), 11.10 (1H, brs). FAB-MS: 506(M + H)+ |
| 25 | 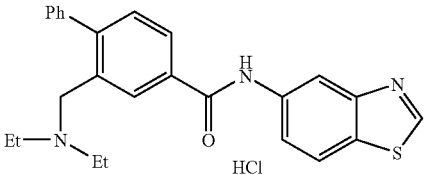 | NMR: δ0.99(H, t, J = 7.3Hz), 2.76-2.89(2H, m), 2.97-3.10(2H, m), 4.43(2H, d, J = 5.3Hz), 7.42-7.59(6H, m), 8.04-8.11(2H, m), 8.15(1H, d, J = 8.8Hz), 8.74-8.81 (2H, m), 9.41(1H, s), 10.30(1H, brs), 10.89(1H, s). FAB-MS: 416(M + H)+ |
| 26 | 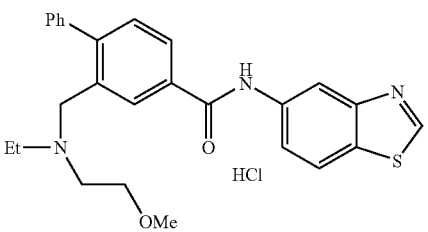 | NMR: δ1.00(3H, t, J = 7.3Hz), 2.78-3.28(7H, m), 3.57-3.63(2H, m), 4.44-4.60(2H, m), 7.39-7.59(6H, m), 8.04-8.11(2H, m), 8.15(1H, d, J = 8.8Hz), 8.76-8.81(2H, m), 9.42(1H, s), 10.44(1H, brs), 10.87(1H, s). FAB-MS: 446(M + H)+ |

TABLE 15

| Ex | Structure(salt) | DATA |
|----|-----------------|------|
| 27 |  | NMR: δ1.01(3H, t, J = 7.3Hz), 2.60-2.78(1H, m), 2.79-2.92(1H, m), 4.20-4.60(4H, m), 7.35-7.62(11H, m), 8.04-8.11(2H, m), 8.17(1H, d, J = 8.8Hz), 8.73(1H, d, J = 1.4Hz), 8.80(1H, d, J = 1.9Hz), 9.42(1H, s), 10.66(1H, brs), 10.90(1H, s). FAB-MS: 478(M + H)+ |
| 28 | 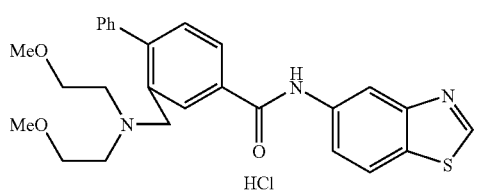 | NMR: δ3.11-3.22(10H, m), 3.50-3.63(4H, m), 4.60(2 H d, J = 4.9Hz), 7.38-7.60(6H, m), 8.04(1H, dd ,J = 8.8, 1.9Hz), 8.11(1H, dd, J = 7.8, 2.0Hz), 8.16(1H, d, J = 8.8 Hz), 8.70-8.80(2H, m), 9.42(1H, s), 10.33(1H, brs), 10.82 (1H, s). FAB-MS: 476(M + H)+ |

TABLE 15-continued

| Ex | Structure(salt) | DATA |
|---|---|---|
| 29 | (Ph-substituted benzamide with 3-methylpiperidinyl-methyl group, N-benzothiazol-5-yl, HBr salt) | NMR: δ0.67-0.80(3H, m), 0.91-1.03(1H, m), 1.40-1.78 (3H, m), 1.80-1.95(1H, m), 2.18-2.30(1H, m), 2.53-3.30(2H, m), 4.33-4.60(2H, m), 7.40-7.44(2H, m), 7.46-7.59(5H, m), 7.97(1H, dd, J = 8.8, 1.9Hz), 8.13-8.19 (2H, m), 8.57(1H, s), 8.73(1H, d, J = 2.0Hz), 9.43(2 H s), 10.63-10.67(1H, m). FAB-MS: 442(M + H)+ |
| 30 | (Ph-substituted benzamide with 4-methylpiperidinyl-methyl group, N-benzothiazol-5-yl, HBr salt) | NMR: δ0.70-0.86(3H, m), 1.30-1.72(5H, m), 2.57-2.70 (1.5H, m). 2.88-3.04(0.5H, m), 3.20-3.29(2H, m), 4.37-4.59(2H, m), 7.39-7.60(6H, m), 7.93(1H, d, J = 8.3Hz), 8.14-8.19(2H, m), 8.50(1H, s), 8.71(1H, s), 9.21 (0.8H, brs), 9.42(1H, m), 9.52(0.2H, brs), 10.63-10.67 (1H, m). FAB-MS: 442(M + H)+ |
| 31 | (Ph-substituted benzamide with 2,6-dimethylpiperidinyl-methyl group, N-benzothiazol-5-yl, HBr salt) | NMR: δ1.04-1.23(7H, m), 1.33-1.80(5H, m), 3.23-3.41 (1H, m), 3.41-3.56(1H, m), 4.41(1.1H, m), 4.64(0.9 H s), 7.43-7.64(6H, m), 7.90-7.97(1H, m), 8.10-8.19 (2H, m), 8.71(1H, s), 8.47(0.4H, brs), 8.71(1H, s), 9.32 (0.6H, brs), 9.42(1H, s), 10.68-10.77(1H, m). FAB-MS: 456(M + H)+ |
| 32 | (Ph-substituted benzamide with 3,5-dimethylpiperidinyl-methyl group, N-benzothiazol-5-yl, HBr salt) | NMR: δ0.63-0.80(7H, m), 1.07-1.19(0.2H, br), 1.41-1.48(0.2H, m), 1.58-1.67(0.8H, m), 1.76-1.91(1.8H, br), 2.09-2.21(2H, m), 2.87-2.94(0.2H, m), 3.02-3.16 (1.8H, m), 4.42(1.8H, d, J = 5.4Hz), 4.56-4.61(0.2H, m), 7.40-7.45(2H, m), 7.47-7.60(4H, m), 7.91(1H, dd, J = 8.8, 2.0Hz), 8.14-8.21(2H, m), 8.44-8.50(1H, m), 8.70(1H, d, J = 2.0Hz), 8.32-8.46(1.8H, m), 9.80(0.2 H brs), 10.64(1H, s). FAB-MS: 456(M + H)+ |
| 33 | (Ph-substituted benzamide with N-iPr-cyclohexylamino-methyl group, N-benzothiazol-5-yl, HBr salt) | NMR: δ0.92-1.24(10H, m), 1.26-1.56(3H, m), 1.62-1.74 (3H, brs), 1.81-1.91(1H, m), 3.13-3.23(1H, m), 3.58-3.68(1H, m), 4.41-4.57(2H, m), 7.45-7.50(2H, m), 7.50-7.62(4H, m), 7.95(1H, d, J = 8.8Hz), 8.13-8.18(2H, m), 8.36(1H, s), 8.44(1H, brs), 8.72(1H, d, J = 1.9Hz), 9.42(1H, s), 10.74(1H, s). FAB-MS: 484(M + H)+ |
| 34 | (Ph-substituted benzamide with piperidinyl-methyl group, N-benzoxazol-2-one-5-yl, HCl salt) | NMR: δ1.24-1.32(1H, m), 1.54-1.62(3H, m), 1.74-1.88 (2H, m), 2.48-2.52(2H, m), 3.18-3.24(2H, m), 4.37 (2H, d, J = 5.4Hz), 7.28(1H, d, J = 8.8Hz), 7.38-7.43(2 H m), 7.46-7.57(4H, m), 7.58-7.62(1H, m), 7.87(1H, s), 8.02(1H, dd, J = 7.8, 1.4Hz), 8.69-8.72(1H, m), 10.11 (1H, brs), 10.66(1H, s), 11.68(1H, s). FAB-MS: 428 (M + H)+ |

TABLE 16

| Ex | Structure(salt) | DATA |
|---|---|---|
| 35 | [Structure: 4-Ph-benzamide with N-(benzothiazol-5-yl), 3-CH2-N(4-phenyl-4-hydroxypiperidine), HCl salt] | NMR: δ1.60-1.73(2H, m), 2.50-2.63(2H, m), 2.86-3.02 (2H, m), 3.21-3.40(2H, m), 4.44-4.74(2H, m), 5.28-5.45 (1H, m), 7.00-7.61(11H, m), 8.01-8.19(3H, m), 8.70-8.85(2H, m), 9.42(1H, s), 10.40-10.72(1H, m), 10.75-10.96(1H, m). FAB-MS: 520(M + H)+ |
| 36 | [Structure: 4-Ph-benzamide with N-(benzo[1,3]dioxol-5-yl), 3-CH2-piperidine, HCl salt] | NMR: δ1.20-1.34(1H, m), 1.52-1.63(3H, m), 1.73-1.89 (2H, m), 2.53-2.65(2H, m), 3.17-3.24(2H, m), 4.37(2 H d, J = 4.9Hz), 6.02(2H, s), 6.92(1H, d, J = 8.3Hz), 7.36-7.42(3H, m), 7.45-7.56(5H, m), 8.00(1H, d, J = 8.3Hz), 8.70(1H, s), 10.14(1H, brs), 10.52(1H, s). FAB-MS: 415(M + H)+ |
| 37 | [Structure: 4-Ph-benzamide with N-(quinolin-7-yl), 3-CH2-piperidine, 2(HBr) salt] | NMR: δ1.20-1.35(1H, m), 1.54-1.67(5H, m), 2.52-2.69 (2H, m), 3.16-3.26(2H, m), 4.41(2H, d, J = 5.4Hz), 7.40-7.45(2H, m), 7.49-7.60(4H, m), 7.78(1H, brs), 8.12-8.27(3H, m), 8.48(1H, s), 8.80(1H, brs), 8.91(1H, s), 9.10 (1H, s), 9.22(1H, brs), 11.03(1H, s). FAB-MS: 422(M + H)+ |
| 38 | [Structure: 4-Ph-benzamide with N-(2-oxo-2,3-dihydrobenzoxazol-6-yl), 3-CH2-piperidine, (CO2H)2 salt] | NMR: δ1.30-1.40(2H, m), 1.42-1.56(4H, m), 3.30-3.80 (6H, m), 7.09(1H, d, J = 7.7Hz), 7.40-7.52(7H, m), 7.85 (1H, d, J = 2.0Hz), 7.94-8.00(1H, m), 8.15(1H, brs), 10.38 (1H, s), 11.60(1H, s). FAB-MS: 428(M + H)+ |
| 39 | [Structure: 4-Ph-benzamide with N-(3-methyl-2-oxo-2,3-dihydrobenzoxazol-5-yl), 3-CH2-piperidine, HCl salt] | NMR: δ1.20-1.35(1H, m), 1.53-1.63(3H, m), 1.74-1.90 (2H, m), 2.54-2.66(2H, m), 3.18-3.24(2H, m), 3.33(3 H s), 4.38(2H, d, J = 5.4Hz), 7.34(1H, d, J = 8.8Hz), 7.38-7.42(2H, m), 7.46-7.57(4H, m), 7.63(1H, dd, J = 8.8, 1.9 Hz), 7.94(1H, d, J = 1.5Hz), 8.03(1H, dd, J = 8.8, 1.4Hz), 8.74(1H, s), 10.17(1H, brs), 10.74(1H, s). FAB-MS: 442 (M + H)+ |
| 40 | [Structure: 4-Ph-benzamide with N-(3-nitrophenyl), 3-CH2-piperidine, HCl salt] | NMR: δ1.20-1.35(1H, m), 1.53-1.65(3H, m), 1.72-1.88 (2H, m), 2.56-2.69(2H, m), 3.19-3.25(2H, m), 4.39(2 H d, J = 5.4Hz), 7.38-7.44(2H, m), 7.47-7.58(4H, m), 7.69 (1H, t, J = 8.3Hz), 7.96-8.02(1H, m), 8.04-8.11(1H, m), 8.35(1H, d, J = 7.8Hz), 8.71(1H, s), 8.95(1H, d, J = 2.0 Hz), 9.96(1H, brs), 11.11(1H, s). FAB-MS: 416(M + H)+ |
| 41 | [Structure: 4-Ph-benzamide with N-(1,1-dioxo-benzothiophen-6-yl), 3-CH2-piperidine, HBr salt] | NMR: δ1.20-1.35(1H, m), 1.52-1.66(5H, m), 2.55-2.68 (2H, m), 3.17-3.24(2H, m), 4.39(2H, d, J = 4.9Hz), 7.33 (1H, d, J = 6.8Hz), 7.39-7.44(2H, m), 7.48-7.58(4H, m), 7.61-7.66(2H, m), 8.04-8.09(1H, m), 8.12-8.17(1 H m), 8.34(1H, s), 8.43(1H, s), 9.20(1H, brs), 10.85(1 H s). FAB-MS: 459(M + H)+ |

TABLE 16-continued

| Ex | Structure(salt) | DATA |
|---|---|---|
| 42 | 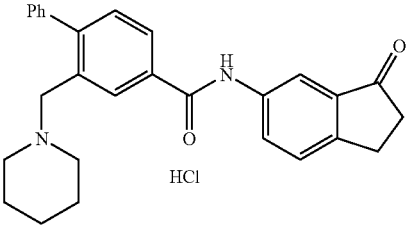 | NMR: δ1.20-1.35(1H, m), 1.56-1.64(3H, m), 1.72-1.86 (2H, m), 2.54-2.63(2H, m), 2.68(2H, t, J = 5.4Hz), 3.09 (2H, t, J = 5.4Hz), 3.18-3.24(2H, m), 4.37(2H, d, J = 5.4Hz), 7.38-7.45(2H, m), 7.46-7.57(4H, m), 7.59(1H, d, J = 8.8Hz), 8.05(1H, dd, J = 8.8, 2.0Hz), 8.16(1H, dd, J = 8.8, 2.0Hz), 8.29(1H, d, J = 1.9Hz), 8.71(1H, d, J = 1.4Hz), 10.06 (1H, brs), 10.82(1H, s). FAB-MS: 425(M + H)+ |

TABLE 17

| Ex | Structure(salt) | DATA |
|---|---|---|
| 43 | 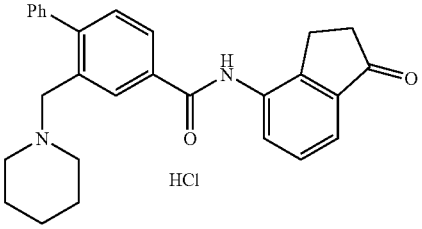 | NMR: δ1.20-1.33(1H, m), 1.53-1.63(3H, m), 1.72-1.86 (2H, m), 2.54-2.63(2H, m), 2.66-2.69(2H, m), 3.17-3.24(4H, m), 4.38(2H, d, J = 4.9Hz), 7.389-7.43(2 H m), 7.47-7.57(6H, m), 7.87(1H, d, J = 7.3Hz), 8.07 (1H, dd, J = 7.8, 1.4Hz), 8.74(1H, s), 10.15(1H, brs), 10.48 (1H, s). FAB-MS: 425(M + H)+ |
| 44 | 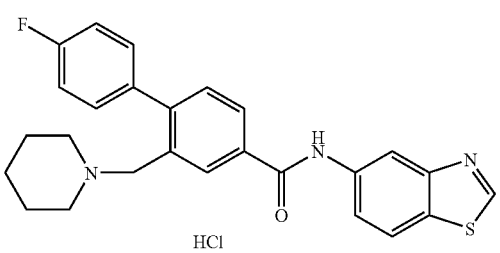 | NMR: δ1.22-1.36(1H, m), 1.55-1.66(3H, m), 1.77-1.92 (2H, m), 2.58-2.71(2H, m), 3.19-3.27(2H, m), 4.37 (2H, d, J = 5.4Hz), 7.33-7.41(2H, m), 7.43-7.52(3H, m), 8.03-8.09(2H, m), 8.15(1H, d, J = 8.8Hz), 8.75-8.80 (1H, m), 9.41(1H, s), 10.13(1H, brs), 10.88(1H, s). FAB-MS: 446(M + H)+ |
| 45 | 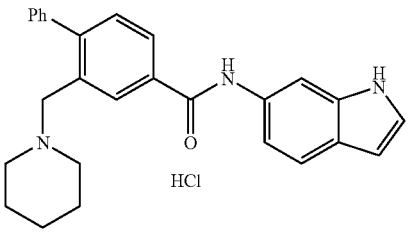 | NMR: δ1.21-1.34(1H, m), 1.53-1.63(3H, m), 1.76-1.90 (2H, m), 2.54-2.65(2H, m), 3.19-3.25(2H, m), 4.38 (2H, d, J = 4.9Hz), 6.37-6.41(1H, m), 7.28-7.57(9H, m), 8.00-8.07(1H, m), 8.21(1H, s), 8.74(1H, s), 10.29 (1H, brs), 10.48(1H, s), 11.10(1H, s). FAB-MS: 410 (M + H)+ |
| 46 | 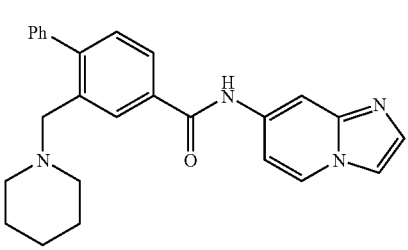 | NMR: δ1.27-1.38(1H, m), 1.38-1.54(5H, m), 2.22(4 H brs), 3.33-3.42(2H, m), 7.23(1H, dd, J = 7.5, 2.3Hz), 7.34-7.54(7H, m), 7.84(1H, s), 7.88-7.96(1H, m), 8.06(1H, d, J = 1.5Hz), 8.15(1H, s), 8.49(1H, d, J = 6.9Hz), 10.49(1H, s). FAB-MS: 411(M + H)+ |
| 47 | 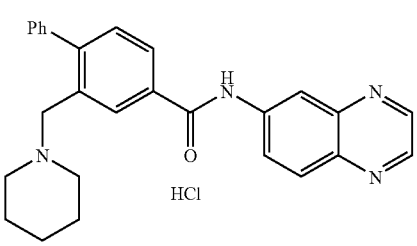 | NMR: δ1.21-1.35(1H, m), 1.54-1.64(3H, m), 1.77-1.92 (2H, m), 2.56-2.68(2H, m), 3.17-3.29(2H, m), 4.41 (2H, d, J = 4.9Hz), 7.38-7.45(2H, m), 7.47-7.58(4 H m), 8.05-8.15(2H, m), 8.39-8.46(1H, m), 8.79-8.84 (2H, m), 8.86(1H, d, J = 2.0Hz), 8.93(1H, d, J = 2.0Hz), 10.17(1H, brs), 1.15(1H, s). FAB-MS: 423(M + H)+ |

TABLE 17-continued

| Ex | Structure(salt) | DATA |
|---|---|---|
| 48 | 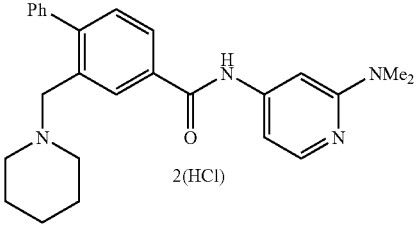 2(HCl) | NMR: δ1.20-1.36(1H, m), 1.52-1.65(3H, m), 1.79-1.96 (2H, m), 2.55-2.70(2H, m), 3.18-3.37(8H, m), 4.39 (2H, d, J = 5.3Hz), 7.37-7.63(7H, m), 7.85(1H, s), 7.97-8.07(2H, m), 8.86(1H, d, J = 1.5Hz), 10.14(1H, br s), 11.50(1H, s), 13.07(1H, brs). FAB-MS: 415(M + H)+ |
| 49 | 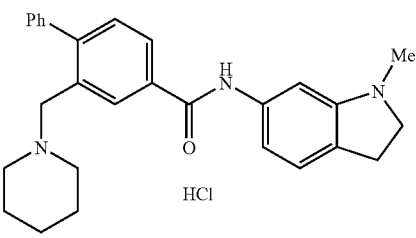 HCl | NMR: δ1.16-1.35(1H, m), 1.50-1.66(3H, m), 1.74-1.97 (2H, m), 2.54-2.65(2H, m), 2.77(3H, s), 2.85-2.97 (2H, m), 3.14-3.27(2H, m), 3.33-3.542(2H, m), 4.37(2H, d, J = 4.4Hz), 7.09(1H, d, J = 8.3Hz), 7.27-7.60(8 H m), 8.00(1H, d, J = 8.3Hz), 8.72(1H, s), 10.27(1H, brs), 10.46(1H, s). FAB-MS: 426(M + H)+ |
| 50 | 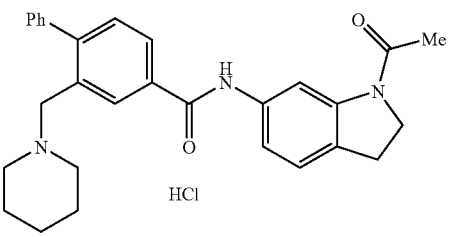 HCl | NMR: δ1.21-1.34(1H, m), 1.52-1.64(3H, m), 1.65-1.83 (2H, m), 2.17(3H, s), 2.55-2.60(2H, m), 3.06-3.28 (4H, m), 4.07-4.16(2H, m), 4.36(2H, d, J = 4.8Hz), 7.20 (1H, d, J = 8.3Hz), 7.37-7.57(7H, m), 8.06(1H, d, J = 7.9Hz), 8.57(2H, s), 9.93(1H, brs), 10.45(1H, s). FAB-MS: 454(M + H)+ |

TABLE 18

| Ex | Structure(salt) | DATA |
|---|---|---|
| 51 | 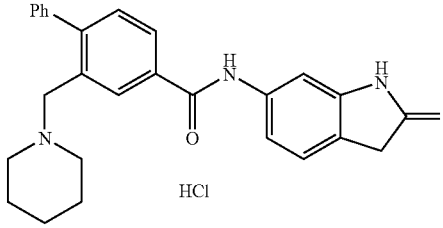 HCl | NMR: δ1.20-1.35(1H, m), 1.52-1.64(3H, m), 1.80-1.95 (2H, m), 2.53-2.66(2H, m), 3.19-3.25(2H, m), 3.44 (2H, s) 4.37(2H, d, J = 5.4Hz), 7.15-7.19(1H, m), 7.38-7.41(2H, m), 7.45-7.56(5H, m), 7.68(1H, brs), 7.97-8.01(1H, m), 8.78(1H, s), 10.46(2H, m), 10.62(1H, s). FAB-MS: 426(M + H)+ |
| 52 | 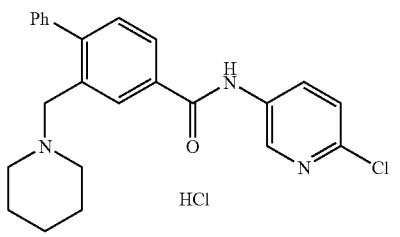 HCl | NMR(300 MHz, DMSO-d6): δ1.20-1.37(1H, m), 1.52-1.65(3H, m), 1.77-1.95(2H, m), 2.54-2.69(2H, m), 3.17-3.28(2H, m), 4.39(2H, d, J = 5.1Hz), 7.38-7.60(7H, m), 8.03(1H, dd ,J = 8.1, 1.7Hz), 8.43(1H, dd, J = 8.6, 2.7Hz), 8.81(1H, d, J = 1.5Hz), 9.02(1H, d, J = 2.6Hz), 10.16(1H, brs), 11.10(1H, s). FAB-MS: 406(M + H)+ |
| 53 | 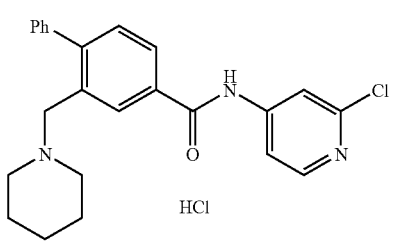 HCl | NMR: δ1.20-1.32(1H, m), 1.53-1.63(3H, m), 1.78-1.90(2H, m), 2.58-2.63(2H, m), 3.18-3.26(2H, m), 4.38 (2H, d, J = 5.2Hz), 7.37-7.58(6H, m), 7.94-7.98(1H, m), 8.04(1H, dd, J = 7.8, 1.5Hz), 8.11(1H, d, J = 2.3Hz), 8.35(1H, d, J = 5.3Hz), 8.76(1H, s), 10.02(1H, brs), 11.26 (1H, s). FAB-MS: 406(M + H)+ |

TABLE 18-continued

| Ex | Structure(salt) | DATA |
|---|---|---|
| 54 | 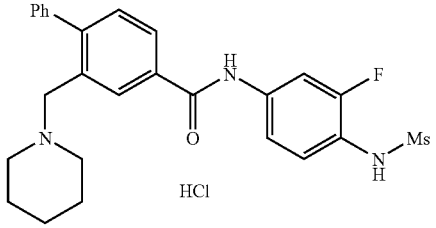 | NMR: δ1.20-1.36(1H, m), 1.52-1.64(3H, m), 1.77-1.93 (2H, m), 2.54-2.68(2H, m), 3.02(3H, s), 3.16-3.28 (2H, m), 4.38(2H, d, J = 4.8Hz), 7.34-7.57(7H, m), 7.77 (1H, dd, J = 8.8, 2.0Hz), 7.96-8.05(2H, m), 8.77(1H, s), 9.50(1H, s), 10.20(1H, brs), 10.89(1H, s). FAB-MS: 482(M + H)$^+$ |
| 55 | 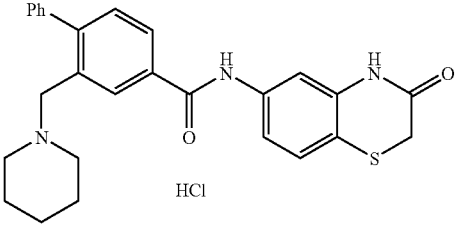 | NMR: δ1.20-1.35(1H, m), 1.52-1.64(3H, m), 1.80-1.95 (2H, m), 2.53-2.66(2H, m), 3.19-3.24(2H, m), 3.45 (2H, s), 4.37(2H, d, J = 5.4Hz), 7.28-7.32(1H, m), 7.38-7.41(2H, m), 7.45-7.56(5H, m), 7.84-7.85(1H, m), 7.98-8.02(1H, m), 8.74-8.77(1H, m), 10.37(1H, br s), 10.66(1H, s), 10.69(1H, s). FAB-MS: 458(M + H)$^+$ |
| 56 | 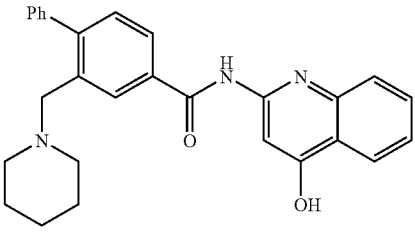 | NMR(CDCl$_3$): δ1.30-1.61(6H, m), 2.20-2.50(4H, m), 3.44(2H, s), 5.09(2H, brs), 6.86(1H, s), 7.21-7.62 (8H, m), 7.71(1H, d, J = 8.4Hz), 7.88(1H, d, J = 8.3Hz), 8.19(1H, dd, J = 8.1, 1.8Hz), 8.51(1H, d, J = 1.6Hz). FAB-MS: 438(M + H)$^+$ |
| 57 | 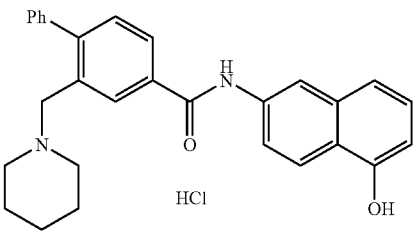 | NMR: δ1.20-1.35(1H, m), 1.52-1.64(3H, m), 1.77-1.94 (2H, m), 2.53-2.68(2H, m), 3.10-3.40(2H, m), 4.39 (2H, d, J = 4.9Hz), 6.77-6.85(1H, m), 7.24-7.58(8H, m), 7.95(1H, dd, J = 8.8, 2.0Hz), 8.03-8.13(2H, m), 8.49 (1H, d, J = 2.0Hz), 8.79(1H, d, J = 2.6Hz), 10.12(1H, s), 10.29(1H, brs), 10.78(1H, s). FAB-MS: 437(M + H)$^+$ |
| 58 | 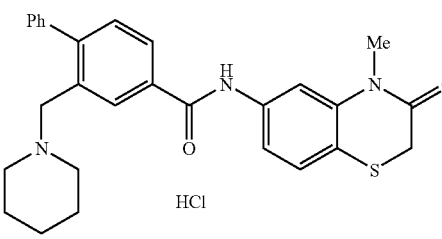 | NMR: δ1.20-1.35(1H, m), 1.52-1.64(3H, m), 1.80-1.95 (2H, m), 2.55-2.66(2H, m), 3.19-3.26(2H, m), 3.35 (3H, s), 3.52(2H, s), 4.38(2H, d, J = 4.8Hz), 7.38-7.42 (3H, m), 7.46-7.56(4H, m), 7.74-7.79(1H, m), 7.98-8.04(2H, m), 8.78-8.82(1H, m), 10.25(1H, brs), 10.80-10.81(1H, m). FAB-MS: 472(M + H)$^+$ |

TABLE 19

| Ex | Structure(salt) | DATA |
|---|---|---|
| 59 | 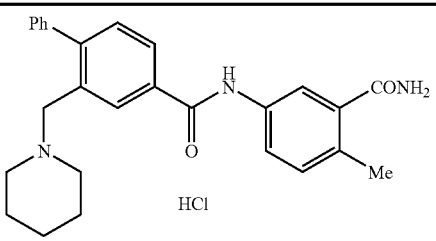 | NMR: δ1.20-1.35(1H, m), 1.52-1.64(3H, m), 1.80-1.95 (2H, m), 2.33(3H, s), 2.54-2.64(2H, m), 3.17-3.26(2 H m), 4.37(2H, d, J = 4.9Hz), 7.19-7.23(1H, m), 7.36-7.42 (3H, m), 7.46-7.56(4H, m), 7.69(1H, brs), 7.84-7.88 (1H, m), 7.98-8.02(2H, m), 8.77(1H, brs), 10.37(1H, m), 10.66(1H, s). FAB-MS: 428(M + H)$^+$ |

TABLE 19-continued

| Ex | Structure(salt) | DATA |
|---|---|---|
| 60 | 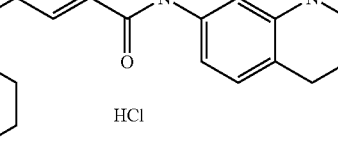 | NMR: δ1.20-1.35(1H, m), 1.52-1.64(3H, m), 1.76-1.90 (2H, m), 2.42-2.48(2H, m), 2.54-2.64(2H, m), 2.81-2.87 (2H, m), 3.17-3.24(2H, m), 4.37(2H, d, J = 5.4Hz), 7.12-7.15(1H, m), 7.34-7.42(3H, m), 7.46-7.56(4H, m), 7.64-7.66(1H, m), 7.99-8.03(1H, m), 8.71-8.74(1H, m), 10.16(1H, s), 10.34(1H, brs), 10.55(1H, s). FAB-MS: 440(M + H)$^+$ |
| 61 | 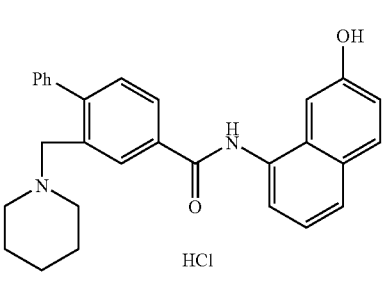 | NMR: δ1.27-1.52(6H, m), 2.16-2.34(4H, m), 3.39(2H, s), 7.11(1H, dd, J = 8.8, 1.9Hz), 7.22(1H, dd, J = 2.0Hz), 7.28-7.52(8H, m), 7.75(1H, d, J = 7.8Hz), 7.83(1H, d, J = 8.8Hz), 8.06(1H, d, J = 7.9Hz), 8.17(1H, s), 9.75(1H, s), 10.32(1H, s). FAB-MS: 437(M + H)$^+$ |
| 62 | 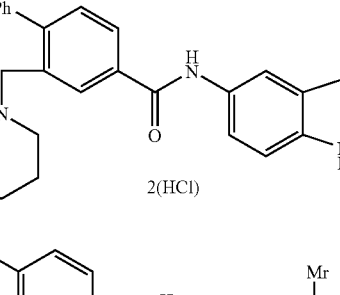 | NMR: δ1.20-1.30(1H, m), 1.54-1.64(3H, m), 1.84-1.97 (2H, m), 2.54-2.66(2H, m), 3.16-3.28(2H, m), 4.39(2 H d, J = 5.4Hz), 5.00(2H, brs), 7.38-7.57(7H, m), 7.87-7.93(1H, m), 8.00-8.05(1H, m), 8.07-8.10(1H, m), 8.42-8.45(1H, m), 8.82-8.87(1H, m), 10.40(1H, brs), 10.68 (1H, s). FAB-MS: 411(M + H)$^+$ |
| 63 | 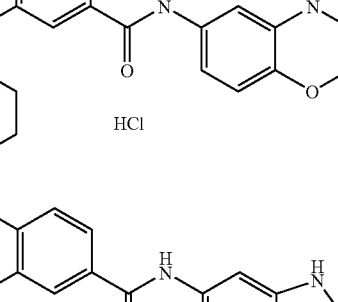 | NMR: δ1.21-1.37(1H, m), 1.50-1.66(3H, m), 1.77-1.95 (2H, m), 2.55-2.67(2H, m), 3.18-3.30(2H, m), 3.28(3 H s), 4.39(2H, d, J = 5.4Hz), 4.65(2H, s), 7.01(1H, d, J = 8.8Hz), 7.38-7.58(6H, m), 7.67(1H, dd, J = 8.6, 2.0Hz), 7.89(1H, d, J = 2.2Hz), 7.99-8.06(1H, m), 8.77-8.81(1H, m), 10.24 (1H, brs), 10.69(1H, s). FAB-MS: 456(M + H)$^+$ |
| 64 | 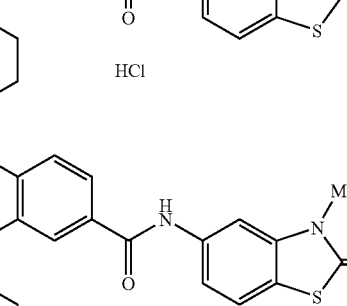 | NMR: δ1.20-1.35(1H, m), 1.52-1.64(3H, m), 1.76-1.92 (2H, m), 2.54-2.65(2H, m), 3.18-3.26(2H, m), 4.38(2 H d, J = 5.4Hz), 7.38-7.42(2H, m), 7.46-7.56(5H, m), 7.65-7.70(1H, m), 8.00-8.04(2H, m), 8.77(1H, s), 10.32 (1H, s), 10.76(1H, s), 11.96(1H, brs). FAB-MS: 444(M + H)$^+$ |
| 65 | 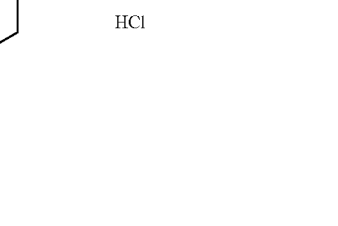 | NMR: δ1.20-1.35(1H, m), 1.52-1.65(3H, m), 1.80-1.95 (2H, m), 2.56-2.66(2H, m), 3.20-3.26(2H, m), 3.40(3 H s), 4.39(2H, d, J = 5.4Hz), 7.38-7.42(2H, m), 7.46-7.56 (4H, m), 7.60-7.64(1H, m), 7.80-7.86(1H, m), 8.01-8.05(1H, m), 8.07-8.10(1H, m), 8.80-8.82(1H, m), 10.29 (1H, s), 10.86(1H, s). FAB-MS: 458(M + H)$^+$ |

TABLE 19-continued

| Ex | Structure(salt) | DATA |
|---|---|---|
| 66 | 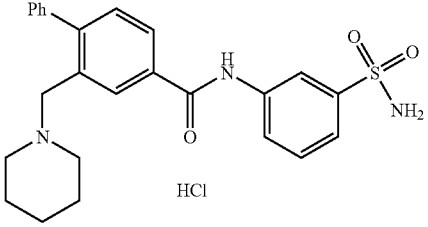 HCl | NMR: δ1.22-1.33(1H, m), 1.54-1.62(3H, m), 1.73-1.88 (2H, m), 2.55-2.65(2H, m), 3.18-3.24(2H, m), 4.38(2 H d, J = 4.9Hz), 7.36-7.43(3H, m), 7.48-7.61(7H, m), 8.10-8.05(2H, m), 8.56(1H, s), 8.74(1H, s), 10.19(1H, brs), 10.92(1H, s). FAB-MS: 450(M + H)$^+$ |

TABLE 20

| Ex | Structure(salt) | DATA |
|---|---|---|
| 67 | 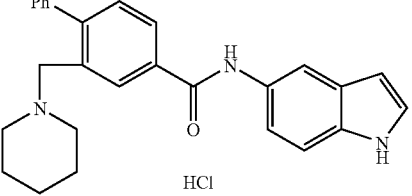 HCl | NMR: δ1.21-1.34(1H, m), 1.52-1.64(3H, m), 1.75-1.92 (2H, m), 2.53-2.65(2H, m), 3.16-3.26(2H, m), 4.38 (2H, d, J = 5.4Hz), 6.39-6.43(1H, m), 7.43-7.61(9H, m), 8.01-8.06(1H, m), 8.15(1H, s), 8.75(1H, s), 10.32(1 H brs), 10.41(1H, s), 11.07(1H, s). FAB-MS: 410(M + H)$^+$ |
| 68 | 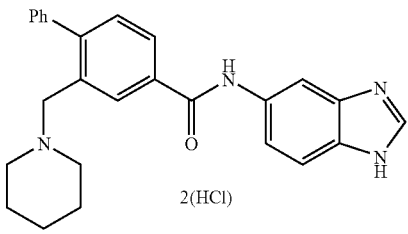 2(HCl) | NMR: δ1.21-1.34(1H, m), 1.56-1.62(3H, m), 1.80-1.96 (2H, m), 2.58-2.68(2H, m), 3.10-3.70(4H, m), 4.34-4.44(2H, m), 7.38-7.58(6H, m), 7.82-7.88(1H, m), 8.00-8.25(2H, m), 8.67(1H, s), 8.84-8.90(1H, m), 9.46-9.53(1H, m), 10.38(1H, brs), 11.06(1H, s). FAB-MS: 411(M + H)$^+$ |
| 69 | 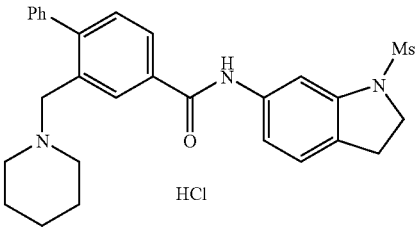 HCl | NMR: δ1.19-1.35(1H, m), 1.52-1.63(3H, m), 1.72-1.89 (2H, m), 2.55-2.63(2H, m), 3.02(3H, s), 3.07-3.11(2H, m), 3.18-3.22(2H, m), 3.92-4.00(2H, m), 4.37(2H, d, J = 4.9Hz), 7.24(1H, d, J = 8.3Hz), 7.36-7.59(7H, m), 8.00(1H, s), 8.04(1H, dd, J = 8.3, 1.5Hz), 8.70(1H, s), 10.19(1H, brs), 10.62(1H, s). FAB-MS: 490(M + H)$^+$. |
| 70 | 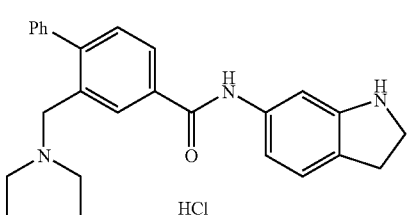 HCl | NMR: δ1.19-1.36(1H, m), 1.51-1.64(3H, m), 1.79-1.96 (2H, m), 2.54-2.66(2H, m), 3.14-3.24(4H, m), 3.71-3.75(2H, m), 4.38(2H, d, J = 4.8Hz), 7.39-7.56(7H, m), 7.90(1H, d, J = 8.3Hz), 8.02(1H, dd, J = 7.8, 1.5Hz), 8.14(1H, s), 8.81(1H, s), 10.32(1H, brs), 10.90(1H, s). FAB-MS: 412(M + H)$^+$ |
| 71 | 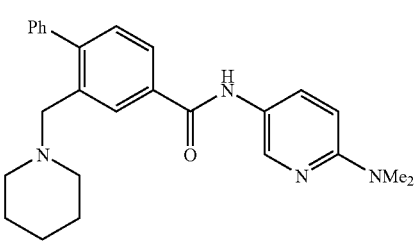 | NMR(CDCl$_3$): δ1.20-1.38(1H, m), 1.55-1.85(3H, m), 2.08-2.55(4H, m), 3.35-3.52(8H, m), 4.49(2H, d, J = 5.1 Hz), 6.77(1H, d, J = 9.6Hz), 7.25-7.55(5H, m), 8.02(1H, dd, J = 8.1, 1.5Hz), 8.57(1H, dd, J = 9.5, 2.2Hz), 8.91 (1H, s), 9.16(1H, d, J = 2.2Hz), 10.50-10.72(2H, m), FAB-MS: 415(M + H)$^+$ |

TABLE 20-continued

| Ex | Structure(salt) | DATA |
|---|---|---|
| 72 | Ph-benzyl-piperidine-benzamide-N-benzotriazole, 2(HCl) | NMR: δ1.20-1.33(1H, m), 1.53-1.64(3H, m), 1.80-1.95 (2H, m), 2.55-2.68(2H, m), 3.18-3.30(2H, m), 4.40 (2H, d, J = 5.4Hz), 4.70(2H, brs), 7.38-7.58(6H, m), 7.94-8.17(3H, m), 8.63(1H, s), 8.82-8.86(1H, m), 10.37 (1H, brs), 10.93(1H, s). FAB-MS: 412(M + H)$^+$ |
| 73 | Ph-benzyl-piperidine-benzamide-N-benzazepinone, HCl | NMR: δ1.20-1.35(1H, m), 1.53-1.63(3H, m), 1.75-1.90 (2H, m), 2.05-2.20(4H, m), 2.54-2.70(4H, m), 3.15-3.26(2H, m), 4.37(2H, d, J = 5.3Hz), 7.21-7.24(1H, m), 7.38-7.42(2H, m), 7.46-7.56(4H, m), 7.58-7.62(1 H m), 7.68-7.72(1H, m), 7.99-8.03(1H, m), 8.70-8.72 (1H, m), 9.60(1H, s), 10.23(1H, s), 10.61(1H, s). FAB-MS: 454(M + H)$^+$ |
| 74 | Ph-benzyl-piperidine-benzamide-N-(N-Me-benzazepinone), HCl | NMR: δ1.20-1.35(1H, m), 1.53-1.63(3H, m), 1.80-1.95 (2H, m), 2.00-2.10(2H, m), 2.14-2.22(2H, m), 2.55-2.66(4H, m), 3.18-3.25(5H, m), 4.37(2H, d, J = 4.9Hz), 7.23-7.27(1H, m), 7.38-7.42(2H, m), 7.46-7.56(4 H m), 7.75-7.80(1H, m), 7.95-7.97(1H, m), 8.00-8.04 (1H, m), 8.79(1H, brs), 10.27(1H, s), 10.72(1H, s). FAB-MS: 468(M + H)$^+$ |

TABLE 21

| Ex | Structure(salt) | DATA |
|---|---|---|
| 75 | Ph-benzyl-piperidine-benzamide-N-(2-NMe$_2$-benzothiazole), HCl | NMR: δ1.20-1.35(1H, m), 1.52-1.65(3H, m), 1.80-1.95 (2H, m), 2.54-2.66(2H, m), 3.15-3.30(8H, m), 4.39 (2H, d, J = 4.9Hz), 7.38-7.42(2H, m), 7.46-7.56(4H, m), 7.74-7.84(2H, m), 8.00-8.04(1H, m), 8.22-8.30(1 H m), 8.76-8.84(1H, m), 10.31(1H, s), 10.79(1H, s). FAB-MS: 471(M + H)$^+$ |
| 76 | Ph-benzyl-piperidine-benzamide-N-(OMe, CONH$_2$ phenyl) | NMR: δ1.30-1.39(2H, m), 1.42-1.51(4H, m), 2.19-2.30 (4H, m), 3.38(2H, s), 3.86(3H, s), 6.75(1H, dd, J = 8.8, 2.4Hz), 7.38-7.49(6H, m), 7.65(1H, s), 7.85-7.89(1H, m), 7.91(1H, d, J = 8.8Hz), 8.13(1H, d, J = 1.5Hz), 8.27 (1H, s), 8.45(1H, d, J = 2.5Hz), 13.48(1H, s). FAB-MS: 444(M + H)$^+$ |
| 77 | Ph-benzyl-piperidine-benzamide-N-(Cl, CONH$_2$ phenyl) | NMR: δ1.29-1.39(2H, m), 1.39-1.49(4H, m), 2.17-2.28 (4H, m), 3.39(2H, s), 7.37-7.54(8H, m), 7.75-7.82(2H, m), 7.93(1H, d, J = 7.9Hz), 8.01(1H, d, J = 1.9Hz), 8.07 (1H, s), 10.52(1H, s). FAB-MS: 448(M + H)$^+$ |

TABLE 21-continued

| Ex | Structure(salt) | DATA |
|---|---|---|
| 78 | | NMR: δ1.20-1.35(1H, m), 1.52-1.64(3H, m), 1.76-1.92 (2H, m), 2.52-2.65(4H, m), 2.80-2.87(2H, m), 3.12-3.25(5H, m), 4.38(2H, d, J = 4.9Hz), 7.18-7.22(1H, m), 7.36-7.42(2H, m), 7.44-7.56(4H, m), 7.62-7.68(1H, m), 7.78(1H, s), 8.00-8.06(1H, m), 8.74(1H, s), 10.14 (1H, brs), 10.64(1H, s). FAB-MS: 454(M + H)+ |
| 79 | | NMR: δ1.20-1.35(1H, m), 1.52-1.64(3H, m), 1.80-1.96 (2H, m), 2.54-2.66(2H, m), 3.12(3H, s), 3.18-3.26(2H, m), 3.57(2H, s) 4.39(2H, d, J = 4.9Hz), 7.20-7.26(1H, m), 7.36-7.42(2H, m), 7.46-7.56(4H, m), 7.58-7.62 (1H, m), 7.70-7.74(1H, m), 7.98-8.05(1H, m), 8.77-8.82(1H, m), 10.36(1H, s), 10.69(1H, s). FAB-MS: 440(M + H)+ |
| 80 | | NMR: δ1.20-1.35(1H, m), 1.52-1.64(3H, m), 1.80-1.95 (2H, m), 2.54-2.66(2H, m), 3.18-3.26(2H, m), 3.77 (3H, s) 4.38(2H, d, J = 4.9Hz), 6.39(1H, d, J = 2.9Hz), 7.28-7.30(1H, m), 7.38-7.42(2H, m), 7.46-7.60(6H, m), 8.01-8.06(1H, m), 8.20(1H, s), 8.80(1H, s), 10.39(1 H brs), 10.57(1H, s). FAB-MS: 424(M + H)+ |
| 81 | | NMR: δ1.28(7H, brs), 1.52-1.64(3H, m), 1.80-1.95(2 H m), 2.54-2.66(2H, m), 3.14(3H, s), 3.18-3.26(2H, m), 4.38(2H, d, J = 5.3Hz), 7.30-7.34(1H, m), 7.38-7.42 (2H, m), 7.46-7.56(4H, m), 7.58-7.64(1H, m), 7.73 (1H, m), 8.00-8.04(1H, m), 8.81(1H, s), 10.38(1H, br s), 10.69(1H, s). FAB-MS: 468(M + H)+ |
| 82 | | NMR: δ1.18-1.33(1H, m), 1.52-1.67(5H, m), 2.53-2.65 (2H, m), 3.14-3.20(2H, m), 4.37(2H, d, J = 4.9Hz), 7.40-7.46(2H, m), 7.47-7.59(4H, m), 7.67-7.72(1H, m), 7.97-8.01(2H, m), 8.03(1H, d, J = 2.5Hz), 8.40-8.44 (1H, m), 8.57(1H, s), 8.71(1H, d, J = 9.3Hz), 9.72(1H, brs), 12.95(1H, s). FAB-MS: 448(M + H)+ |

TABLE 22

| Ex | Structure(salt) | DATA |
|---|---|---|
| 83 | 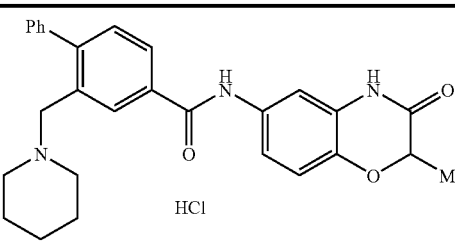 | NMR: δ1.20-1.34(1H, m), 1.42(3H, d, J = 6.8Hz), 1.53-1.62(3H, m), 1.71-1.86(2H, m), 2.53-2.65(2H, m), 3.14-3.24(2H, m), 4.37(2H, d, J = 5.4Hz), 4.63(1H, q, J = 6.9 Hz), 6.95(1H, d, J = 8.3Hz), 7.34-7.42(3H, m), 7.45-7.57 (4H, m), 7.68(1H, d, J = 2.4Hz), 7.99-8.05(1H, m), 8.65 (1H, s), 10.08(1H, brs), 10.52(1H, s,), 10.75(1H, s). FAB-MS: 456(M + H)+ |

TABLE 22-continued

| Ex | Structure(salt) | DATA |
|---|---|---|
| 84 | 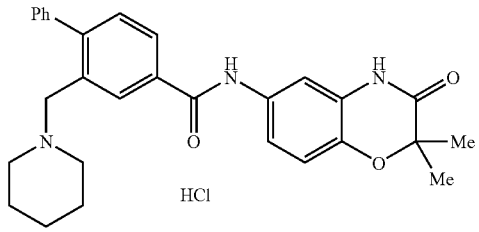 HCl | NMR: δ1.21-1.35(1H, m), 1.40(6H, s), 1.52-1.63(3H, m), 1.74-1.91(2H, m), 2.54-2.65(2H, m), 3.15-3.26(2H m), 4.37(2H, d, J = 5.4Hz), 6.93(1H, d, J = 8.3Hz), 7.34-7.43(3H, m), 7.45-7.57(4H, m), 7.68-7.72(1H, m), 7.98-8.03(1H, s), 8.68-8.73(1H, m), 10.26(1H, brs), 10.55 (1H, s), 10.70(1H, s). FAB-MS: 470(M + H)$^+$ |
| 85 | 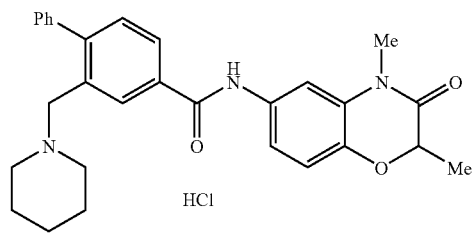 HCl | NMR: δ1.20-1.34(1H, m), 1.44(3H, d, J = 6.8Hz), 1.52-1.63(3H, m), 1.77-1.92(2H, m), 2.54-2.67(2H, m), 3.18-3.25(2H, m), 3.28(3H, s), 4.38(2H, d, J = 5.4Hz), 4.71 (1 H, q, J = 6.6Hz), 7.02(1H, d, J = 6.8Hz), 7.40(2H, d, J = 7.3Hz), 7.45-7.57(4H, m), 7.62-7.67(1H, m), 7.86(1H, d, J = 1.9Hz), 8.03(1H, d, J = 8.8Hz), 8.75(1H, s,) 10.15 (1H, brs), 10.65(1H, s). FAB-MS: 470(M + H)$^+$ |
| 86 | 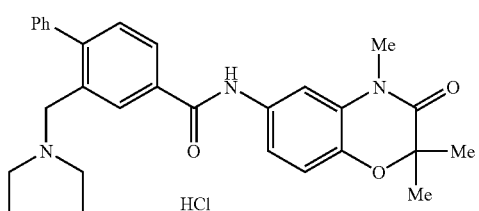 HCl | NMR: δ1.22-1.34(1H, m), 1.42(6H, s), 1.52-1.64(3H, m), 1.78-1.94(2H, m), 2.55-2.67(2H, m), 3.17-3.26(2 H m), 3.29(3H, s), 4.38(2H, d, J = 4.9Hz), 6.99(1H, d, J = 8.8Hz), 7.37-7.43(2H, m), 7.45-7.57(4H, m), 7.63-7.69 (1H, m), 7.86(1H, d, J = 1.9Hz), 7.98-8.05(1H, m), 8.78 (1H, s), 10.23(1H, brs), 10.66(1H, s). FAB-MS: 484(M + H)$^+$ |
| 87 | 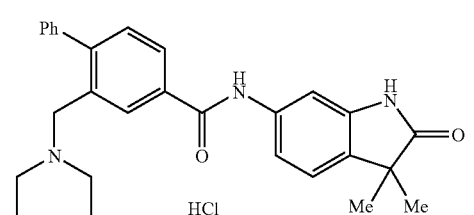 HCl | NMR: δ1.25(7H, brs), 1.52-1.64(3H, m), 1.78-1.92(2 H m), 2.53-2.66(2H, m), 3.18-3.25(2H, m), 4.38(2H, d, J = 5.4Hz), 7.22-7.26(1H, m), 7.38-7.42(2H, m), 7.46-7.57(5H, m), 7.65-7.66(1H, m), 7.98-8.03(1H, m), 8.73-8.75(1H, s), 10.32(1H, brs), 10.40(1H, s), 10.58(1H, s). FAB-MS: 454(M + H)$^+$ |
| 88 | 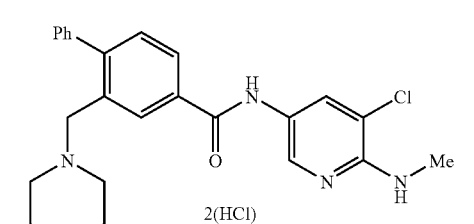 2(HCl) | NMR: δ1.20-1.36(1H, m), 1.50-1.65(3H, m), 1.78-1.96 (2H, m), 2.55-2.69(2H, m), 2.98(3H, s), 3.15-3.28(2 H m), 4.38(2H, d, J = 5.4Hz), 7.36-7.58(6H, m), 8.02(1 H dd, J = 7.8, 1.5Hz), 8.44(1H, s), 8.64(1H, d, J = 3.5Hz), 8.81(1H, d, J = 1.5Hz), 10.15(1H, brs), 10.92(1H, s). FAB-MS: 435(M + H)$^+$ |
| 89 | 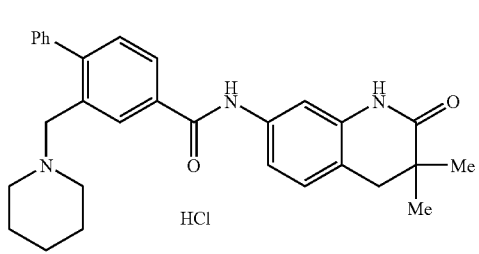 HCl | NMR: δ1.07(6H, s), 1.20-1.35(1H, m), 1.53-1.62(3H, m), 1.74-1.88(2H, m), 2.53-2.65(2H, m), 2.72(2H, s), 3.18-3.25(2H, m), 4.38(2H, d, J = 5.4Hz), 7.10-7.15(1H, m), 7.33-7.42(3H, m), 7.46-7.57(4H, m), 7.61-7.63(1 H m), 7.98-8.04(1H, m), 8.68-8.70(1H, m), 10.10(1H, brs), 10.24(1H, s), 10.53(1H, s). FAB-MS: 468(M + H)$^+$ |

TABLE 22-continued

| Ex | Structure(salt) | DATA |
|---|---|---|
| 90 | (structure) HCl | NMR: δ1.21-1.36(1H, m), 1.54-1.64(3H, m), 1.76-1.92 (2H, m), 2.56-2.66(2H, m), 3.19-3.26(2H, m), 4.38(2 H d, J = 5.4Hz), 7.02-7.07(1H, m), 7.38-7.57(6H, m), 8.02 (1H, dd, J = 8.1, 2.0Hz), 8.05-8.11(1H, m), 8.28(1H, d, J = 1.5Hz), 8.78(1H, d, J = 1.5Hz), 10.18(1H, brs), 10.84 (1H, s), 11.23(1H, brs) FAB-MS: 462(M + H)+ |

TABLE 23

| Ex | Structure(salt) | DATA |
|---|---|---|
| 91 | (structure) HCl | NMR: δ1.80-2.38(4H, m), 2.40-2.48(2H, m), 2.65-2.90 (4H, m), 3.18-3.32(2H, m), 4.36-4.50(2H, m), 4.60-5.02 (1H, m), 7.10-7.17(1H, m), 7.32-7.37(1H, m), 7.38-7.42(2H, m), 7.46-7.56(4H, m), 7.60-7.64(1H, m), 8.00-8.04(1H, m), 8.62-8.67(1H, m), 10.17(1H, s), 10.04-10.53(2H, m). FAB-MS: 458(M + H)+ |
| 92 | (structure) HCl | NMR: δ1.88-2.34(4H, m), 2.52-2.58(2H, m), 2.72-2.88 (4H, m), 3.24-3.27(5H, m), 4.38-4.49(2H, m), 4.60-5.20 (1H, m), 7.18-7.23(21 , m), 7.38-7.42(2H, m), 7.46-7.56(4H, m), 7.62-7.68(1H, m), 7.74-7.78(1H, m), 8.01-8.06(1H, m), 8.65-8.70(1H, m), 10.34(1H, s), 10.59(1H, s). ESI-MS: 472(M + H)+ |
| 93 | (structure) HCl | NMR: δ1.50-1.80(2H, br), 1.80-2.10(2H, br), 2.42-2.48 (2H, m), 2.52-2.55(1H, m), 2.80-2.2.88(3H, m), 3.85-4.75(4H, br), 7.10-7.17(1H, m), 7.28-7.33(1H, m), 7.40-7.55(8H, m), 7.98-8.08(1H, m), 8.51(1H, br), 10.18(1H, s), 10.42(1H, brs). FAB-MS: 476(M + H)+ |
| 94 | (structure) HCl | NMR: δ1.50-2.25(4H, br), 2.52-2.56(4H, m), 2.82-2.86 (2H, m), 3.22-3.75(5H, m), 4.20-5.00(2H, br), 7.17-7.23 (1H, m), 7.41-7.57(6H, m), 7.58-7.62(1H, m), 7.74(1H, s), 8.02-8.09(1H, m), 8.50-8.80(1H, br), 10.59(1H, brs), 10.80-11.20(1H, br). FAB-MS: 490(M + H)+ |

TABLE 23-continued

| Ex | Structure(salt) | DATA |
|---|---|---|
| 95 | 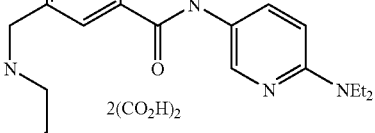 2(CO$_2$H)$_2$ | NMR: δ1.11(6H, t, J = 5.9Hz), 1.30-1.50(2H, m), 1.50-1.64 (4H, m), 2.55-3.00(4H, m), 3.49(4H, q, J = 14.2, 6.9 Hz), 4.20(2H, brs), 6.62(1H, d, J = 9.3Hz), 7.37-7.56(6 H m), 7.84(1H, dd, J = 9.3, 2.9Hz), 8.06(1H, dd, J = 7.9, 1.5 Hz), 8.39(1H, s), 8.42(1H, d, J = 2.5Hz), 10.22(1H, s). FAB-MS: 443(M + H)$^+$. |
| 96 | 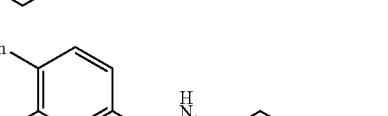 2(CO$_2$H)$_2$ | NMR: δ1.20-1.65(12H, m), 2.48-2.85(4H, m), 3.44-3.52 (4H, m), 4.02(2H, s), 6.85(1H, d, J = 9.2Hz), 7.38-7.55 (6H, m), 7.89(1H, dd, J = 8.8, 2.5Hz), 8.00-8.07(1H, m), 8.28(1H, s), 8.47(1H, d, J = 2.9Hz), 10.25(2H, s). FAB-MS: 455(M + H)$^+$ |
| 97 | 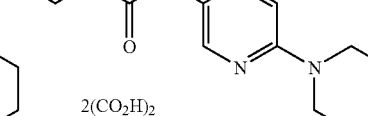 (CO$_2$H)$_2$ | NMR: δ1.30-1.59(6H, m), 2.48-2.75(4H, m), 3.83-4.06 (5H, m), 6.87(1H, d, J = 8.8Hz), 7.37-7.55(6H, m), 8.01-8.11(2H, m), 8.28(1H, s), 8.56(1H, d, J = 2.9Hz), 10.43 (1H, m). FAB-MS: 402(M + H)$^+$ |
| 98 | 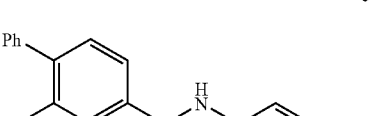 (CO$_2$H)$_2$ | NMR: δ1.30-1.47(2H, m), 1.47-1.62(4H, m), 2.55-2.81 (7H, m), 3.50-4.70(2H, m), 6.50(1H, d, J = 8.8Hz), 7.37-7.56(6H, m), 7.76(1H, dd, J = 8.8, 2.4Hz), 8.04(1H, d, J = 7.8Hz), 8.31(1H, s), 8.35(1H, d, J = 2.4Hz), 10.17(1 H s). FAB-MS: 401(M + H)$^+$ |
| 99 | 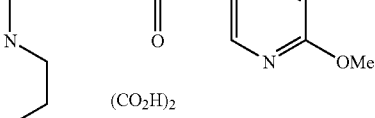 | ESI-MS: 411(M + H)$^+$ |

TABLE 24

| Ex | Structure(salt) | DATA |
|---|---|---|
| 100 | 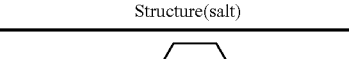 HCl | NMR: δ1.60-2.05(4H, m), 2.18-2.90(3H, m), 3.08-3.38 (2H, m), 4.34-4.46(2H, m), 6.86(1H, brs), 7.24-7.58 (7H, m), 8.04-8.18(3H, m), 8.76-8.81(2H, m), 9.41(1H, s), 10.17-10.52(1H, m), 10.89(1H, s). FAB-MS: 471 (M + H)$^+$ |

TABLE 24-continued
| Ex | Structure(salt) | DATA |
|---|---|---|
| 101 | 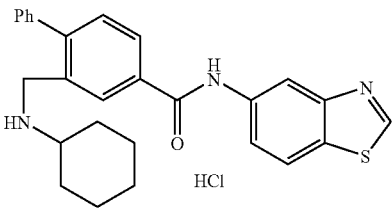 | NMR: δ 0.98-1.36(5H, m), 1.50-1.60(1H, m), 1.62-1.73 (2H, m), 1.82-1.92(2H, m), 2.80-2.95(1H, m), 4.17-4.26(2H, m), 7.44-7.58(6H, m), 8.00-8.18(3H, m), 8.67-8.79(2H, m), 9.22(2H, brs), 9.41(1H, s), 10.81 (1H, brs). FAB-MS: 442(M + H)$^+$ |
| 102 | 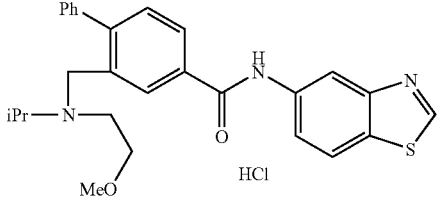 | NMR: δ 0.81(3H, d, J = 6.8Hz), 1.17(3H, d, J = 6.8Hz), 2.95-3.85(8H, m), 4.45-4.59(2H, m), 7.42-7.60(6H, m), 8.01-8.18(3H, m), 8.67-8.79(2H, m), 9.41(1H, s), 9.74 (1H, brs), 10.90(1H, brs). FAB-MS: 460(M + H)$^+$ |
| 103 | 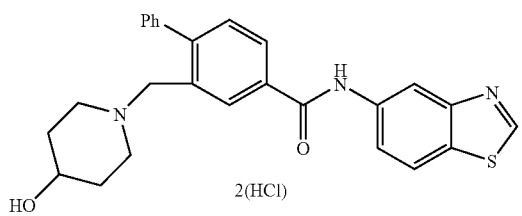 | NMR: δ 1.48-2.14(4H, m), 2.60-2.86(2H, m), 3.02-3.90 (2H, m), 4.25-4.45(3H, m), 4.45-4.59(2H, m), 7.36-7.58(6H, m), 8.02-8.18(3H, m), 8.77-8.88(2H, m), 9.42(1H, s), 10.32-10.53(1H, m), 10.87-10.94(1H, m). FAB-MS: 444(M + H)$^+$ |
| 104 | 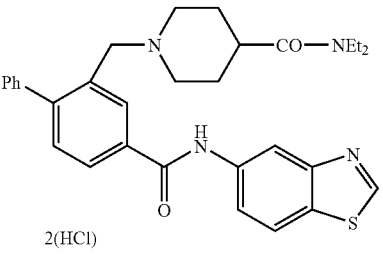 | NMR: δ 0.90-1.09(6H, m), 1.33-1.70(2H, m), 1.72-2.10 (2H, m), 2.65-3.02(3H, m), 3.12-3.34(6H, m), 4.34-4.51(2H, m), 7.36-7.70(6H, m), 8.01-8.18(3H, m), 8.74-8.84(2H, m), 9.42(1H, s), 10.28(1H, brs), 10.88 (1H, s). FAB-MS: 527(M + H)$^+$ |
| 105 | 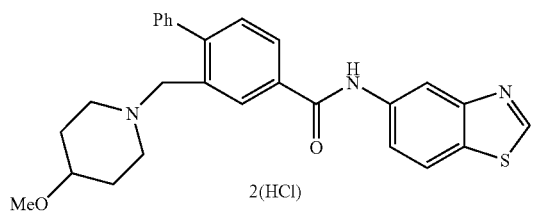 | NMR: δ 1.73-2.14(4H, m), 2.60-2.80(2H, m), 3.06-3.52 (6H, m), 4.38-4.45(2H, m), 7.37-7.58(6H, m), 8.02-8.18(3H, m), 8.78-8.85(2H, m), 9.41(1H, s), 10.50(1H, brs), 10.86-10.92(1H, m). FAB-MS: 458(M + H)$^+$ |
| 106 | 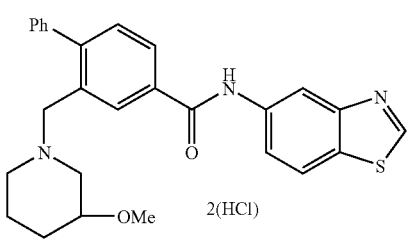 | NMR: δ 1.11-2.00(4H, m), 2.48-2.85(2H, m), 3.02-3.58 (6H, m), 4.25-4.58(2H, m), 7.38-7.59(6H, m), 7.92-8.22(3H, m), 8.62-8.84(2H, m), 9.40-9.43(1H, m), 10.56(1H, brs), 10.73-10.88(1H, m). FAB-MS: 458(M + H)$^+$ |

TABLE 24-continued

| Ex | Structure(salt) | DATA |
| --- | --- | --- |
| 107 | [structure] | NMR(CDCl₃): δ1.10-1.91(10H, m), 2.37-3.20(9H, m), 3.36-3.54(2H, m), 7.27-7.47(6H, m), 7.84-7.97(3H, m), 8.12(1H, d, J = 1.8Hz), 8.48(1H, s), 8.74-9.03(2H, m). FAB-MS: 511(M + H)⁺ |
| 108 | [structure] 2(HCl) | NMR: δ1.30-2.45(10H, m), 2.70-3.52(9H, m), 4.35-4.63 (2H, m), 7.38-7.59(6H, m), 8.03-8.18(3H, m), 8.74-8.86(1H, m), 9.42(1H, s), 10.65-10.98(2H, m). FAB-MS: 511(M + H)⁺ |

TABLE 25

| Ex | Structure(salt) | DATA |
| --- | --- | --- |
| 109 | [structure] HCl | NMR: δ2.85-3.00(2H, m), 3.34-3.50(4H, m), 3.65-3.75 (2H, m), 4.50-4.60(2H, m), 7.06(1H, dd, J = 7.8, 4.4Hz), 7.40-7.58(6H, m),7.82(1H, dd, J = 7.8, 1.4Hz), 8.02-8.24(4H, m), 8.75-8.82(2H, m), 9.41(1H, s), 10.73(1H, brs), 10.85(1H, s). FAB-MS: 540(M + H)⁺ |
| 110 | [structure] 2(HCl) | NMR: δ1.89-2.40(4H, m), 2.70-2.90(2H, m), 3.17-3.40 (2H, m), 4.38-4.52(2H, m), 4.58-5.04(1H, m), 7.36-7.58 (6H, m), 8.01-8.18(3H, m), 8.76-8.86(2H, m), 9.42 (1H, s), 10.68(1H, brs), 10.83-10.92(1H, m). FAB-MS: 446(M + H)⁺ |
| 111 | [structure] HCl | NMR: δ1.55-2.10(4H, m), 2.46-5.00(6H, m), 7.40-7.58 (6H, m), 7.94-8.18(3H, m), 8.48-8.79(2H, m), 9.41(1 H s), 10.79(2H, brs). FAB-MS: 464(M + H)⁺ |

TABLE 25-continued

| Ex | Structure(salt) | DATA |
|---|---|---|
| 112 | Ph-benzyl-piperidine-CH2-benzamide-N-(4-methyl-3-oxo-1,1-dioxo-benzothiazine) · HCl | NMR: δ1.20-1.35(1H, m), 1.53-1.65(3H, m), 1.78-1.94 (2H, m), 2.55-2.67(2H, m), 3.15-3.25(2H, m), 3.43(3 H s), 4.38(2H, d, J = 5.4Hz), 4.80(2H, s), 7.38-7.42(2 H m), 7.46-7.57(4H, m), 7.88-7.92(1H, m), 8.03-8.12 (2H, m), 8.25(1H, s), 8.81(1H, s), 10.08(1H, brs), 11.17 (1H, s). FAB-MS: 504(M + H)⁺ |
| 113 | Ph-benzyl-piperidine-CH2-benzamide-N-naphthalene-SO2NH2 · HCl | NMR: δ1.21-1.35(1H, m), 1.55-1.65(3H, m), 1.74-1.91 (2H, m), 2.56-2.68(2H, m), 3.20-3.28(2H, m), 4.40(2 H d, J = 4.9Hz), 7.40-7.67(9H, m), 8.02-8.22(4H, m), 8.58-8.80(3H, s), 10.11(1H, brs), 10.96(1H, s). FAB-MS: 500(M + H)⁺ |
| 114 | Ph-benzyl-piperidine-CH2-benzamide-N-(hydroxy-indanyl) · HCl | NMR: δ1.20-1.35(1H, m), 1.52-1.64(3H, m), 1.72-1.86 (3H, m), 2.31-2.40(1H, m), 2.57-2.62(2H, m), 2.64-2.73(1H, m), 2.84-2.92(1H, m), 3.16-3.24(2H, m), 4.37 (2H, d, J = 4.9Hz), 5.04(1H, t, J = 6.4Hz), 5.27(1H, br s), 7.20(1H, d, J = 8.3Hz), 7.37-7.42(2H, m), 7.45-7.56 (4H, m), 7.69(1H, dd, J = 8.8, 2.0Hz), 7.94(1H, s), 8.03 (1H, dd, J = 8.8, 2.0Hz), 8.66(1H, s), 10.11(1H, brs), 10.50 (1H, s). FAB-MS: 427(M + H)⁺ |
| 115 | Ph-benzyl-(iPr)2N-CH2-benzamide-N-benzothiazole · 2(HCl) | NMR: δ0.87(12H, t, J = 6.6Hz), 1.92-2.04(2H, m), 2.68-2.74(4H, m), 4.55(2H, d, J = 5.4Hz), 7.43-7.47(2H, m), 7.48-7.60(4H, m), 8.04-8.10(1H, m), 8.13-8.18(2 H m), 8.79(1H, s), 8.86(1H, brs), 9.42(1H, s), 9.54(1H, brs), 10.95(1H, s). FAB-MS: 472(M + H)⁺ |
| 116 | Ph-benzyl-morpholine(CO-NEt2)-CH2-benzamide-N-(1-methyl-2-oxo-tetrahydroquinoline) · HCl | NMR: δ0.94-1.02(3H, m), 1.06-1.14(3H, m), 2.52-2.58 (2H, m), 2.78-3.08(4H, m), 3.10-3.40(9H, m), 3.90-3.98 (1H, m), 4.00-4.14(1H, m), 4.45-4.65(2H, m), 4.80-4.92(1H, br), 7.18-7.22(1H, m), 7.36-7.44(2H, m), 7.46-7.58(4H, m), 7.62-7.68(1H, m), 7.79(1H, brs), 7.98-8.04(1H, m), 8.74(1H, br), 10.56(1H, s), 11.04(1H, br). FAB-MS: 555(M + H)⁺ |

TABLE 26

| Ex | Structure(salt) | DATA |
|---|---|---|
| 117 | Ph-benzyl-morpholine(CO-NEt2)-CH2-benzamide-N-(1-methyl-2-oxo-tetrahydroquinoline) · HCl | NMR: δ1.02-1.20(6H, m), 2.52-2.58(2H, m), 2.60-2.72 (1H, m), 2.80-2.90(2H, m), 2.90-3.04(1H, m), 3.26(3 H s), 3.28-3.70(5H, m), 3.73-3.83(1H, m), 3.88-3.98(1H, m), 4.00-4.10(1H, m), 4.15-4.28(1H, br), 4.33-4.45 (1H, m), 4.62-5.12(1H, br), 7.18-7.22(1H, m), 7.38-7.42 (2H, m), 7.44-7.58(4H, m), 7.58-7.62(1H, m), 7.77 (1H, brs), 8.05-8.12(1H, m), 8.42(1H, s), 10.00-10.55 (1H, br), 10.80(1H, s). FAB-MS: 555(M + H)⁺ |

TABLE 26-continued

| Ex | Structure(salt) | DATA |
|---|---|---|
| 118 | Ph-[benzene]-CH2-N(piperidine-3-CO-NEt2)-... -C(O)NH-[7-position of 1-methyl-3,4-dihydroquinolin-2(1H)-one]  HCl | NMR: δ 0.93-1.01(3H, m), 1.04-1.12(3H, m), 1.35-1.50 (1H, m), 1.56-1.76(3H, m), 1.90-2.05(1H, m), 2.52-2.58 (2H, m), 2.62-2.72(1H, m), 2.76-2.88(3H, m), 3.08-3.28(8H, m), 3.42-3.54(1H, m), 4.42-4.52(2H, m), 7.18-7.24(1H, m), 7.34-7.44(2H, m), 7.46-7.60(4H, m), 7.64-7.68(1H, m), 7.82-7.84(1H, m), 7.98-8.12(1H, m), 8.79(1H, s), 10.52(1H, br), 10.64(1H, s). FAB-MS: 553(M + H)$^+$ |
| 119 | Ph-[benzene]-CH2-N(pyrrolidine-2-CO-NEt2)-... -C(O)NH-[7-position of 1-methyl-3,4-dihydroquinolin-2(1H)-one] | NMR: δ 0.86-0.92(6H, m), 1.57-1.84(3H, m), 1.95-2.08 (1H, m), 2.36-2.44(1H, m), 2.52-2.58(2H, m), 2.80-2.88 (2H, m), 2.90-2.98(1H, m), 3.08-3.23(4H, m), 3.27 (3H, s), 3.43-3.48(1H, m), 3.63-3.77(2H, m), 7.18-7.22 (1H, m), 7.34-7.37(1H, m), 7.38-7.52(6H, m), 7.63(1 H s), 7.85-7.91(1H, m), 8.14(1H, s), 10.23(1H, s). FAB-MS: 539(M + H)$^+$ |
| 120 | Ph-[benzene]-CH2-N(piperidine-3-CF3)-... -C(O)NH-[7-position of 1-methyl-3,4-dihydroquinolin-2(1H)-one]  HBr | NMR: δ 1.30-1.50(1H, m), 1.60-1.90(3H, m), 2.52-2.58 (2H, m), 2.60-2.70(1H, br), 2.82-2.95(4H, m), 3.15-3.27 (4H, m), 3.37-3.48(1H, m), 4.35-4.70(2H, m), 7.18-7.24(1H, m), 7.37-7.42(2H, m), 7.47-7.58(5H, m), 7.65 (1H, s), 8.07-8.18(1H, m), 8.48(1H, brs), 9.48-9.66 (1H, br), 10.40(1H, s). FAB-MS: 522(M + H)$^+$ |
| 121 | Ph-[benzene]-CH2-N(piperidine-3-NHC(O)nPr)-... -C(O)NH-[7-position of 1-methyl-3,4-dihydroquinolin-2(1H)-one]  (CO2H)2 | NMR: δ 0.80(3H, t, J = 7.3Hz), 1.15-1.25(1H, m), 1.40-1.52(3H, m), 1.60-1.70(2H, m), 1.84-1.94(1H, m), 2.00 (2H, t, J = 7.3Hz), 2.04-2.20(1H, m), 2.52-2.58(2H, m), 2.62-2.81(2H, m), 2.82-2.88(2H, m), 3.26(3H, s), 3.64-3.80(3H, br), 7.18-7.24(1H, m), 7.38-7.52(7H, m), 7.59-7.65(2H, m), 7.95-8.02(1H, m), 8.17(1H, s), 10.34 (1H, s). FAB-MS: 539(M + H)$^+$ |
| 122 | Ph-[benzene]-CH2-N(piperidin-3-yl-(4-methylpiperidine))-... -C(O)NH-[6-position of 2-methyl-2,3-dihydro-4H-benzo[1,4]oxazin-3-one]  (CO2H)2 | NMR: δ 0.88(3H, d, J = 6.4Hz), 1.25-1.45(4H, m), 1.42 (3H, d, J = 6.9Hz), 1.50-1.63(1H, m), 1.65-1.73(3H, m), 1.83-1.93(2H, m), 2.04-2.12(1H, m), 2.55-2.62(1 H m), 2.77-2.95(3H, m), 3.07-3.19(1H, m), 3.20-3.33 (2H, m), 3.52(2H, s), 4.63(1H, q, J = 6.8Hz), 6.95(1H, d, J = 8.3Hz), 7.27(1H, dd, J = 8.8, 2.5Hz), 7.37-7.55(7H, m), 7.92(1H, dd, J = 6.8, 2.0Hz), 8.06(1H, d, J = 2.0Hz), 10.27(1H, s), 10.75(1H, s). FAB-MS: 553(M + H)$^+$ |
| 123 | Ph-[benzene]-CH2-N(Et)(CH2-C(Me)2-OH)-... -C(O)NH-[6-position of 2-methyl-2,3-dihydro-4H-benzo[1,4]oxazin-3-one]  (CO2H)2 | NMR: δ 0.81(3H, t, J = 6.8Hz), 1.04(6H, s), 1.42(3H, d, J = 6.4Hz), 2.36(2H, brs), 2.90-4.20(3H, m), 3.82(2H, br s), 4.63(1H, q, J = 6.8Hz), 6.94(1H, d, J = 8.8Hz), 7.25(1 H dd, J = 8.8, 2.5Hz), 7.31-7.38(3H, m), 7.39-7.52(3H, m), 7.58(1H, d, J = 2.4Hz), 7.91(1H, d, J = 7.7Hz), 8.28 (1H, s), 10.24(1H, s), 10.71(1H, s). FAB-MS: 488(M + H)$^+$ |

TABLE 27

| Ex | Structure (salt) | DATA |
|---|---|---|
| 124 | Ph-benzyl with piperidinylmethyl, amide linked to N-ethyl-3,4-dihydroquinolin-2(1H)-one at 7-position; HCl | NMR: δ 1.21 (3H, t, J = 6.8Hz), 1.18-1.34 (1H, m), 1.52-1.66 (3H, m), 1.76-1.94 (2H, m), 2.50-2.65 (4H, m), 2.78-2.85 (2H, m), 3.18-3.25 (2H, m), 3.88 (2H, q, J = 6.8Hz), 4.38 (2H, d, J = 5.3Hz), 7.20 (1H, d, J = 5.3Hz), 7.35-7.58 (6H, m), 7.65-7.72 (1H, m), 7.85 (1H, s), 7.95-8.07 (1H, m), 8.79 (1H, s), 10.23 (1H, brs), 10.67 (1H, s). FAB-MS: 468 (M + H)+ |
| 125 | Ph-benzyl with piperidinylmethyl, amide linked to N-(2-fluoroethyl)-3,4-dihydroquinolin-2(1H)-one at 7-position; HCl | NMR: δ 1.21-1.34 (1H, m), 1.54-1.64 (3H, m), 1.72-1.86 (2H, m), 2.55-2.63 (4H, m), 2.82-2.89 (2H, m), 3.18-3.26 (2H, m), 4.20 (2H, dt, J = 22.9, 5.4Hz), 4.38 (2H, d, J = 5.4Hz), 4.67 (2H, dt, J = 47.4, 5.4Hz), 7.22 (1H, d, J = 8.3Hz), 7.37-7.57 (6H, m), 7.63 (1H, ddd, J = 7.8, 2.0, 1.5Hz), 7.84 (1H, d, J = 1.5Hz), 8.05 (1H, ddd, J = 7.8, 2.0, 1.5Hz), 8.70 (1H, d, J = 1.5Hz), 9.99 (1H, brs), 10.60 (1H, s). FAB-MS: 486 (M + H)+ |
| 126 | Ph-benzyl with piperidinylmethyl, amide linked to quinolin-2(1H)-one at 7-position; HCl | NMR: δ 1.20-1.35 (1H, m), 1.52-1.66 (3H, m), 1.70-1.85 (2H, m), 2.53-2.67 (2H, m), 3.16-3.23 (2H, m), 4.38 (2H, d, J = 5.3Hz), 6.39 (1H, dd, J = 9.3, 2.0Hz), 7.35-7.66 (8H, m), 7.84 (1H, d = 9.3Hz), 8.06 (1H, dd, J = 8.3, 1.5Hz), 8.17 (1H, s), 8.68 (1H, s), 10.05 (1H, brs), 10.82 (1H, s), 11.78 (1H, s). FAB-MS: 438 (M + H)+ |
| 127 | Ph-benzyl with piperidinylmethyl, amide linked to 1,3-dimethylquinolin-2(1H)-one at 7-position; HCl | NMR: δ 1.20-1.37 (1H, m), 1.53-1.66 (3H, m), 1.70-1.85 (2H, m), 2.12 (3H, s), 2.55-2.70 (2H, m), 3.20-3.29 (2H, m), 3.63 (3H, s), 4.40 (2H, d, J = 5.4Hz), 7.36-7.58 (6H, m), 7.63 (1H, d, J = 8.8Hz), 7.74 (1H, s), 7.95 (1H, dd, J = 8.8, 1.4Hz), 8.04 (1H, dd, J = 7.8, 1.5Hz), 8.28 (1H, d, J = 1.0Hz), 8.85 (1H, s), 10.32 (1H, brs), 10.96 (1H, s). FAB-MS: 466 (M + H)+ |
| 128 | Ph-benzyl with piperidinylmethyl, amide linked to 3-methyl-3,4-dihydroquinolin-2(1H)-one at 7-position; HCl | NMR: δ 1.13 (3H, d, J = 6.9Hz), 1.20-1.34 (1H, m), 1.52-1.64 (3H, m), 1.72-1.89 (2H, m), 2.45-2.65 (4H, m), 2.91 (1H, dd, J = 15.7, 5.9Hz), 3.19 (2H, d, J = 11.7Hz), 4.37 (2H, d, J = 5.4Hz), 7.13 (1H, d, J = 8.3Hz), 7.32-7.58 (7H, m), 7.59 (1H, d, J = 1.9Hz), 8.00 (1H, dd, J = 8.3, 1.5Hz), 8.68 (1H, d, J = 1.5Hz), 10.15 (1H, s), 10.21 (1H, brs), 10.53 (1H, s). FAB-MS: 454 (M + H)+ |
| 129 | Ph-benzyl with piperidinylmethyl, amide linked to 1-methylquinolin-2(1H)-one at 7-position; HCl | NMR: δ 1.19-1.30 (1H, m), 1.53-1.66 (3H, m), 1.80-1.97 (2H, m), 2.55-2.69 (2H, m), 3.23-3.26 (2H, m), 3.61 (3H, s), 4.40 (2H, d, J = 4.9Hz), 6.52 (1H, d, J = 9.3Hz), 7.36-7.58 (6H, m), 7.72 (1H, d, J = 8.3Hz), 7.86 (1H, d, J = 9.3Hz), 7.97 (1H, dd, J = 8.3, 1.4Hz), 8.05 (1H, dd, J = 8.3, 1.4Hz), 8.32 (1H, d, J = 1.4Hz), 8.84 (1H, d, J = 1.4Hz), 10.25 (1H, brs), 11.01 (1H, s). FAB-MS: 452 (M + H)+ |

TABLE 27-continued

| Ex | Structure (salt) | DATA |
|---|---|---|
| 130 | 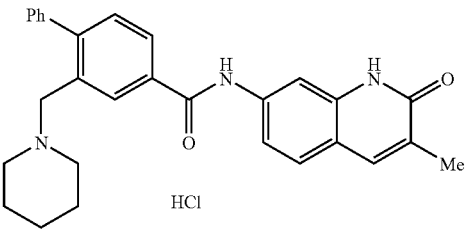 | NMR: δ 1.20-1.35 (1H, m), 1.50-1.65 (3H, m), 1.80-1.95 (2H, m), 2.08 (3H, s), 2.45-2.67 (2H, m), 3.23 (2H, d, J = 11.2Hz), 4.39 (2H, d, J = 5.4Hz), 6.52 (1H, d, J = 9.3Hz), 7.36-7.66 (8H, m), 8.03 (1H, dd, J = 1.4, 7.8Hz), 8.21 (1H, d, J = 1.5Hz), 8.80 (1H, d, J = 1.4Hz), 10.42 (1H, br s), 10.83 (1H, s), 11.78 (1H, s). FAB-MS: 452 (M + H)⁺ |

TABLE 28

| Ex | Structure (salt) | DATA |
|---|---|---|
| 131 | 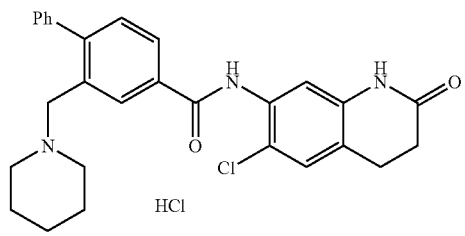 | NMR: δ 1.23-1.31 (1H, m), 1.52-1.78 (5H, m), 2.46-2.64 (4H, m), 2.89-2.94 (2H, m), 3.16-3.23 (2H, m), 4.37 (2H, d, J = 5.4Hz), 7.06 (1H, s), 7.38-7.43 (3H, m), 7.47-7.57 (4H, m), 8.08 (1H, dd, J = 7.9, 1.9Hz), 8.59 (1H, d, J = 1.9Hz), 9.90 (1H, brs), 10.23 (1H, s), 10.29 (1H, s). FAB-MS: 474 (M + H)⁺ |
| 132 | 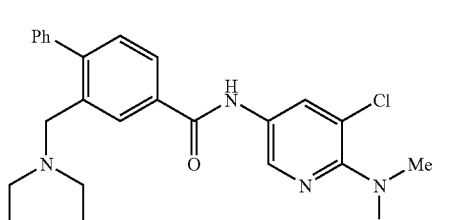 | NMR: δ 1.20-1.35 (1H, m), 1.52-1.64 (3H, m), 1.80-1.94 (2H, m), 2.56-2.68 (2H, m), 2.91 (6H, s), 3.16-3.26 (2H, m), 4.39 (2H, d, J = 5.3Hz), 4.74 (1H, brs), 7.36-7.42 (2H, m), 7.46-7.58 (4H, m), 8.02 (1H, dd, J = 8.3, 1.5Hz), 8.40 (1H, d, J = 2.0Hz), 8.77 (1H, d, J = 2.5Hz), 8.80-8.84 (1H, m), 10.22 (1H, brs), 10.91 (1H, s). FAB-MS: 449 (M + H)⁺ |
| 133 | 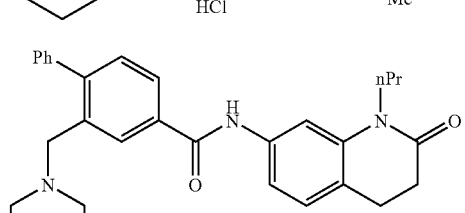 | NMR: δ 1.20-1.35 (1H, m), 1.50-1.65 (3H, m), 1.80-1.95 (2H, m), 2.08 (3H, s), 2.45-2.67 (2H, m), 3.23 (2H, d, J = 11.2Hz), 4.39 (2H, d, J = 5.4Hz), 6.52 (1H, d, J = 9.3Hz), 7.36-7.66 (8H, m), 8.03 (1H, dd, J = 1.4, 7.8Hz), 8.21 (1H, d, J = 1.5Hz), 8.80 (1H, d, J = 1.4Hz), 10.42 (1H, br s), 10.83 (1H, s), 11.78 (1H, s). FAB-MS: 452 (M + H)⁺ |
| 134 | 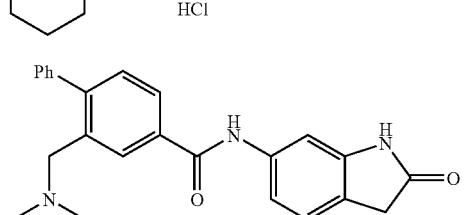 | NMR: δ 1.21-1.34 (1H, m), 1.53-1.64 (3H, m), 1.76-1.90 (2H, m), 2.54-2.66 (2H, m), 3.18-3.26 (2H, m), 3.62 (2H, s), 4.38 (2H, d, J = 5.2Hz), 7.38-7.43 (2H, m), 7.47-7.57 (5H, m), 7.90 (2H, d, J = 2.4Hz), 8.03 (1H, dd, J = 8.1, 1.7Hz), 8.72 (1H, d, J = 1.5Hz), 10.11 (1H, brs), 10.83 (1H, s), 10.93 (1H, s). FAB-MS: 494 (M + H)⁺ |
| 135 | 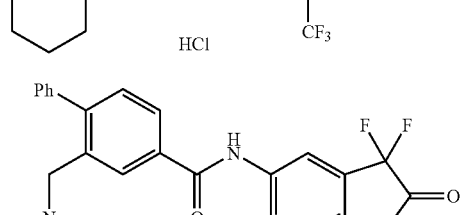 | NMR: δ 1.22-1.34 (1H, m), 1.52-1.65 (3H, m), 1.79-1.94 (2H, m), 2.56-2.68 (2H, m), 3.19 (3H, s), 3.18-3.26 (2H, m), 4.39 (2H, d, J = 4.9Hz), 7.28 (1H, d, J = 8.3Hz), 7.38-7.43 (2H, m), 7.47-7.57 (4H, m), 8.03 (1H, d, J = 7.8Hz), 8.18 (1H, d, J = 7.8Hz), 8.34 (1H, m), 8.79 (1H, m), 10.20 (1H, brs), 10.91 (1H, s). FAB-MS: 476 (M + H)⁺ |

TABLE 28-continued

| Ex | Structure (salt) | DATA |
|---|---|---|
| 136 | 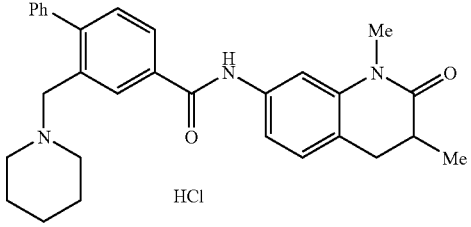 HCl | NMR: δ 0.92 (3H, t, J = 7.4Hz), 1.20-1.40 (1H, m), 1.54-1.75 (7H, m), 2.50-2.90 (6H, m), 3.10-3.25 (2H, m), 3.70-3.85 (2H, m), 4.38 (2H, d, J = 5.4Hz), 6.52 (1H, d, J = 9.3Hz), 7.21 (2H, d, J = 8.3Hz), 7.37-7.61 (5H, m), 7.77 (1H, s), 8.08 (1H, m), 8.58 (1H, s), 9.71 (1H, brs), 10.54 (1H, s). FAB-MS: 468 (M + H)$^+$ |
| 137 | 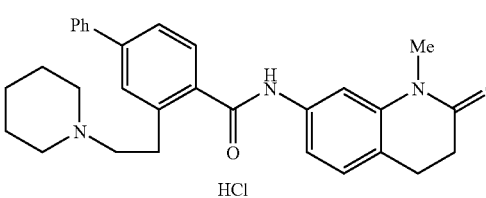 HCl | NMR: δ 1.34-1.47 (1H, m), 1.64-1.86 (5H, m), 2.52-2.58 (2H, m), 2.80-2.88 (2H, m), 2.88-3.00 (2H, m), 3.19-3.25 (2H, m), 3.24 (3H, s), 3.34-3.42 (2H, m), 3.44-3.51 (2H, m), 7.19 (1H, d, J = 8.3Hz), 7.41-7.47 (2H, m), 7.50-7.58 (3H, m), 7.66-7.78 (5H, m), 9.89 (1H, brs), 10.51 (1H, s). FAB-MS: 468 (M + H)$^+$ |

TABLE 29

| Ex | Structure (salt) | DATA |
|---|---|---|
| 138 | 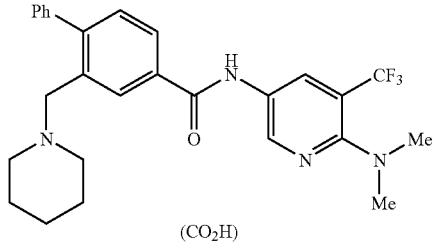 (CO$_2$H) | NMR: δ 1.30-1.44 (2H, brm), 1.48-1.60 (4H, brm), 2.54-2.70 (4H, brm), 2.90 (6H, s), 3.90-4.08 (2H, m), 7.40-7.55 (6H, m), 8.06 (1H, d, J = 8.3Hz), 8.31 (1H, brs), 8.46-8.49 (1H, m), 8.85 (1H, d, J = 1.9Hz), 10.62-10.68 (1H, brm). FAB-MS: 483 (M + H)$^+$ |
| 139 | 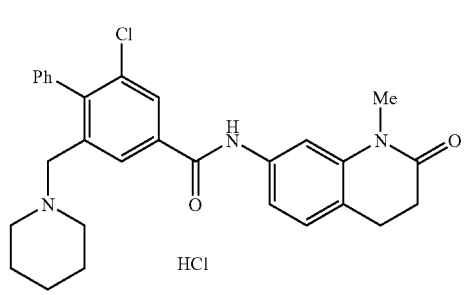 HCl | NMR: δ 1.22-1.35 (1H, m), 1.56-1.66 (3H, m), 1.76-1.90 (2H, m), 2.53-2.68 (4H, m), 2.81-2.89 (2H, m), 3.26 (3H, s), 3.26-3.37 (2H, m), 4.14 (2H, d, J = 5.4Hz), 7.22 (1H, d, J = 7.8Hz), 7.31-7.36 (2H, m), 7.49-7.59 (3H, m), 7.64 (1H, dd, J = 8.3, 1.9Hz), 7.74 (1H, d, J = 1.9Hz), 8.18 (1H, s), 8.72 (1H, d, J = 1.9Hz), 10.03 (1H, brs), 10.69 (1H, s). FAB-MS: 488 (M + H)$^+$ |
| 140 | 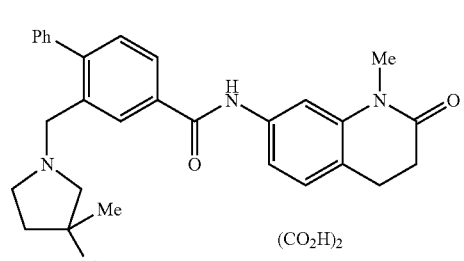 (CO$_2$H)$_2$ | NMR: δ 0.98 (6H, s), 1.58 (2H, t, J = 7.3Hz), 2.45-2.63 (4H, m), 2.80-3.02 (4H, m), 3.26 (3H, s), 4.07 (2H, brs), 7.20 (1H, d, J = 7.8Hz), 7.43-7.55 (7H, m), 7.60 (1H, s), 8.04 (1H, d, J = 7.8Hz), 8.24 (1H, s) 10.37 (1H, s). FAB-MS: 468 (M + H)$^+$ |

TABLE 29-continued

| Ex | Structure (salt) | DATA |
|---|---|---|
| 141 | [Structure: 4-Ph-3-(piperidinomethyl)benzamide coupled to 2-methyl-3-oxo-3,4-dihydro-2H-1,4-benzoxazin-6-yl, HCl salt] | NMR: δ 1.20-1.34 (1H, m), 1.42 (3H, d, J = 6.8Hz), 1.53-1.62 (3H, m), 1.71-1.86 (2H, m), 2.53-2.65 (2H, m), 3.14-3.24 (2H, m), 4.37 (2H, d, J = 5.4Hz), 4.63 (1H, q, J = 6.9Hz), 6.95 (1H, d, J = 8.3Hz), 7.34-7.42 (3H, m), 7.45-7.57 (4H, m), 7.68 (1H, d, J = 2.4Hz), 7.99-8.05 (1H, m), 8.65 (1H, s), 10.08 (1H, brs), 10.52 (1H, s,), 10.75 (1H, s). FAB-MS: 456 (M + H)+ |
| 142 | [Structure: 4-Ph-3-(piperidinomethyl)benzamide coupled to 2-methyl-3-oxo-3,4-dihydro-2H-1,4-benzoxazin-6-yl, HCl salt] | NMR: δ 1.20-1.34 (1H, m), 1.42 (3H, d, J = 6.8Hz), 1.53-1.62 (3H, m), 1.71-1.86 (2H, m), 2.53-2.65 (2H, m), 3.14-3.24 (2H, m), 4.37 (2H, d, J = 5.4Hz), 4.63 (1H, q, J = 6.9Hz), 6.95 (1H, d, J = 8.3Hz), 7.34-7.42 (3H, m), 7.45-7.57 (4H, m), 7.68 (1H, d, J = 2.4Hz), 7.99-8.05 (1H, m), 8.65 (1H, s), 10.08 (1H, brs), 10.52 (1H, s,), 10.75 (1H, s). FAB-MS: 456 (M + H)+ |
| 143 | [Structure: 4-Ph-3-(diethylaminomethyl)benzamide coupled to 4-CF3-2-oxoindolin-6-yl, HCl salt] | NMR: δ 0.97 (6H, t, J = 7.0Hz), 2.73-2.89 (2H, m), 2.94-3.10 (2H, m), 3.62 (2H, s), 4.35-4.45 (2H, m), 7.38-7.46 (2H, m), 7.47-7.59 (4H, m), 7.83-7.94 (2H, m), 7.99-8.07 (1H, m), 8.67 (1H, s), 10.15 (1H, brs), 10.82 (1H, s), 10.85-10.93 (1H, m). FAB-MS: 482 (M + H)+ |
| 144 | [Structure: 4-Ph-3-(morpholinomethyl)benzamide coupled to 1-methyl-2-oxo-1,2,3,4-tetrahydroquinolin-7-yl, HCl salt] | NMR: δ 2.53-2.58 (2H, m), 2.75-2.88 (4H, m), 3.19-3.27 (5H, m), 3.70-3.90 (4H, m), 4.40-4.50 (2H, m), 7.19-7.22 (1H, m), 7.38-7.42 (2H, m), 7.46-7.56 (4H, m), 7.62-7.66 (1H, m), 7.75 (1H, s), 8.02-8.07 (1H, m), 8.68 (1H, s), 10.57 (1H, s), 10.69 (1H, brs). FAB-MS: 456 (M + H)+ |
| 145 | [Structure: 4-Ph-3-[(bis(2-methoxyethyl)amino)methyl]benzamide coupled to 1-methyl-2-oxo-1,2,3,4-tetrahydroquinolin-7-yl, HCl salt] | NMR: δ 2.52-2.60 (2H, m), 2.80-2.88 (2H, s), 3.13 (3H, s), 3.13-3.22 (4H, m), 3.36 (6H, s), 3.56-3.65 (4H, m), 4.59 (2H, d, J = 4.9Hz), 7.20 (1H, d, J = 8.3Hz), 7.38-7.60 (6H, m) 7.66 (1H, dd, J = 8.3, 1.5Hz), 7.80 (1H, s), 8.06 (1H, d, J = 8.3Hz), 8.77 (1H, s), 10.46 (1H, brs), 10.60 (1H, s). FAB-MS: 502 (M + H)+ |

TABLE 30

| Ex | Structure (salt) | DATA |
|---|---|---|
| 146 | [Structure: 4-Ph-3-[(N-ethyl-N-(2-methoxyethyl)amino)methyl]benzamide coupled to 1-methyl-2-oxo-1,2,3,4-tetrahydroquinolin-7-yl, HCl salt] | NMR: δ 0.98 (3H, t, J = 7.3Hz), 2.57-2.60 (2H, m), 2.80-2.90 (2H, m), 2..80-3.40 (6H, m), 3.15 (3H, s), 3.26 (3H, s), 3.52-3.65 (2H, m), 4.40-4.60 (2H, m), 7.20 (1H, d, J = 8.3Hz), 7.37-7.60 (6H, m), 7.66 (1H, dd, J = 7.8, 1.5Hz), 7.82 (1H, d, J = 1.5Hz), 8.04 (1H, d, J = 7.8Hz), 8.76 (1H, s), 10.44 (1H, brs), 10.63 (1H, s). FAB-MS: 472 (M + H)+ |

TABLE 30-continued

| Ex | Structure (salt) | DATA |
|---|---|---|
| 147 | (3-methyl-pyrrolidinylmethyl-biphenyl-carboxamide with 1-methyl-3,4-dihydroquinolin-2(1H)-one); HCl | NMR: δ 0.88-1.00 (3H, m), 1.36-1.56 (1H, m), 1.90-2.05 (1H, m), 2.15-2.40 (2H, m), 2.52-2.75 (2H, m), 2.80-3.00 (3H, m), 3.25 (3H, s), 3.36-3.50 (2H, m), 4.44-4.52 (2H, m), 7.18-7.22 (1H, m), 7.38-7.43 (2H, m), 7.46-7.58 (4H, m), 7.64-7.70 (1H, m), 7.80 (1H, s), 8.00-8.04 (1H, m), 8.70-8.74 (1H, m), 10.56 (1H, s), 10.75-10.95 (1H, br). FAB-MS: 454 (M + H)+ |
| 148 | (3-methoxy-piperidinylmethyl-biphenyl-carboxamide with 1-methyl-3,4-dihydroquinolin-2(1H)-one); HCl | NMR: δ 1.10-1.26 (1H, m), 1.45-2.00 (5H, m), 2.54-2.57 (2H, m), 2.69-2.86 (3H, m), 3.06-3.79 (2H, m), 3.21 (3H, s), 3.25 (3H, s), 4.27-4.32, 4.61-4.54 (2H, m), 7.19-7.22 (1H, m), 7.35-7.75 (7H, m), 7.82 (1H, s), 7.99, 8.01 (1H, d, J = 8.3Hz), 8.62, 8.78 (1H, s), 9.50-10.65 (2H, m). FAB-MS: 484 (M + H)+ |
| 149 | (3-methyl-pyrrolidinylmethyl-biphenyl-carboxamide with 3,4-dihydroquinolin-2(1H)-one); HCl | NMR: δ 0.87-0.98 (3H, m), 1.35-1.54 (1H, m), 1.90-2.05 (1H, m), 2.10-2.47 (3H, m), 2.70-3.00 (5H, m), 3.34-3.50 (1H, m), 4.42-4.50 (2H, m), 7.12-7.16 (1H, m), 7.32-7.37 (1H, m), 7.38-7.43 (2H, m), 7.46-7.57 (4H, m), 7.60 (1H, s), 7.99-8.05 (1H, m), 8.61 (1H, brs), 10.17 (1H, s), 10.43 (1H, s), 10.74 (1H, brs). FAB-MS: 440 (M + H)+ |
| 150 | (piperidinylmethyl-biphenyl-carboxamide with 5-bromo-6-dimethylamino-pyridine); HCl | NMR: δ 1.20-1.34 (1H, m), 1.53-1.64 (3H, m), 1.71-1.86 (2H, m), 2.54-2.66 (2H, m), 2.87 (6H, s), 3.17-3.23 (2H, m), 4.38 (2H, d, J = 5.4Hz), 7.37-7.57 (6H, m), 8.05 (1H, dd, J = 7.8, 2.0Hz), 8.50 (1H, d, J = 2.4Hz), 8.69 (1H, d, J = 1.5Hz), 8.77 (1H, d, J = 2.4Hz), 9.91 (1H, brs), 10.79 (1H, s). FAB-MS: 493, 495 (M + H)+ |
| 151 | (2,5-dimethyl-pyrrolidinylmethyl-biphenyl-carboxamide with 1-methyl-3,4-dihydroquinolin-2(1H)-one); HCl | NMR: δ 0.79 (3H, d, J = 6.8Hz), 1.39 (3H, d, J = 6.4Hz), 1.46-1.56 (1H, m), 1.58-1.70 (1H, m), 1.96-2.12 (1H, m), 2.18-2.32 (1H, m), 2.53-2.58 (2H, m), 2.82-2.88 (2H, m), 3.26 (3H, s), 3.42-3.52 (1H, m), 3.64-3.74 (1H, br), 4.08-4.4.17 (1H, m), 4.66-4.77 (1H, m), 7.18-7.22 (1H, m), 7.38-7.46 (2H, m), 7.48-7.60 (4H, m), 7.66-7.72 (1H, m), 7.82-7.86 (1H, m), 8.05-8.10 (1H, m), 9.00 (1H, s), 10.26 (1H, brs), 10.58 (1H, s). FAB-MS: 468 (M + H)+ |
| 152 | (3-ethoxy-pyrrolidinylmethyl-biphenyl-carboxamide with 1-methyl-3,4-dihydroquinolin-2(1H)-one); HCl | NMR: δ 0.84-1.10 (3H, m), 1.78-2.06 (2H, m), 2.52-2.58 (2H, m), 2.77-2.98 (4H, m), 3.15-3.22 (2H, m), 3.25 (3H, s), 3.35-3.50 (2H, m), 4.07 (1H, br), 4.40-4.60 (2H, m), 7.18-7.22 (1H, m), 7.38-7.44 (2H, m), 7.46-7.58 (4H, m), 7.58-7.70 (1H, m), 7.74-7.82 (1H, m), 7.99-8.09 (1H, m), 8.65-8.75 (1H, m), 10.51 (1H, s), 11.12 (1H, s). 484 (M + H)+ |

TABLE 31

| Ex | Structure (salt) | DATA |
|---|---|---|
| 153 | 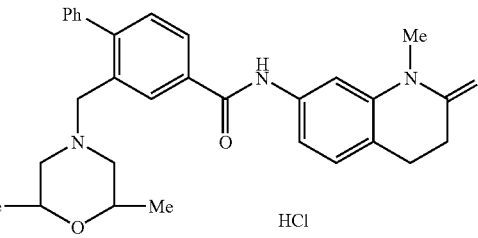 HCl | NMR: δ 1.02 (6H, d, J = 6.4Hz), 2.28-2.38 (2H, m), 2.52-2.58 (2H, m), 2.82-2.88 (2H, m), 3.18-3.26 (5H, m), 3.95-4.14 (2H, m), 4.37-4.52 (2H, m), 7.18-7.22 (1H, m), 7.38-7.44 (2H, m), 7.46-7.58 (4H, m), 7.60-7.70 (1H, m), 7.78 (1H, brs), 8.00-8.08 (1H, m), 8.72 (1H, br), 10.50-10.60 (1H, m), 10.98 (1H, br). FAB-MS: 484 (M + H)$^+$ |
| 154 | 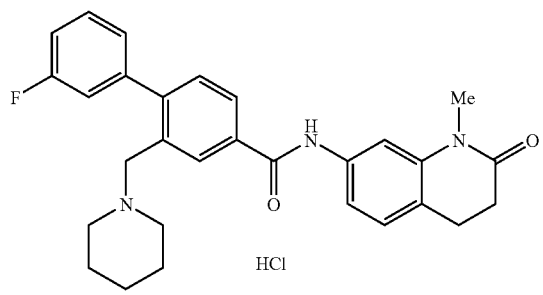 HCl | NMR: δ 1.23-1.35 (1H, m), 1.55-1.67 (3H, m), 1.67-1.78 (2H, m), 2.53-2.58 (2H, m), 2.60-2.71 (2H, m), 2.81-2.88 (2H, m), 3.19-3.27 (5H, m), 4.37 (2H, d, J = 5.4Hz), 7.19-7.26 (2H, m), 7.30-7.37 (2H, m), 7.50-7.63 (3H, m), 7.71 (1H, s), 8.03 (1H, d, J = 7.8Hz), 8.60 (1H, s), 9.74 (1H, brs), 10.58 (1H, s). FAB-MS: 472 (M + H)$^+$ |
| 155 | 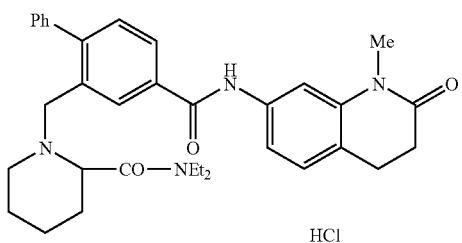 HCl | NMR: δ 1.05-1.17 (6H, m), 1.40-1.57 (2H, m), 1.60-1.76 (2H, m), 1.78-1.96 (2H, m), 2.36-2.44 (1H, m), 2.52-2.58 (2H, m), 2.82-2.88 (2H, m), 2.91-2.99 (1H, m), 3.26 (3H, s), 3.27-3.40 (3H, br), 3.46-3.54 (1H, m), 4.00-4.14 (1H, m), 4.32-4.40 (1H, m), 4.50-4.60 (1H, m), 7.18-7.24 (1H, m), 7.36-7.42 (2H, m), 7.44-7.60 (5H, m), 7.73 (1H, s), 8.06-8.12 (1H, m), 8.38 (1H, s), 9.67-9.80 (1H, m), 10.72 (1H, brs). FAB-MS: 553 (M + H)$^+$ |
| 156 | 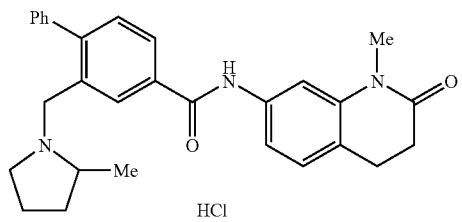 HCl | NMR: δ 1.33 (3H, d, J = 6.4Hz), 1.54-1.90 (3H, m), 2.00-2.10 (1H, m), 2.52-2.58 (2H, m), 2.60-2.72 (1H, m), 2.82-2.88 (2H, m), 3.26 (3H, s), 3.28-3.38 (2H, m), 4.12-4.24 (1H, m), 4.70-4.80 (1H, m), 7.18-7.24 (1H, m), 7.38-7.46 (2H, m), 7.46-7.60 (4H, m), 7.62-7.68 (1H, m), 7.76-7.84 (1H, m), 8.00-8.08 (1H, m), 8.64-8.72 (1H, m), 10.27 (1H, br), 10.59 (1H, s). FAB-MS: 454 (M + H)$^+$ |
| 157 | 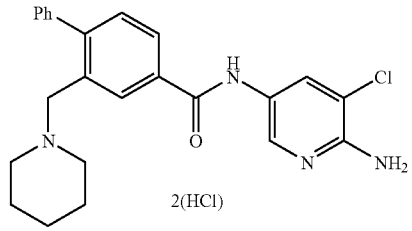 2(HCl) | NMR: δ 1.20-1.33 (1H, m), 1.50-1.63 (3H, m), 1.78-1.92 (2H, m), 2.58-2.68 (2H, m), 3.14-3.28 (2H, m), 4.38 (2H, d, J = 5.4Hz), 3.85-5.25 (3H, brm), 7.40 (2H, d, J = 6.9Hz), 7.44-7.56 (4H, m), 8.00 (1H, dd, J = 8.3, 1.5Hz), 8.47 (1H, d, J = 2.0Hz), 8.61 (1H, d, J = 2.0Hz), 8.78 (1H, s), 10.08 (1H, brs), 10.94 (1H, s). FAB-MS: 421 (M + H)$^+$ |
| 158 | 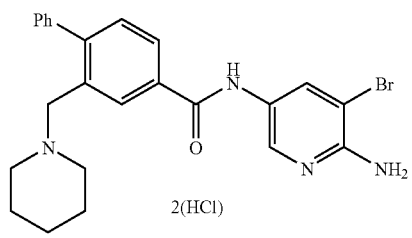 2(HCl) | 1.24-1.34 (1H, m), 1.50-1.65 (3H, m), 1.75-1.93 (2H, m), 2.56-2.69 (2H, m), 3.14-3.26 (2H, m), 4.03 (3H, br s), 4.38 (2H, d, J = 5.4Hz), 7.34-7.56 (6H, m), 8.02 (1H, dd, J = 7.8, 2.0, 1.5Hz), 8.60 (1H, d, J = 2.0Hz), 8.64 (1H, d, J = 2.0Hz), 8.77 (1H, d, J = 1.5Hz), 10.06 (1H, brs), 10.92 (1H, s). FAB-MS: 467 (M + H)$^+$ |

TABLE 31-continued

| Ex | Structure (salt) | DATA |
| --- | --- | --- |
| 159 | 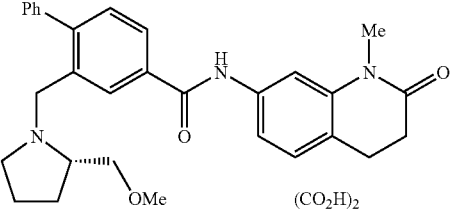 (CO₂H)₂ | NMR: δ 1.45-1.60 (1H, m), 1.60-1.75 (2H, m), 1.80-2.00 (1H, m), 2.35-2.48 (1H, br), 2.52-2.58 (2H, m), 2.82-2.88 (2H, m), 2.90-3.02 (1H, br), 3.05-3.22 (5H, m), 3.26 (3H, s), 3.30-3.40 (1H, br), 3.75-4.00 (1H, br), 4.30-4.50 (1H, m), 7.18-7.22 (1H, m), 7.38-7.58 (7H, m) , 7.64 (1H, s), 7.95-8.10 (1H, m), 8.25 (1H, s), 10.39 (1H, s). FAB-MS: 484 (M +H)⁺ |

TABLE 32

| Ex | Structure (salt) | DATA |
| --- | --- | --- |
| 160 | 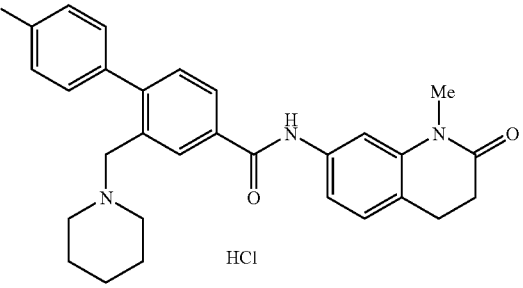 HCl | NMR: δ 1.20-1.34 (1H, m), 1.54-1.65 (3H, m), 1.74-1.87 (2H, m), 2.52-2.68 (4H, m), 2.80-2.87 (2H, m), 3.16-3.27 (5H, m), 4.34 (2H, d, J = 5.3Hz), 7.20 (1H, d, J = 8.3Hz), 7.33-7.40 (2H, m), 7.42-7.50 (3H, m), 7.64 (1H, dd, J = 8.8, 2.0Hz), 7.96 (1H, d, J = 1.9Hz), 8.04 (1H, dd, J = 8.8, 2.0Hz), 8.69 (1H, s), 9.98 (1H, s), 10.62 (1H, s). FAB-MS: 472 (M + H)⁺ |
| 161 | 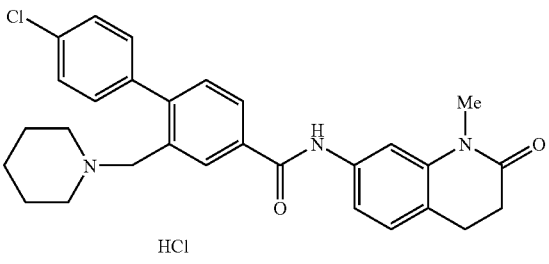 HCl | NMR: δ 1.20-1.37 (1H, m), 1.54-1.68 (3H, m), 1.76-1.96 (2H, m), 2.60-2.72 (4H, m), 2.78-2.90 (2H, m), 3.16-3.36 (5H, m), 4.27-4.42 (2H, m), 7.20 (1H, d, J = 8.3Hz), 7.38-7.52 (3H, m), 7.52-7.62 (2H, m), 7.64-7.71 (1H, m), 7.76-7.84 (1H, m), 7.95-8.07 (1H, m), 8.77 (1H, s), 10.17 (1H, brs), 10.63-10.73 (1H, m). FAB-MS: 488 (M)⁺ |
| 162 | 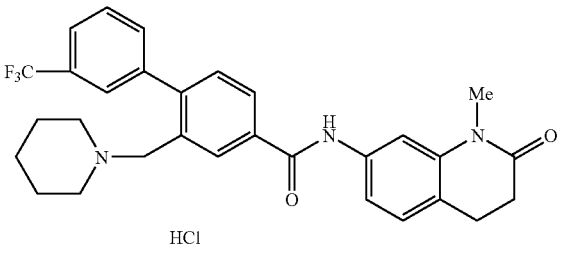 HCl | NMR: δ 1.18-1.37 (1H, m), 1.50-1.69 (3H, m), 1.79-1.97 (2H, m), 2.52-2.72 (4H, m), 2.79-2.90 (2H, m), 3.18-3.28 (5H, m), 4.26-4.42 (2H, m), 7.20 (1H, d, J = 8.3Hz), 7.53 (1H, d, J = 7.8Hz), 7.64-7.90 (6H, m), 8.03-8.10 (1H, m), 8.78-8.87 (1H, m), 10.24 (1H, brs), 10.66-10.75 (1H, m). FAB-MS: 522 (M + H)⁺ |
| 163 | 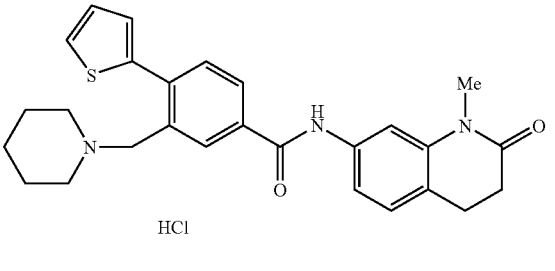 HCl | NMR: δ 1.25-1.42 (1H, m), 1.54-1.72 (3H, m), 1.78-1.97 (2H, m), 2.52-2.59 (2H, m), 2.60-2.90 (4H, m), 3.17-3.49 (5H, m), 4.46-4.60 (2H, m), 7.13-7.35 (3H, m), 7.56-7.69 (2H, m), 7.73-7.85 (2H, m), 7.95-8.07 (1H, m), 8.77 (1H, brs), 10.26 (1H, brs), 10.61-10.71 (1H, m). FAB-MS: 460 (M + H)⁺ |

TABLE 32-continued

| 164 | [structure: 3'-chloro-biphenyl with piperidinylmethyl, benzamide linked to 1-methyl-3,4-dihydroquinolin-2(1H)-one; HCl] | NMR: δ 1.20-1.38 (1H, m), 1.52-1.69 (3H, m), 1.78-1.97 (2H, m), 2.52-2.74 (4H, m), 2.78-2.89 (2H, m), 3.17-3.28 (5H, m), 4.28-4.43 (2H, m), 7.20 (1H, d, J = 7.9Hz), 7.32-7.40 (1H, m), 7.44-7.60 (4H, m), 7.64-7.72 (1H, m), 7.76-7.83 (1H, m), 7.97-8.06 (1H, m), 8.80 (1H, s), 10.20 (1H, brs), 10.64-10.73 (1H, m). FAB-MS: 488 (M)+ |
|---|---|---|
| 165 | [structure: piperidine-carbonyl-piperidinylmethyl-biphenyl benzamide linked to 1-methyl-3,4-dihydroquinolin-2(1H)-one; HCl] | NMR: δ 1.90-2.06 (10H, m), 2.50-3.30 (7H, m), 3.32-3.40 (m, 6H), 3.26 (3H, s), 4.10-4.24, 4.38-4.54 (2H, m), 7.16-7.24 (1H, m), 7.34-7.68 (7H, m), 7.79 (1H, s), 8.02, 8.06 (1H, d, J = 8.3Hz), 8.55, 8.72 (1H, s), 9.15, 10.28 (1H, brs), 10.40, 10.60 (1H, s). FAB-MS: 565 (M)+ |
| 166 | [structure: biphenyl with morpholinylmethyl, benzamide linked to 2-methyl-benzoxazin-3(4H)-one; HCl] | NMR: δ 1.42 (3H, d, J = 6.8Hz), 2.73-2.85 (2H, m), 3.17-3.26 (2H, m), 3.73-3.88 (4H, m), 4.41-4.49 (2H, m), 4.63 (1H, d, J = 6.8Hz), 6.96 (1H, d, J = 8.3Hz), 7.33-7.42 (3H, m), 7.45-7.57 (4H, m), 7.68 (1H, s), 8.02 (1H, d, J = 7.8Hz), 8.65 (1H, s), 10.49 (1H, s), 10.75 (1H, s), 10.71-10.86 (1H, br). FAB-MS: 458 (M + H)+ |
| 167 | [structure: biphenyl with 4-cyanopiperidinylmethyl, benzamide linked to 1-methyl-3,4-dihydroquinolin-2(1H)-one] | NMR: δ 1.79-2.25 (4H, m), 2.50-2.90-(9H, m), 3.26 (3H, s), 4.38, 4.51 (2H, s), 7.21 (1H, d, J = 8.3Hz), 7.44-7.70 (7H, m), 8.05 (1H, d, J = 7.8Hz), 7.74 (1H, s), 8.63 (1H, s), 10.22 (1H, brs), 10.56 (1H, s). FAB-MS: 479 (M)+ |

TABLE 33

| Ex | Structure (salt) | DATA |
|---|---|---|
| 168 | [structure: biphenyl with piperidinylmethyl, benzamide linked to 3-fluoro-6-(dimethylamino)pyridine; (CO2H)2] | NMR: δ 1.36-1.60 (6H, m), 2.56-2.73 (4H, m), 2.98 (3H, s), 2.99 (3H, s), 3.75-6.30 (4H, brm), 7.41-7.54 (6H, m), 7.97 (1H, dd, J = 15.1, 2.0Hz), 8.04 (1H, ddd, J = 7.8, 2.0, 1.5Hz), 8.29 (1H, s), 8.39 (1H, m), 10.49 (1H, s). FAB-MS: 433 (M + H)+ |

TABLE 33-continued

| Ex | Structure (salt) | DATA |
|---|---|---|
| 169 | 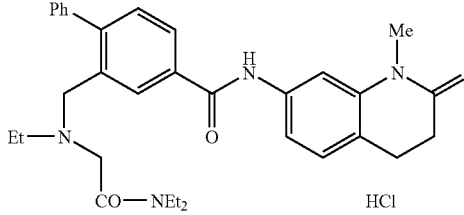 HCl | NMR: δ 0.77 (3H, t, J = 7.4Hz), 1.03-1.10 (6H, m), 2.50-2.60 (2H, m), 2.67-2.73 (1H, m), 2.83-2.87 (2H, m), 2.87-3.00 (1H, m), 3.18-3.41 (4H, m), 3.26 (3H, s), 4.35, 4.44 (2H, m), 4.46-4.55 (2H, m), 7.22 (1H, d, J = 8.3Hz), 7.40-7.59 (7H, m), 7.66 (1H, s), 8.11 (1H, d, J = 8.3Hz), 8.52 (1H, s), 9.55 (1H, brs), 10.50 (1H, s). FAB-MS: 527 (M + H)+ |
| 170 | 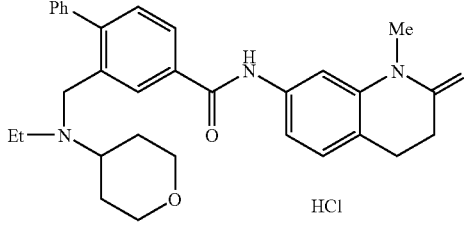 HCl | NMR: δ 1.03 (3H, t, J = 7.3Hz), 1.36 (1H, d, J = 11.7Hz), 1.64-1.80 (2H, m), 2.06 (1H, d, J = 11.7Hz), 2.50-2.57 (2H, m), 2.83-2.96 (4H, m), 3.13 (1H, t, J = 11.7Hz), 3.24-3.34 (2H, m), 3.25 (3H, s), 3.76 (1H, d, J = 7.9Hz), 3.87 (1H, d, J = 7.9Hz), 4.34 (1H, dd, J = 13.6, 6.3Hz), 4.65 (1H, dd, J = 13.6, 4.9Hz), 7.20 (1H, d, J = 7.9Hz), 7.42-7.58 (6H, m), 7.66 (1H, dd, J = 8.3, 2.0Hz), 7.83 (1H, d, J = 7.9Hz), 8.03 (1H, dd, J = 8.3, 1.5Hz), 8.71 (1H, dd, J = 1.5Hz), 10.23 (1H, brs), 10.69 (1H, s). FAB-MS: 498 (M + H)+ |
| 171 | 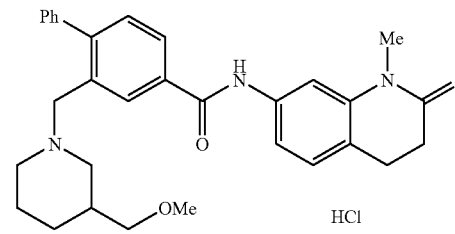 HCl | NMR: δ 1.02-1.07 (1H, m), 1.57-1.69 (2H, m), 1.85-2.00 (1H, m), 2.28-2.44 (2H, m), 2.50-2.58 (2H, m), 2.83-2.86 (2H, m), 3.02-3.06 (1H, m), 3.17-3.47 (5H, m), 3.19 (3H, s), 3.25 (3H, s), 4.35-4.47 (2H, m), 7.20 (1H, d, J = 8.3Hz), 7.34-7.58 (6H, m), 7.66 (1H, dd, J = 8.3, 1.9Hz), 7.80 (1H, d, J = 2.0Hz), 8.02 (1H, dd, J = 8.3, 2.0Hz), 8.78 (1H, dd, J = 2.0Hz), 10.40 (1H, brs), 10.66 (1H, s). FAB-MS: 498 (M + H)+ |
| 172 | 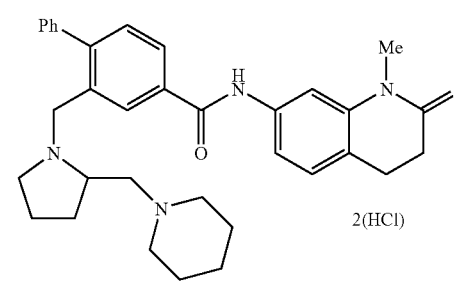 2(HCl) | NMR: δ 1.28-1.45 (1H, br), 1.55-2.00 (9H, m), 2.28-2.42 (1H, br), 2.52-2.58 (2H, m), 2.80-2.88 (2H, m), 2.90-3.00 (2H, br), 3.13-3.23 (2H, m), 3.25 (3H, s), 3.48-3.58 (2H, m), 3.94-4.12 (2H, m), 4.14-4.32 (2H, m), 5.06-5.18 (1H, m), 7.18-7.22 (1H, m), 7.34-7.42 (2H, m), 7.48-7.58 (4H, m), 7.65-7.73 (1H, s), 7.80 (1H, s), 7.98-8.05 (1H, s), 8.79 (1H, s), 10.50 (1H, s), 10.92 (1H, s), 11.11 (1H, s). FAB-MS: 537 (M + H)+ |
| 173 | 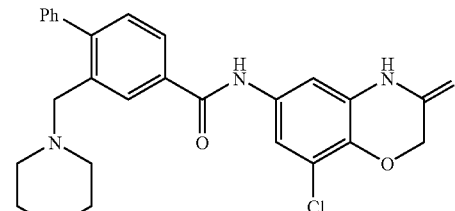 (CO2H)2 | NMR: δ 1.30-1.44 (2H, m), 1.46-1.56 (4H, m), 2.32-2.69 (2H, m), 3.10-4.05 (4H, m), 4.65 (2H, s), 7.12 (1H, s), 7.20 (1H, s), 7.40-7.54 (6H, m), 8.00-8.09 (1H, m), 8.23 (1H, s), 10.05 (1H, s), 10.90 (1H, s). FAB-MS: 476 (M + H)+ |
| 174 | 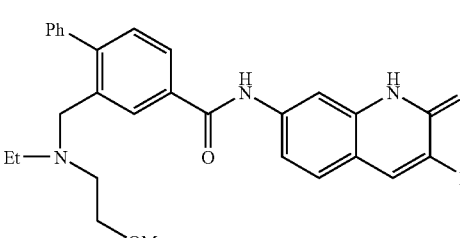 HCl | NMR: δ 0.97 (3H, t, J = 7.3Hz), 2.08 (3H, s), 2.75-3.50 (4H, m), 3.16 (3H, s), 3.57 (2H, s), 4.44-4.55 (2H, d, m), 7.42 (2H, d, J = 6.8Hz), 7.46-7.62 (6H, m), 7.71 (1H, s), 8.07 (1H, d, J = 7.8Hz), 8.13 (1H, s), 8.65 (1H, s), 10.15 (1H, brs), 10.48 (1H, s), 11.78 (1H, s). FAB-MS: 470 (M + H)+ |

TABLE 34

| Ex | Structure (salt) | DATA |
|---|---|---|
| 175 | 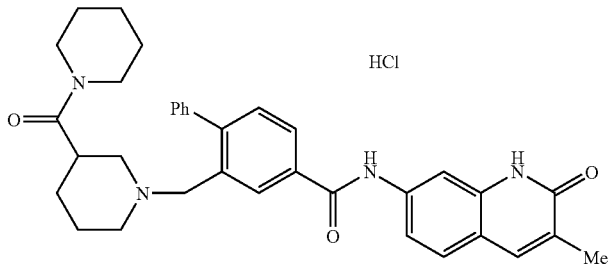 | NMR: δ 1.39-1.74 (10H, m), 2.08 (3H, s), 2.49-3.37 (9H, m), 4.15-4.21, 4.45-4.49 (2H, m), 7.30-7.62 (8H, m), 7.71 (1H, s), 7.90-8.16 (2H, m), 8.54, 8.67 (1H, s), 9.13, 10.23 (1H, brs), 10.56, 10.73 (1H, s), 11.78, 11.80 (1H, s). FAB-MS: 563 (M + H)$^+$ |
| 176 | 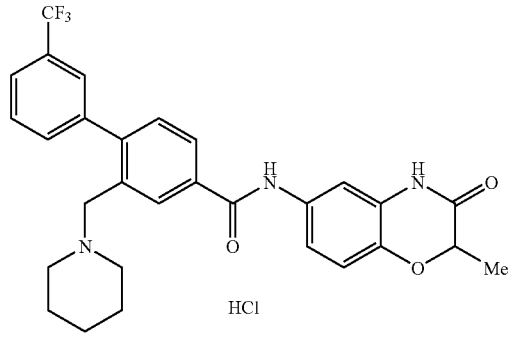 | NMR: δ 1.20-1.33 (1H, m), 1.43 (3H, d, J = 6.8Hz), 1.55-1.64 (3H, m), 1.70-1.84 (2H, m), 2.58-2.70 (2H, m), 3.16-3.26 (2H, m), 4.34 (2H, d, J = 4.9Hz), 4.64 (1H, q, J = 6.8Hz), 6.96 (1H, d, J = 8.8Hz), 7.36 (1H, dd, J = 8.8, 2.5Hz), 7.35 (1H, d, J = 8.3Hz), 7.64-7.68 (1H, m), 7.70-7.80 (3H, m), 7.87 (1H, d, J = 7.4Hz), 8.06 (1H, d, J = 7.8Hz), 8.65 (1H, brs), 9.96 (1H, brs), 10.54 (1H, s), 10.76 (1H, s). FAB-MS: 524 (M + H)$^+$ |
| 177 | 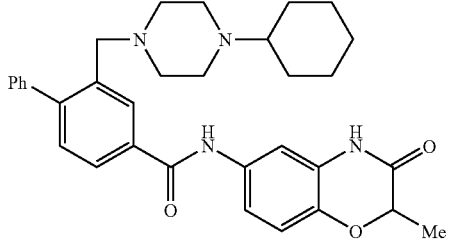 | NMR: δ 1.00-1.12 (1H, m), 1.16-1.29 (2H, m), 1.29-1.42 (2H, m), 1.42 (3H, d, J = 6.8Hz), 1.55-1.64 (1H, m), 1.74-1.84 (2H, m), 2.01-2.10 (2H, m), 2.32-2.42 (2H, m), 2.76-2.86 (2H, m), 2.86-2.99 (2H, m), 3.03-3.13 (1H, m), 2.80-3.37 (2H, m), 3.52 (2H, s), 4.63 (1H, q, J = 6.8Hz), 6.95 (1H, d, J = 8.8Hz), 7.28 (1H, dd, J = 8.8, 2.4Hz), 7.38-7.55 (7H, m), 7.94 (1H, d, J = 7.8Hz), 8.05 (1H, s), 9.45 (1H, brs), 10.28 (1H, s), 10.75 (1H, s). FAB-MS: 539 (M + H)$^+$ |
| 178 | 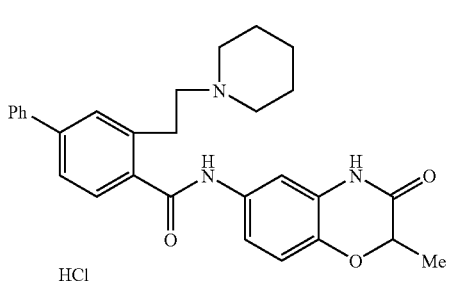 | NMR: δ 1.33-1.46 (1H, m), 1.42 (3H, d, J = 6.9Hz), 1.60-1.90 (5H, m), 2.88-3.00 (2H, m), 3.15-3.25 (2H, m), 3.32-3.53 (4H, m), 4.62 (1H, q, J = 6.8Hz), 6.95 (1H, d, J = 8.3Hz), 7.23 (1H, dd, J = 8.8, 2.5Hz), 7.41-7.46 (1H, m), 7.48-7.56 (3H, m), 7.62-7.77 (5H, m), 9.66 (1H, brs), 10.45 (1H, s), 10.74 (1H, s). FAB-MS: 470 (M + H)$^+$ |
| 179 | 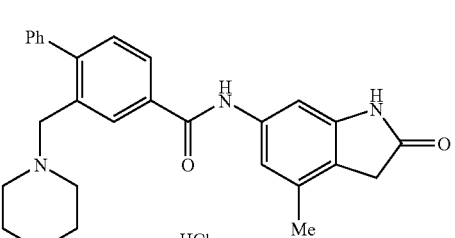 | NMR: δ 1.18-1.37 (1H, m), 1.50-1.68 (3H, m), 1.72-1.92 (2H, m), 2.18 (3H, s), 2.53-2.70 (2H, m), 3.14-3.26 (2H, m), 3.37 (2H, s), 4.31-4.44 (2H, m), 7.26-7.60 (8H, m), 8.00 (1H, d, J = 7.9Hz), 8.68 (1H, s), 10.22 (1H, brs), 10.40 (1H, s), 10.44-10.54 (1H, m). FAB-MS: 440 (M + H)$^+$ |

TABLE 34-continued

| Ex | Structure (salt) | DATA |
|---|---|---|
| 180 | 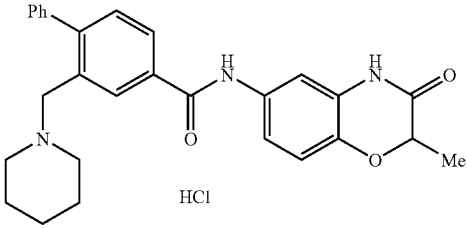 HCl | NMR: δ 1.20-1.37 (1H, m), 1.45 (3H, d, J = 6.3Hz), 1.54-1.68 (3H, m), 1.70-1.88 (2H, m), 2.58-2.74 (2H, m), 3.14-3.26 (2H, m), 4.26-4.40 (2H, m), 4.63 (1H, q, J = 6.7Hz), 6.96 (1H, d, J = 8.8Hz), 7.32-7.40 (2H, m), 7.46-7.60 (4H, m), 7.67 (1H, s), 8.03 (1H, d, J = 7.8Hz), 8.64 (1H, s), 9.99 (1H, brs), 10.50-10.58 (1H, m), 10.75 (1H, s). FAB-MS: 490 (M + H)+ |
| 181 | 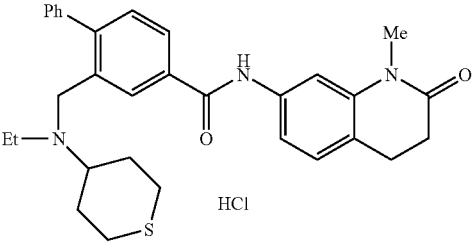 HCl | NMR: δ 1.22 (3H, t, J = 7.3Hz), 1.50-1.70 (2H, m), 1.81 (1H, d, J = 11.8Hz), 2.36 (1H, d, J = 12.2Hz), 2.50-2.70 (5H, m), 2.85 (2H, t, J = 6.8Hz), 2.88-3.12 (3H, m), 3.25 (3H, s), 3.29-3.40 (2H, m), 4.37 (1H, dd, J = 14.1, 5.4Hz), 4.57 (1H, dd, J = 14.1Hz, 5.4Hz), 7.20 (1H, d, J = 8.3Hz), 7.45-7.60 (6H, m), 7.64 (1H, dd, J = 8.3, 1.5), 7.79 (1H, d, J = 1.4Hz), 8.07 (1H, dd, J = 8.3, 1.5Hz), 8.67 (1H, s), 9.88 (brs), 10.65 () 1H, s). FAB-MS 514 (M + H)+ |

TABLE 35

| Ex | Structure (salt) | DATA |
|---|---|---|
| 182 | 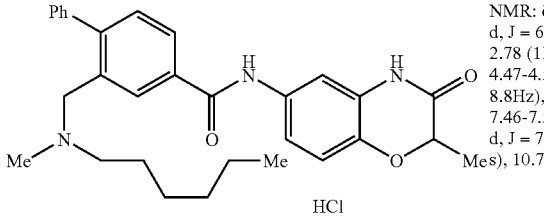 HCl | NMR: δ 0.84 (3H, t, J = 7.1Hz), 1.08-1.38 (8H, m), 1.42 (3H, d, J = 6.8Hz), 1.45-1.57 (1H, m), 2.46-2.54 (2H, m), 2.65-2.78 (1H, m), 2.79-2.97 (1H, m), 4.20-4.37 (1H, m), 4.47-4.57 (1H, m), 4.63 (1H, q, J = 6.9Hz), 6.96 (1H, d, J = 8.8Hz), 7.34 (1H, dd, J = 8.8, 2.5Hz), 7.41 (2H, d, J = 6.4Hz), 7.46-7.57 (4H, m), 7.65 (1H, d, J = 1.9Hz), 8.04 (1H, d, J = 7.8Hz), 8.53 (1H, s), 10.06 (1H, brs), 10.45 (1H, s), 10.75 (1H, s). FAB-MS: 486 (M + H)+ |
| 183 | 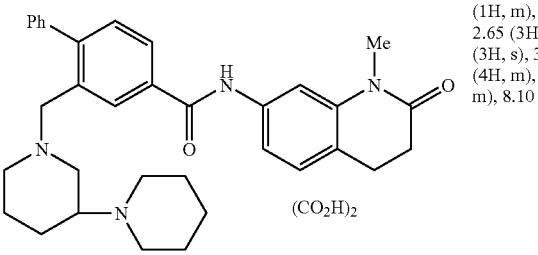 (CO2H)2 | NMR: δ 1.35-1.55 (4H, m), 1.65-1.78 (5H, m), 1.82-1.92 (1H, m), 1.93-2.02 (1H, br), 2.07-2.17 (1H, m), 2.52-2.65 (3H, m), 2.80-2.87 (2H, m), 2.92-3.22 (6H, m), 3.26 (3H, s), 3.48-3.58 (2H, m), 7.17-7.22 (1H, m), 7.36-7.45 (4H, m), 7.45-7.54 (3H, m), 7.62 (1H, s), 7.92-7.98 (1H, m), 8.10 (1H, s), 10.41 (1H, s). FAB-MS: 537 (M + H)+ |
| 184 | 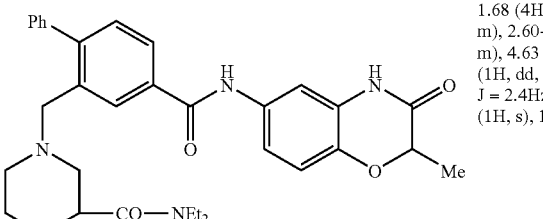 (CO2H)2 | NMR: δ 0.95 (3H, t, J = 7.1Hz), 1.05 (3H, t, J = 7.1Hz), 1.28-1.68 (4H, m), 1.42 (3H, d, J = 6.8Hz), 1.90-2.23 (1H, m), 2.60-2.78 (1H, m), 2.80-2.91 (1H, m), 3.07-4.00 (8H, m), 4.63 (1H, q, J = 6.9Hz), 6.95 (1H, d, J = 8.3Hz), 7.26 (1H, dd, J = 8.8, 2.4Hz), 7.37-7.52 (6H, m), 7.53 (1H, d, J = 2.4Hz), 7.92-8.00 (1H, m), 8.08-8.20 (1H, m), 10.27 (1H, s), 10.74 (1H, s). FAB-MS: 555 (M + H)+ |

TABLE 35-continued

| Ex | Structure (salt) | DATA |
|---|---|---|
| 185 | (structure) HCl | NMR: δ 1.42 (3H, d, J = 6.8Hz), 2.74-2.87 (2H, m), 3.28-3.40 (4H, m), 4.17-4.28 (2H, m), 4.44-4.57 (2H, m), 4.63 (1H, q, J = 6.9Hz), 6.66-6.73 (1H, m), 6.83-6.88 (1H, m), 6.96 (1H, d, J = 8.8Hz), 7.32-7.61 (8H, m), 7.67 (1H, s), 8.01-8.07 (1H, m), 8.08-8.12 (1H, s), 8.64 (1H, s), 10.50 (1H, s), 10.59 (1H, s), 10.75 (1H, s). FAB-MS: 534 (M + H)+ |
| 186 | (structure) HCl | NMR: δ 0.88-1.94 (16H, m), 2.52-2.88 (4H, m), 3.12-3.70 (5H, m), 4.50 (2H, d, J = 4.4Hz), 7.21 (1H, d, J = 8.3Hz), 7.42-7.66 (7H, m), 7.81 (1H, s), 8.03 (1H, d, J = 7.8Hz), 8.54 (1H, s), 9.19 (1H, brs), 10.82 (1H, s). FAB-MS: 510 (M + H)+ |
| 187 | (structure) HCl | NMR: δ 0.85 (12H, t, J = 6.8Hz), 1.89-2.00 (2H, m), 2.53-2.58 (2H, m), 2.67-2.72 (4H, m), 2.82-2.87 (2H, m), 3.26 (3H, s), 4.53 (2H, d, J = 4.9Hz), 7.21 (1H, d, J = 8.3Hz), 7.42-7.63 (7H, m), 7.54 (1H, d, J = 1.9Hz), 7.88-7.94 (1H, m), 8.70 (1H, d, J = 1.4Hz), 9.31 (1H, brs), 10.64 (1H, s). FAB-MS: 498 (M + H)+ |
| 188 | (structure) 2(HCl) | NMR: δ 1.76-1.88 (1H, m), 1.95-2.13 (2H, m), 2.17-2.32 (1H, m), 2.71-2.90 (2H, m), 3.16-3.28 (1H, m), 3.30-3.42 (1H, m), 4.29-4.56 (3H, m), 5.95 (2H, d, J = 7.3Hz), 6.36 (1H, dd, J = 8.8, 2.4Hz), 6.64 (1H, dd, J = 6.3, 2.0Hz), 6.79 (1H, dd, J = 8.3, 4.9Hz), 7.38-7.45 (2H, m), 7.47-7.58 (4H, m), 8.02-8.08 (1H, m), 8.09-8.18 (2H, m), 8.78-8.92 (2H, m), 9.42 (1H, s), 10.75 (1H, brs), 10.92 (1H, d, J = 2.9Hz). FAB-MS: 564 (M + H)+ |

TABLE 36

| Ex | Structure (salt) | DATA |
|---|---|---|
| 189 | (structure) HCl | NMR: δ 0.85 (3H, d, J = 6.6Hz), 1.22 (3H, d, J = 6.6Hz), 2.03 (3H, s), 3.08-3.20 (1H, m), 3.27-3.40 (2H, m) 4.32-4.47 (2H, m), 4.48-4.60 (2H, m), 7.43-7.59 (6H, m), 8.04-8.12 (2H, m), 8.16 (1H, d, J = 8.3Hz), 8.77-8.83 (2H, m), 9.41 (1H, s), 10.20 (1H, s), 10.91 (1H, s). FAB-MS: 488 (M + H)+ |
| 190 | (structure) 3(HCl) | NMR: δ 0.97 (3H, t, J = 7.1Hz), 2.66-3.14 (2H, m), 4.48 (2H, s), 4.62 (2H, s), 7.37-7.43 (2H, m), 7.46-7.58 (4H, m), 8.04 (1H, dd, J = 7.8, 1.5Hz), 8.09-8.20 (2H, m), 8.38 (2H, s), 8.76-8.85 (2H, m), 8.97 (2H, d, J = 5.9Hz), 9.43 (1H, s), 10.87 (1H, s), 11.47 (1H, brs). FAB-MS: 479 (M + H)+ |

TABLE 36-continued

| Ex | Structure (salt) | DATA |
|---|---|---|
| 191 | (Structure with Ph, cyclohexyl-N-CH2CH2-NHTs, benzamide linked to benzothiazole; 2(HCl)) | NMR: δ 0.88-1.03 (2H, m), 1.04-1.22 (2H, m), 1.23-1.36 (2H, m), 1.44-1.48 (2H, m), 1.62-1.71 (1H, m), 1.78-1.95 (2H, m), 2.01-2.10 (1H, m), 2.35 (3H, s), 2.66-2.98 (5H, m), 4.34-4.42 (1H, m), 4.49-4.57 (1H, m), 7.38 (2H, d, J = 8.3Hz), 7.42-7.47 (2H, m), 7.47-7.58 (4H, m), 7.60-7.68 (3H, m), 8.04-8.17 (3H, m), 8.75 (1H, s), 8.81 (1H, s), 9.41 (1H, s), 10.09 (1H, brs), 10.96 (1H, s). FAB-MS: 653 (M + H)+ |
| 192 | (Structure with Ph, iPr-N-CH2CH2OH, benzamide linked to benzothiazole) | NMR: δ 0.82-0.92 (6H, m), 2.50 (2H, t, J = 5.2Hz), 2.82-2.92 (1H, m), 3.40 (2H, t, J = 5.2Hz), 3.61 (0.2H, s), 3.66 (1.8H, s), 4.08-4.16 (1H, m), 7.25-7.35 (3H, m), 7.36-7.48 (3H, m), 7.82-7.88 (1H, m), 7.89-7.96 (2H, m), 8.20-8.25 (1H, m), 8.47 (1H, s), 8.68 (1H, brs), 9.00 (1H, s). FAB-MS: 446 (M + H)+ |
| 193 | (Structure with Ph, tBu-N-CH2CH2OMe, benzamide linked to 2-methyl-benzoxazinone; (CO2H)2) | NMR: δ 0.99 (9H, s), 1.42 (3H, d, J = 6.9Hz), 2.51-2.69 (2H, m), 3.00 (2H, s), 3.03 (3H, s), 6.94 (1H, d, J = 8.8Hz), 7.26 (1H, dd, J = 8.3, 2.4Hz), 7.29-7.39 (3H, m), 7.40-7.53 (3H, m), 7.57 (1H, d, J = 2.4Hz), 7.90 (1H, brs), 8.28 (1H, s), 10.24 (1H, s), 10.72. FAB-MS: 502 (M + H)+. |
| 194 | (Structure with Ph, 2,6-dimethyl-4-ethylpiperazine-CH2, benzamide linked to 2-methyl-benzoxazinone; 2(HCl)) | NMR: δ 1.12-1.15 (3H, m), 1.22 (6H, d, J = 5.8Hz), 1.42 (3H, d, J = 6.9Hz), 2.85-3.30 (4H, m), 3.40-4.00 (4H, m), 4.63 (1H, q, J = 6.6Hz), 6.95 (1H, d, J = 8.8Hz), 7.30 (1H, d, J = 8.8Hz), 7.40-7.54 (6H, m), 7.60 (1H, s), 7.96 (1H, d, J = 8.3Hz), 8.26 (1H, brs), 10.31 (1H, s), 10.75 (1H, s). FAB-MS: 513 (M + H)+. |
| 195 | (Structure with Ph, iPr-N-CH2CH2-piperidine, benzamide linked to 2-methyl-benzoxazinone; 2(HCl)) | NMR: δ 0.67-0.85 (6H, m), 1.30-1.55 (3.5H, m), 1.57-2.08 (6.5H, m), 2.60-2.77 (2H, m), 2.82-3.14 (3H, m), 3.33-3.65 (5H, m), 4.42-4.53 (0.5H, m), 4.58-4.68 (1.5H, m), 6.95 (1H, d, J = 8.3Hz), 7.25-7.65 (7.3H, m), 7.65-7.75 (0.7H, m), 7.87-8.20 (1.3H, m), 8.75 (0.7H, s), 10.00 (0.3H, br s), 10.26-10.50 (1.2H, m), 10.75 (1H, s), 10.93 (0.5H, s). FAB-MS: 555 (M + H)+. |
| 196 | (Structure with Ph, iPr-N-CH2CH2CH2OH, benzamide linked to 2-methyl-benzoxazinone; (CO2H)2) | NMR: δ 0.77 (6H, d, J = 6.3Hz), 1.42 (3H, d, J = 6.9Hz), 1.43-1.51 (2H, m), 1.60-1.70 (1H, m), 2.00-2.17 (2H, m), 2.31-2.50 (2H, m), 3.36 (2H, t, J = 6.3Hz), 3.00-4.10 (3H, m), 4.63 (1H, q, J = 6.8Hz), 6.93 (1H, d, J = 8.8Hz), 7.24 (1H, dd, J = 8.8, 2.4Hz), 7.32-7.50 (6H, m), 7.58 (1H, d, J = 2.5Hz), 7.90 (1H, d, J = 8.3Hz), 8.19 (1H, s), 10.26 (1H, s), 10.71 (1H, s). FAB-MS: 502 (M + H)+. |

TABLE 37

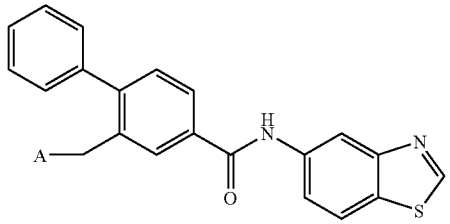

| Ex | A— | DATA |
|---|---|---|
| 197 | (3-chlorophenyl, MeO2C-pyrrolidine-N-Me) | H: 2.63<br>FP: 582 |
| 198 | (norbornyl CO2Et, NHMe) | H: 1.93<br>FP: 458 |
| 199 | (N-methylpiperazinyl-CH2CH2-CO2Et) | H: 2.28<br>FP: 529 |
| 200 | (EtO-C(O)-CH(Me)-NH-) | H: 2.18<br>FP: 460 |
| 201 | (3-CF3-N-methylpiperidine) | H: 2.28<br>FP: 496 |
| 202 | (2-(pyridin-3-yl)-N-methylpiperidine) | H: 2.02<br>FP: 505 |
| 203 | (1,1'-dimethyl-2,2'-bipiperidine) | H: 2.26<br>FP: 525 |

TABLE 37-continued

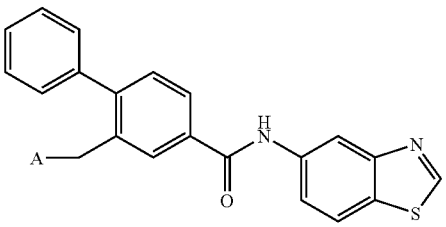

| Ex | A— | DATA |
|---|---|---|
| 204 | (2-hydroxyethyl-tetramethyl-N-methylpiperidine) | H: 2.16<br>FP: 528 |
| 205 | (2-(N-methyl-N-(2-hydroxyethyl)amino)pyridine) | H: 1.92<br>FP: 481 |
| 206 | (tBu-N(Me)-CH2CH2OH) | H: 1.94<br>FP: 460 |
| 207 | (HOCH2-C(Me)-N(Me)-Bu) | H: 2.15<br>FP: 474 |
| 208 | (iPr-CH2-N(Me)-CH2-CH(OH)-Me) | H: 2.07<br>FP: 474 |
| 209 | (2-(2-hydroxyethyl)-N-methylaniline) | H: 2.90<br>FP: 480 |
| 210 | (N-benzyl-N'-methyl-diazaspiro compound) | H: 2.06<br>FP: 587 |

TABLE 37-continued

| Ex | A— | DATA |
|---|---|---|
| 211 | (1-methyl-piperazinyl-benzothiazole) | H: 2.60<br>FP: 562 |
| 212 | (4-methylpiperazinylmethyl-2-chlorophenyl) | H: 2.52<br>FP: 553 |
| 213 | (ethyl ester, methylamino indane) | H: 2.60<br>FP: 548 |
| 214 | (EtO2C, NHMe, indolyl) | H: 2.58<br>FP: 575 |
| 215 | (CO2Me, N-methyl tetrahydroisoquinoline) | H: 2.86<br>FP: 534 |
| 216 | (2-pyridyl-N-methylpiperidine) | H: 2.15<br>FP: 505 |

TABLE 37-continued

| Ex | A— | DATA |
|---|---|---|
| 217 | (CO2Et, N-methylpiperidine) | H: 2.15<br>FP: 514 |
| 218 | (N-methylpiperidinyl, HO2C, Boc-pyrrolidine) | H: 2.61<br>FP: 641 |
| 219 | (Me-N-Me, N-methylpiperidinyl-phenyl) | H: 2.32<br>FP: 547 |
| 220 | (N-methyl tetrahydrothienopyridine) | H: 2.14<br>FP: 482 |

TABLE 38

| 221 | (tetrahydrofuran, N-methylpiperidine) | H: 2.26<br>FP: 498 |
| 222 | (CF3, N-methylpyrrolidine) | H: 3.23<br>FP: 482 |

TABLE 38-continued
| | | |
|---|---|---|
| 223 | 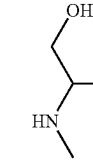 | H: 2.26<br>FP: 460 |
| 224 | 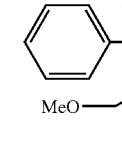 | H: 2.39<br>FP: 524 |
| 225 | 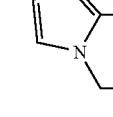 | H: 2.44<br>FP: 493 |
| 226 | 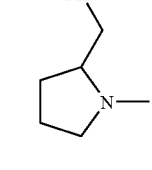 | H: 2.38<br>FP: 504 |
| 227 | 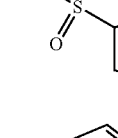 | H: 2.25<br>FP: 554 |
| 228 | 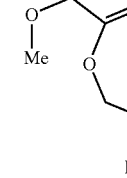 | H: 2.27<br>FP: 536 |
| 229 | 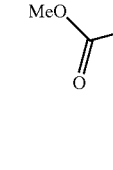 | H: 2.97<br>FP: 502 |
| 230 | 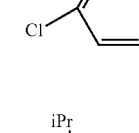 | H: 2.72<br>FP: 570 |
| 231 | 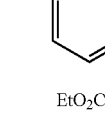 | H: 2.88<br>FP: 578 |
| 232 | 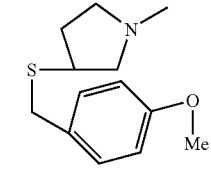 | H: 2.55<br>FP: 566 |
TABLE 39
| No | Structure |
|---|---|
| 1 | 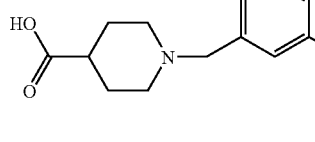 |
| 2 | 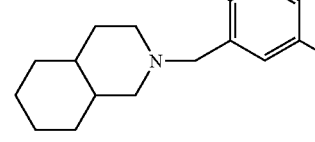 |
| 3 | 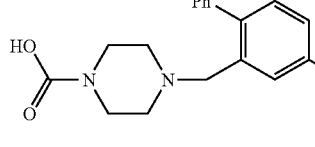 |
| 4 | 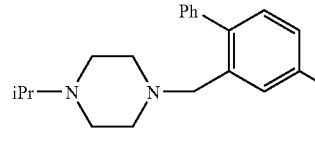 |
| 5 | 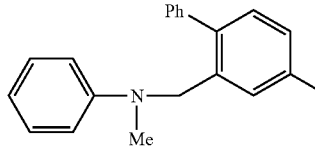 |
| 6 | 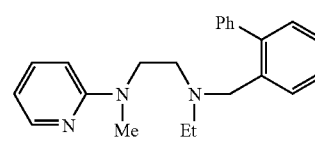 |
| 7 | 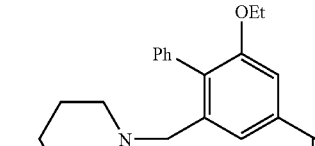 |

TABLE 39-continued
| No | Structure |
|---|---|
| 8 | 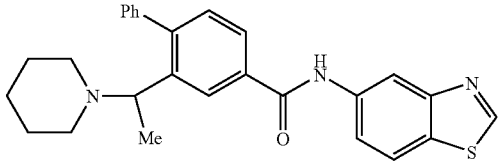 |
| 9 | 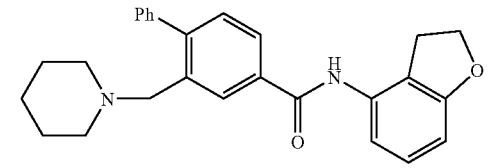 |
| 10 | 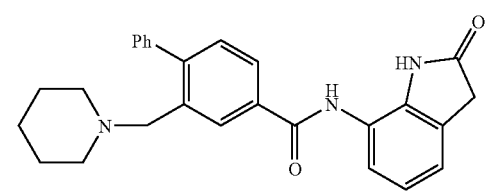 |
| 11 | 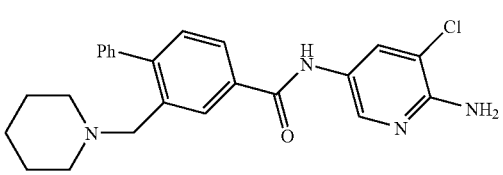 |
| 12 | 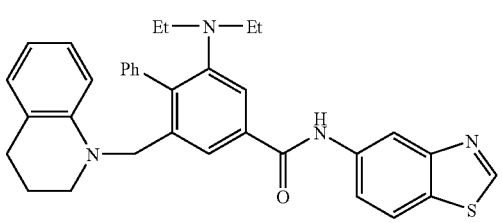 |
| 13 | 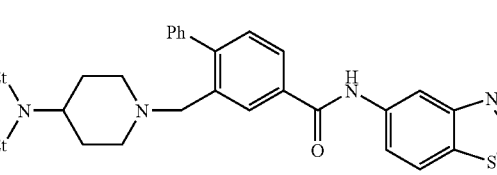 |
| 14 | 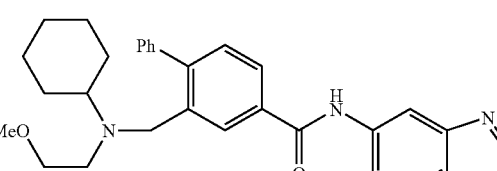 |
| 15 | 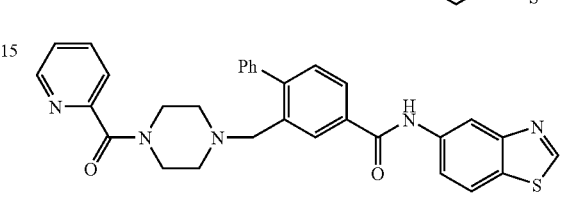 |
TABLE 39-continued
| No | Structure |
|---|---|
| 16 | 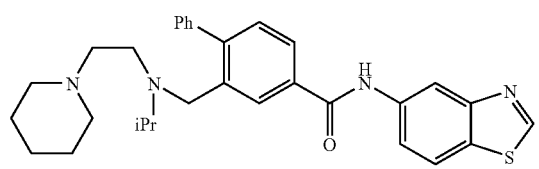 |
| 17 | 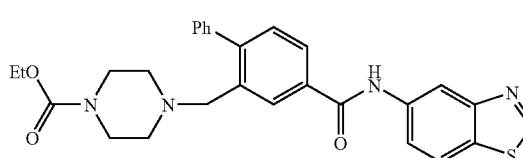 |
| 18 | 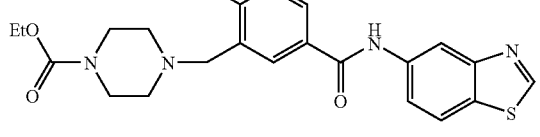 |
| 19 | 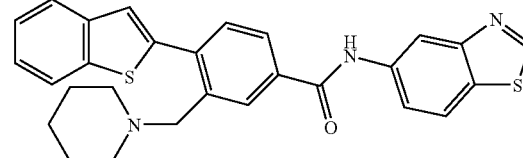 |
| 20 | 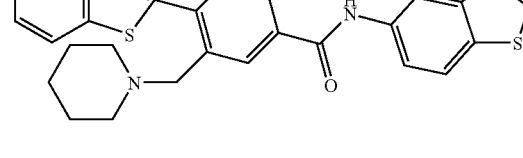 |
| 21 | 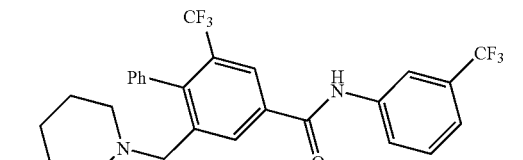 |
| 22 | 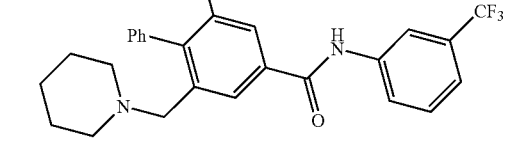 |

TABLE 40

| No | Structure |
|---|---|
| 23 | 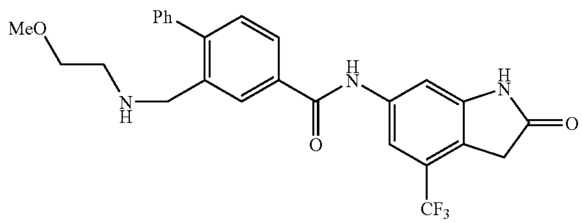 |
| 24 | 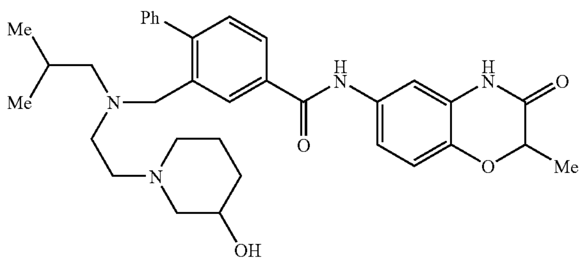 |
| 25 | 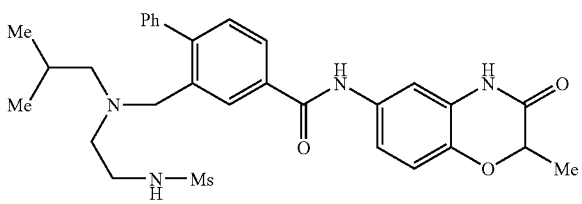 |
| 26 | 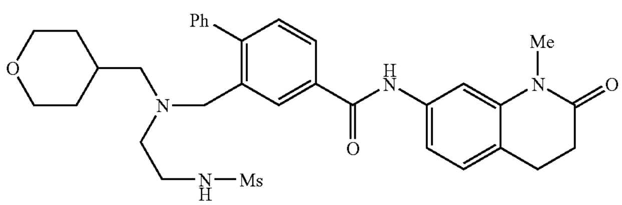 |
| 27 | 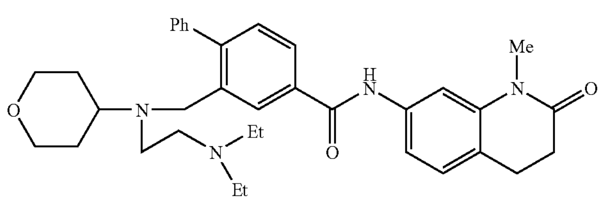 |
| 28 | 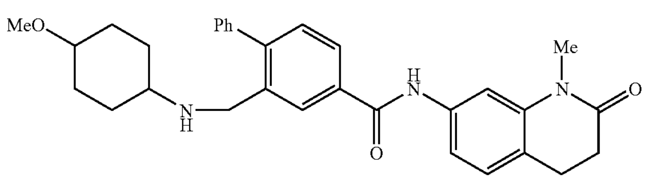 |
| 29 | 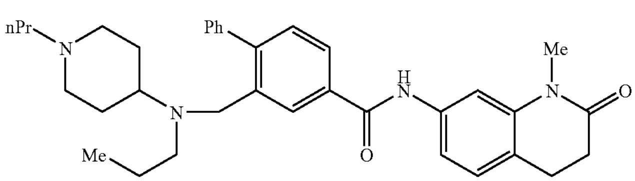 |

TABLE 40-continued

| No | Structure |
|---|---|
| 30 | 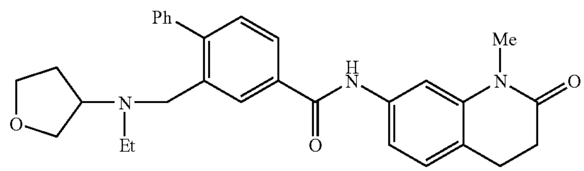 |
| 31 | 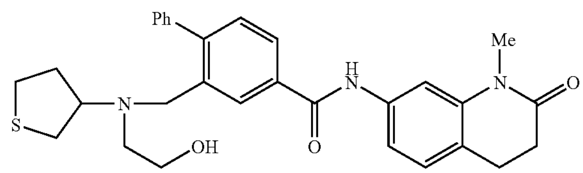 |
| 32 | 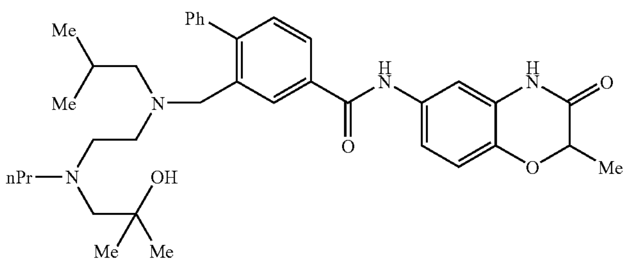 |
| 33 | 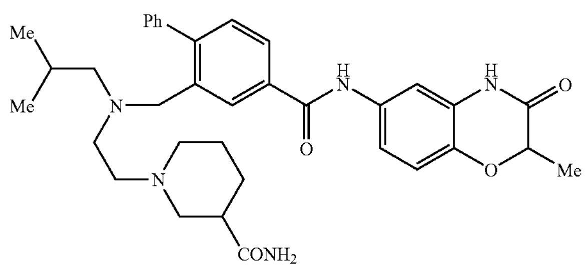 |
| 34 | 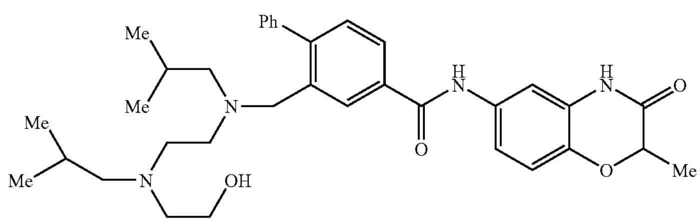 |
| 35 | 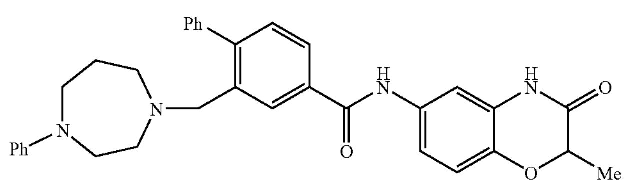 |
| 36 | 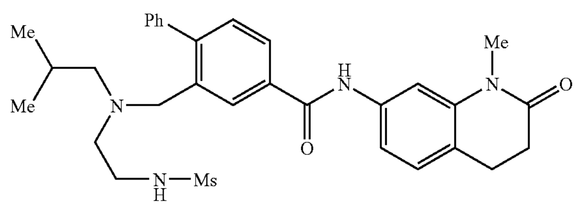 |

TABLE 40-continued
| No | Structure |
|---|---|
| 37 | 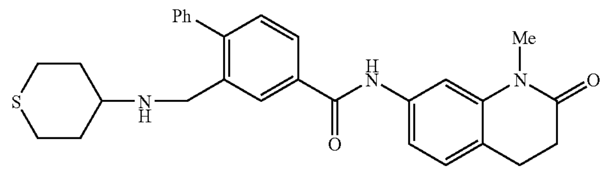 |
| 38 | 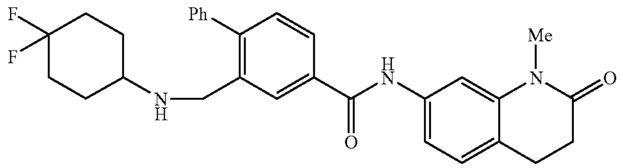 |
| 39 | 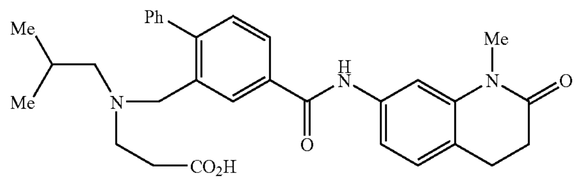 |
| 40 | 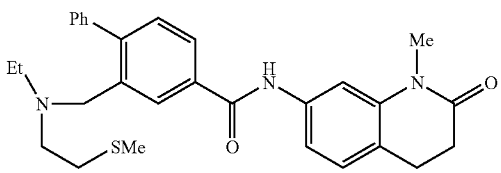 |
| 41 | 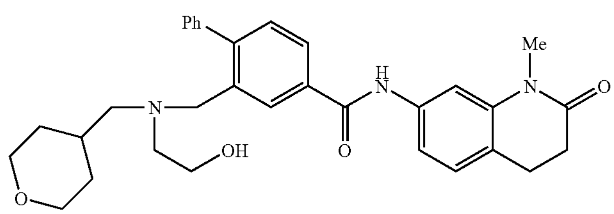 |
| 42 | 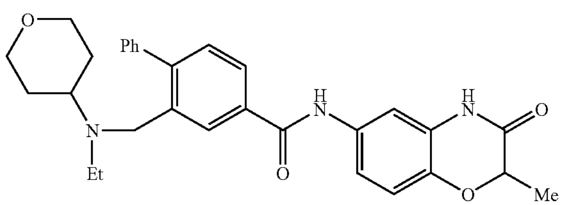 |
The invention claimed is:
1. A benzamide compound or salt thereof, represented by formula (I):
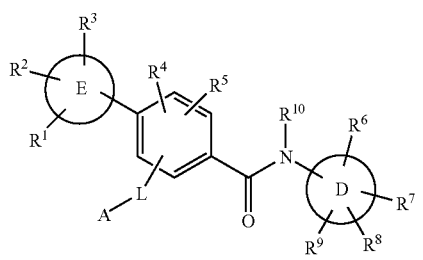
wherein
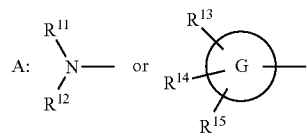
L: a lower alkylene;
D ring: a 3,4-dihydro-2H-1,4-benzoxazine ring;
E ring: a monocyclic or bicyclic hydrocarbon ring, or a 5- to 12-membered monocyclic or bicyclic heteroaromatic ring containing 1 to 4 atoms selected from the group consisting of N, S, and O;

G ring: a 4- to 12-membered monocyclic or bicyclic heterocycle containing 1 to 4 atoms selected from the group consisting of N, S, and O;

$R^1$ to $R^9$: the same or different, a hydrogen atom, a halogen atom, a lower alkyl, a halogen-substituted lower alkyl, —OH, —SH, —O-lower alkyl, —O-lower alkyl-NH-lower alkyl, —O-lower alkyl-N(lower alkyl)$_2$, =O, —NH$_2$, —NH-lower alkyl, —N(lower alkyl)$_2$, —S-lower alkyl, —SO-lower alkyl, —SO$_2$-lower alkyl, —CN, —COOH, —C(=O)—O-lower alkyl, —C(=O)—NH$_2$, —C(=O)—NH-lower alkyl, —C(=O)—N(lower alkyl)$_2$, —NH—C(=O)—O-lower alkyl, —NH—SO$_2$-lower alkyl, —SO$_2$—NH$_2$, —SO$_2$—NH-lower alkyl, —C(=O)-lower alkyl, —NO$_2$ or a 5- to 8-membered saturated or partially unsaturated monocyclic heterocycle which contains one N atom and may further contain one heteroatom selected from the group consisting of N, S, and O;

$R^{10}$: a hydrogen atom or a lower alkyl;

$R^{11}$ to $R^{15}$: the same or different, a hydrogen atom, a halogen atom, a lower alkyl, a halogen-substituted lower alkyl, —OH, —O-lower alkyl, —S-lower alkyl, —SO-lower alkyl, —SO$_2$-lower alkyl, =O, —C(=O)H, —C(=O)-lower alkyl, —COOH, —CN, —NH$_2$, —NH-lower alkyl, —N(lower alkyl)$_2$, —C(=O)—NH$_2$, —C(=O)—NH-lower alkyl, —C(=O)—N(lower alkyl)$_2$, —C(=O)-aryl, —C(=O)—NH-aryl, —NH—C(=O)-lower alkyl, —NH—C(=O)-aryl, —NH—SO$_2$-lower alkyl, —N(lower alkyl)-SO$_2$-lower alkyl, -lower alkylene-NH—SO$_2$-lower alkyl, -lower alkylene-NH—SO$_2$-aryl, —C(=O)—O-lower alkyl, -lower alkylene-OH, -lower alkylene-C(=O)—NH-lower alkyl, -lower alkylene-C(=O)—N(lower alkyl)$_2$, -lower alkylene-C(=O)—NH$_2$, -lower alkylene-C(=O)—OH, -lower alkylene-O-lower alkyl, -lower alkylene-S-lower alkyl, -lower alkylene-O—C(=O)-lower alkyl, -lower alkylene-NH-lower alkyl, -lower alkylene-N(lower alkyl)$_2$, -lower alkylene-aryl, a cycloalkyl, an aryl -(4- to 12-membered monocyclic or bicyclic heterocycle containing 1 to 4 atoms selected from the group consisting of N, S, and O), —O-(4- to 12-membered monocyclic or bicyclic heterocycle containing 1 to 4 atoms selected from the group consisting of N, S, and O), -lower alkylene-(4- to 12-membered monocyclic or bicyclic heterocycle containing 1 to 4 atoms selected from the group consisting of N, S, and O), —C(=O)-(4- to 12-membered monocyclic or bicyclic heterocycle containing 1 to 4 atoms selected from the group consisting of N, S, and O), -lower alkylene-N(lower alkyl)-(4- to 12-membered monocyclic or bicyclic heterocycle containing 1 to 4 atoms selected from the group consisting of N, S, and O), or —C(=O)—NH-(4- to 12-membered monocyclic or bicyclic heterocycle containing 1 to 4 atoms selected from the group consisting of N, S, and O); and the above monocyclic or bicyclic heterocycle may be substituted by halogen atom(s), lower alkyl(s), —O-lower alkyl, or —OH.

2. The compound according to claim 1 or salt thereof, wherein the E ring is a benzene ring or a thiophene ring.

3. The compound according to claim 2 or salt thereof, wherein the A group is:

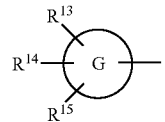

and wherein the G ring and $R^{13}$ to $R^{15}$ have the same meanings as in formula (I).

4. The compound according to claim 3 or salt thereof, wherein the G ring is a 5- to 8-membered saturated or partially unsaturated monocyclic heterocycle which contains one N atom and may further contain one heteroatom selected from the group consisting of N, S, and O and the ring nitrogen atom is bonded to L.

5. The compound according to claim 3 or salt thereof, wherein the G ring is a ring selected from the group consisting of morpholine, piperidine, or pyrrolidine and the ring nitrogen atom of the ring group is bonded to L.

6. The compound according to claim 3 or a salt thereof, wherein the E ring is benzene.

7. The compound according to claim 3 or a salt thereof, wherein the D ring, together with the groups represented by $R^6$ to $R^9$ to be bonded thereto, form a group represented by formula (II):

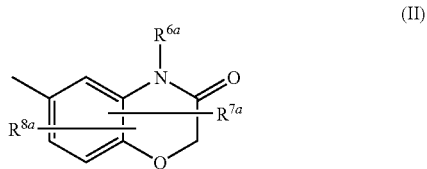

wherein $R^{6a}$: a hydrogen atom, a lower alkyl, or a halogen-substituted lower alkyl, and $R^{7a}$ and $R^{8b}$: the same or different, a hydrogen atom, a halogen atom, a lower alkyl, or a halogen-substituted lower alkyl.

8. The compound according to claim 2 or salt thereof, wherein the group represented by A is:

and wherein $R^{11a}$ and $R^{12a}$: the same or different, a hydrogen atom, a lower alkyl, a halogen-substituted lower alkyl, —O-lower alkyl, —SO$_2$-lower alkyl, —C(=O)H, —C(=O)-lower alkyl, —CN, —NH$_2$, —NH-lower alkyl, —N(lower alkyl)$_2$, —C(=O)—NH$_2$, —C(=O)—NH-lower alkyl, —C(=O)—N(lower alkyl)$_2$, —C(=O)-aryl, —C(=O)—NH-aryl, —NH—C(=O)-lower alkyl, —NH—C(=O)-aryl, —NH—SO$_2$-lower alkyl, —N(lower alkyl)—SO$_2$-lower alkyl, -lower alkylene-NH—SO$_2$-lower alkyl, -lower alkylene-NH—SO$_2$-aryl, —C(=O)—O-lower alkyl, -lower alkylene-OH, -lower alkylene-C(=O)—NH-lower alkyl, -lower alkylene-C(=O)—N(lower alkyl)$_2$, -lower alkylene-C(=O)—NH$_2$, -lower alkylene-C(=O)—OH, -lower alkylene-O-lower alkyl,

- -lower alkylene-S-lower alkyl, -lower alkylene-O—C(=O)-lower alkyl, -lower alkylene-NH-lower alkyl, -lower alkylene-N(lower alkyl)$_2$, -lower alkylene-aryl, a cycloalkyl, an aryl,
- -(4- to 12-membered monocyclic or bicyclic heterocycle containing 1 to 4 atoms selected from the group consisting of N, S, and O),
- —O-(4- to 12-membered monocyclic or bicyclic heterocycle containing 1 to 4 atoms selected from the group consisting of N, S, and O),
- -lower alkylene-(4- to 12-membered monocyclic or bicyclic heterocycle containing 1 to 4 atoms selected from the group consisting of N, S, and O),
- —C(=O)-(4- to 12-membered monocyclic or bicyclic heterocycle containing 1 to 4 atoms selected from the group consisting of N, S, and O),
- -lower alkylene-N(lower alkyl)-(4- to 12-membered monocyclic or bicyclic heterocycle containing 1 to 4 atoms selected from the group consisting of N, S, and O), or
- —C(=O)—NH-(4- to 12-membered monocyclic or bicyclic heterocycle containing 1 to 4 atoms selected from the group consisting of N, S, and O), and the above monocyclic or bicyclic heterocycle may be substituted by a halogen atom, a lower alkyl, —O-lower alkyl, or —OH.

9. The compound according to claim 8 or salt thereof, wherein the D ring, together with the groups represented by $R^6$ to $R^9$ to be bonded thereto, form a group represented by formula (II):

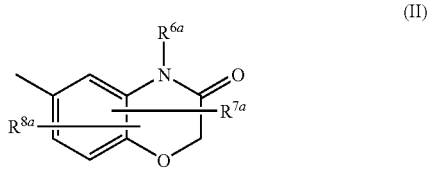

(II)

wherein
$R^{6a}$ and $R^{6b}$: the same or different, a hydrogen atom, a lower alkyl, or a halogen-substituted lower alkyl, and
$R^{7a}$, $R^{8a}$, $R^{7b}$, and $R^{8b}$: the same or different, a hydrogen atom, a halogen atom, a lower alkyl, or a halogen-substituted lower alkyl.

10. The compound according to claim 8 or a salt thereof, wherein $R^{11a}$ is a lower alkyl and $R^{12a}$ is a group selected from the group consisting of -lower alkylene-O-lower alkyl, -lower alkylene-S-lower alkyl, -lower alkylene-NH-lower alkyl, -lower alkylene-N(lower alkyl)$_2$, -lower alkylene-OH, -lower alkylene-C(=O)—NH-lower alkyl, -lower alkylene-C(=O)—N(lower alkyl)$_2$, -lower alkylene-aryl, a cycloalkyl, an aryl, -(monocyclic or bicyclic heterocycle), and -lower alkylene-(monocyclic or bicyclic heterocycle).

11. The compound according to claim 1 or a salt thereof, wherein the D ring is 3,4-dihydro-2H-1,4-benzoxazine and at least two of $R^6$ to $R^9$ are independently =O and a lower alkyl.

12. The compound according to claim 1 or a salt thereof, which is N-(2,4-dimethyl-3-oxo-3,4-dihydro-2H-1,4-benzoxazin-6-yl)-2-(piperidin-1-ylmethyl)biphenyl-4-carboxamide.

13. The compound according to claim 1 or a salt thereof, which is 2-(piperidin-1-ylmethyl)-N-(2,2,4-trimethyl-3-oxo-3,4-dihydro-2H-1,4-benzoxazin-6-yl)biphenyl-4-carboxamide.

14. The compound according to claim 1 or a salt thereof, which is N-[(2R)-2-methyl-3-oxo-3,4-dihydro-2H-1,4-benzoxazin-6-yl]-2-(piperidin-1-ylmethyl)biphenyl-4-carboxamide.

15. The compound according to claim 1 or a salt thereof, which is 2-{[ethyl(2-hydroxy-2-methylpropyl)amino]methyl}-N-(2-methyl-3-oxo-3,4-dihydro-2H-1,4-benzoxazin-6-yl)biphenyl-4-carboxamide.

16. The compound according to claim 1 or a salt thereof, which is at least one compound selected from the group consisting of 2-[(4-methyl-1,3'-bipiperidin-1'-yl)methyl]-N-(2-methyl-3-oxo-3,4-dihydro-2H-1,4-benzoxazin-6-yl)biphenyl-4-carboxamide, and 2-{[isobutyl(2-piperidin-1-ylethyl)amino]methyl}-N-(2-methyl-3-oxo-3,4-dihydro-2H-1,4-benzoxazin-6-yl)biphenyl-4-carboxamide.

17. A pharmaceutical composition comprising the benzamide compound according to claim 1, or a salt thereof, and a pharmaceutically acceptable carrier.

18. A method for treating pain, which comprises administering a therapeutically effective amount of the benzamide compound according to claim 1 or a salt thereof, to a subject in need thereof.

19. The compound according to claim 1 or a salt thereof, wherein said 5- to 8-membered saturated or partially unsaturated monocyclic heterocycle which contains one N atom and may further contain one heteroatom selected from the group consisting of N, S, and O is a pyrrolidine ring, a piperidine ring, a piperazine ring, an azepane ring, a diazepane ring, a morpholine ring, a thiomorpholine ring, or a tetrahydropyridine ring.

* * * * *